US011185677B2

(12) United States Patent
Salahieh et al.

(10) Patent No.: US 11,185,677 B2
(45) Date of Patent: Nov. 30, 2021

(54) INTRAVASCULAR FLUID MOVEMENT DEVICES, SYSTEMS, AND METHODS OF USE

(71) Applicant: Shifamed Holdings, LLC, Campbell, CA (US)

(72) Inventors: Amr Salahieh, Saratoga, CA (US); Claudio Argento, Felton, CA (US); Tom Saul, Moss Beach, CA (US); Brady Esch, San Jose, CA (US); Colin Mixter, Santa Clara, CA (US); Peter Brown, Palo Alto, CA (US); Anna Kerlo, Milpitas, CA (US); Daniel Hildebrand, Santa Cruz, CA (US); Daniel Varghai, Campbell, CA (US)

(73) Assignee: SHIFAMED HOLDINGS, LLC, Campbell, CA (US)

( * ) Notice: Subject to any disclaimer, the term of this patent is extended or adjusted under 35 U.S.C. 154(b) by 0 days.

(21) Appl. No.: 16/523,949

(22) Filed: Jul. 26, 2019

(65) Prior Publication Data

US 2019/0344001 A1    Nov. 14, 2019

Related U.S. Application Data

(63) Continuation of application No. PCT/US2018/036506, filed on Jun. 7, 2018.
(Continued)

(51) Int. Cl.
*A61M 60/00* (2021.01)
*A61M 60/135* (2021.01)
(Continued)

(52) U.S. Cl.
CPC ........ *A61M 60/135* (2021.01); *A61M 60/205* (2021.01); *A61M 60/50* (2021.01);
(Continued)

(58) Field of Classification Search
CPC .................................................. A61M 60/414
See application file for complete search history.

(56) References Cited

U.S. PATENT DOCUMENTS

| 1,061,107 A | 5/1913 | Nordmark |
| 1,596,933 A | 8/1926 | Kister |

(Continued)

FOREIGN PATENT DOCUMENTS

| CA | 2739899 C | 5/2017 |
| CN | 1040073 A | 2/1990 |

(Continued)

OTHER PUBLICATIONS

Park et al.; Biologically Inspired, Open, Helicoid Impeller Design for Mechanical Circulatory Assist; ASAIO Journal (American Society for Artificial Internal Organs); DOI: 10.1097/MAT.0000000000001090; Oct. 23, 2019.
(Continued)

*Primary Examiner* — John R Downey
*Assistant Examiner* — Anant A Gupta
(74) *Attorney, Agent, or Firm* — Shay Glenn LLP

(57) ABSTRACT

An intravascular fluid movement device that includes an expandable member having a collapsed, delivery configuration and an expanded, deployed configuration, the expandable member having a proximal end and a distal end, a rotatable member disposed radially and axially within the expandable member, and a conduit coupled to the expandable member, the conduit at least partially defining a blood flow lumen between a distal end of the conduit and a proximal end of the conduit, the conduit disposed solely radially inside of the expandable member in a distal section of the expandable member.

5 Claims, 21 Drawing Sheets

Related U.S. Application Data

(60) Provisional application No. 62/516,296, filed on Jun. 7, 2017, provisional application No. 62/542,488, filed on Aug. 8, 2017.

(51) Int. Cl.
  *A61M 60/50* (2021.01)
  *A61M 60/205* (2021.01)
  *A61M 60/148* (2021.01)
  *A61M 60/857* (2021.01)

(52) U.S. Cl.
  CPC ......... *A61M 60/148* (2021.01); *A61M 60/857* (2021.01); *A61M 2230/30* (2013.01)

(56) References Cited

U.S. PATENT DOCUMENTS

| | | |
|---|---|---|
| 3,175,555 A | 3/1965 | Ling |
| 3,178,833 A | 4/1965 | Gulbransen, Jr. |
| 3,208,448 A | 9/1965 | Woodward |
| 3,233,609 A | 2/1966 | Leucci |
| 3,421,497 A | 1/1969 | Chesnut |
| 3,502,412 A | 3/1970 | Burns |
| 3,504,662 A | 4/1970 | Jones |
| 3,505,987 A | 4/1970 | Heilman |
| 3,568,659 A | 3/1971 | Karnegis |
| 3,693,612 A | 9/1972 | Donahoe et al. |
| 3,734,648 A | 5/1973 | Nielson |
| 3,774,243 A | 11/1973 | Ng et al. |
| 3,837,922 A | 9/1974 | Ng et al. |
| 3,841,837 A | 10/1974 | Kitrilakis et al. |
| 3,860,968 A | 1/1975 | Shapiro |
| 3,919,722 A | 11/1975 | Harmison |
| 4,015,590 A | 4/1977 | Normann |
| 4,037,984 A | 7/1977 | Rafferty et al. |
| 4,046,137 A | 9/1977 | Curless et al. |
| 4,058,857 A | 11/1977 | Runge et al. |
| 4,093,726 A | 6/1978 | Winn et al. |
| 4,135,253 A | 1/1979 | Reich et al. |
| 4,142,845 A | 3/1979 | Lepp et al. |
| 4,173,796 A | 11/1979 | Jarvik |
| 4,190,047 A | 2/1980 | Jacobsen et al. |
| 4,255,821 A | 3/1981 | Carol et al. |
| 4,289,141 A | 9/1981 | Cormier |
| 4,310,930 A | 1/1982 | Goldowsky |
| 4,311,133 A | 1/1982 | Robinson |
| 4,328,806 A | 5/1982 | Cooper |
| 4,370,983 A | 2/1983 | Lichtenstein |
| 4,381,005 A | 4/1983 | Bujan |
| 4,381,567 A | 5/1983 | Robinson et al. |
| 4,382,199 A | 5/1983 | Isaacson |
| 4,389,737 A | 6/1983 | Robinson et al. |
| 4,397,049 A | 8/1983 | Robinson et al. |
| 4,407,304 A | 10/1983 | Lieber et al. |
| 4,506,658 A | 3/1985 | Casile |
| 4,515,589 A | 5/1985 | Austin et al. |
| 4,522,195 A | 6/1985 | Schiff |
| 4,524,466 A | 6/1985 | Hall et al. |
| 4,551,073 A | 11/1985 | Schwab |
| 4,576,606 A | 3/1986 | Pol et al. |
| 4,585,004 A | 4/1986 | Brownlee |
| 4,585,007 A | 4/1986 | Uchigaki et al. |
| 4,599,081 A | 7/1986 | Cohen |
| 4,600,405 A | 7/1986 | Zibelin |
| 4,623,350 A | 11/1986 | Lapeyre et al. |
| 4,625,712 A | 12/1986 | Wampler |
| 4,652,265 A | 3/1987 | McDougall |
| 4,662,358 A | 5/1987 | Farrar et al. |
| 4,675,361 A | 6/1987 | Ward |
| 4,685,910 A | 8/1987 | Schweizer |
| 4,726,379 A | 2/1988 | Altman et al. |
| 4,753,221 A | 6/1988 | Kensey et al. |
| 4,767,289 A | 8/1988 | Parrott et al. |
| 4,771,111 A | 9/1988 | Horzewski et al. |
| 4,779,614 A | 10/1988 | Moise |
| 4,782,817 A | 11/1988 | Singh et al. |
| 4,785,795 A | 11/1988 | Singh |
| 4,802,650 A | 2/1989 | Stricker |
| 4,818,186 A | 4/1989 | Pastrone et al. |
| 4,826,481 A | 5/1989 | Sacks et al. |
| 4,846,831 A | 7/1989 | Skillin |
| 4,850,957 A | 7/1989 | Summers |
| 4,888,009 A | 12/1989 | Lederman et al. |
| 4,888,011 A | 12/1989 | Kung et al. |
| 4,902,272 A | 2/1990 | Milder et al. |
| 4,907,592 A | 3/1990 | Harper |
| 4,908,012 A | 3/1990 | Moise et al. |
| 4,919,647 A | 4/1990 | Nash |
| 4,936,759 A | 6/1990 | Clausen et al. |
| 4,961,738 A | 10/1990 | Mackin |
| 4,976,683 A | 12/1990 | Gauthier et al. |
| 4,995,857 A | 2/1991 | Arnold |
| 5,026,367 A | 6/1991 | Leckrone et al. |
| D318,113 S | 7/1991 | Moutafis et al. |
| 5,045,051 A | 9/1991 | Milder et al. |
| 5,046,503 A | 9/1991 | Schneiderman |
| 5,047,147 A | 9/1991 | Chevallet et al. |
| 5,049,134 A | 9/1991 | Golding et al. |
| 5,084,064 A | 1/1992 | Barak et al. |
| 5,089,016 A | 2/1992 | Millner et al. |
| 5,090,957 A | 2/1992 | Moutafis et al. |
| 5,092,844 A | 3/1992 | Schwartz et al. |
| 5,092,879 A | 3/1992 | Jarvik |
| 5,112,200 A | 5/1992 | Isaacson et al. |
| 5,112,292 A | 5/1992 | Hwang et al. |
| 5,114,399 A | 5/1992 | Kovalcheck |
| 5,116,305 A | 5/1992 | Milder et al. |
| 5,139,517 A | 8/1992 | Corral |
| 5,145,333 A | 9/1992 | Smith |
| 5,147,281 A | 9/1992 | Thornton et al. |
| 5,171,264 A | 12/1992 | Merrill |
| 5,180,378 A | 1/1993 | Kung et al. |
| 5,192,314 A | 3/1993 | Daskalakis |
| 5,200,050 A | 4/1993 | Ivory et al. |
| 5,205,721 A | 4/1993 | Isaacson |
| 5,211,546 A | 5/1993 | Isaacson et al. |
| 5,261,411 A | 11/1993 | Hughes |
| 5,270,005 A | 12/1993 | Raible |
| 5,300,111 A | 4/1994 | Panton et al. |
| 5,300,112 A | 4/1994 | Barr |
| 5,314,418 A * | 5/1994 | Takano ............... A61M 1/3659 604/540 |
| 5,322,413 A | 6/1994 | Vescovini et al. |
| 5,326,344 A | 7/1994 | Bramm et al. |
| 5,363,856 A | 11/1994 | Hughes et al. |
| 5,397,349 A | 3/1995 | Kolff et al. |
| 5,399,074 A | 3/1995 | Nose et al. |
| 5,405,251 A | 4/1995 | Sipin |
| 5,443,504 A | 8/1995 | Hill |
| 5,486,192 A | 1/1996 | Walinsky et al. |
| 5,487,727 A | 1/1996 | Snider et al. |
| 5,507,629 A | 4/1996 | Jarvik |
| 5,507,795 A | 4/1996 | Chiang et al. |
| 5,510,267 A | 4/1996 | Marshall |
| 5,512,042 A | 4/1996 | Montoya et al. |
| 5,531,789 A | 7/1996 | Yamazaki et al. |
| 5,628,731 A | 5/1997 | Dodge et al. |
| 5,630,835 A | 5/1997 | Brownlee |
| 5,643,172 A | 7/1997 | Kung et al. |
| 5,643,215 A | 7/1997 | Fuhrman et al. |
| 5,653,696 A | 8/1997 | Shiber |
| 5,662,643 A | 9/1997 | Kung et al. |
| 5,676,526 A | 10/1997 | Kuwana et al. |
| 5,683,231 A | 11/1997 | Nakazawa et al. |
| 5,702,365 A | 12/1997 | King |
| 5,713,730 A | 2/1998 | Nose et al. |
| 5,749,839 A | 5/1998 | Kovacs |
| 5,751,125 A | 5/1998 | Weiss |
| 5,759,148 A | 6/1998 | Sipin |
| 5,766,207 A | 6/1998 | Potter et al. |
| 5,776,096 A | 7/1998 | Fields |
| 5,800,138 A | 9/1998 | Vives |
| 5,800,457 A | 9/1998 | Gelbfish |

(56) References Cited

U.S. PATENT DOCUMENTS

| | | |
|---|---|---|
| 5,803,720 A | 9/1998 | Ohara et al. |
| 5,814,076 A | 9/1998 | Brownlee |
| 5,814,102 A | 9/1998 | Guldner et al. |
| 5,851,174 A | 12/1998 | Jarvik et al. |
| 5,888,241 A | 3/1999 | Jarvik |
| 5,906,579 A | 5/1999 | Vander Salm et al. |
| 5,910,124 A | 6/1999 | Rubin |
| 5,919,369 A | 7/1999 | Ash |
| 5,941,813 A | 8/1999 | Sievers et al. |
| 5,964,694 A * | 10/1999 | Siess ............... H02K 5/08 415/900 |
| 5,984,893 A | 11/1999 | Ward |
| 6,013,058 A | 1/2000 | Prosl et al. |
| 6,022,363 A | 2/2000 | Walker et al. |
| 6,030,336 A | 2/2000 | Franchi |
| 6,042,347 A | 3/2000 | Scholl et al. |
| 6,066,085 A | 5/2000 | Heilman et al. |
| 6,066,152 A | 5/2000 | Strauss et al. |
| 6,068,588 A | 5/2000 | Goldowsky |
| 6,071,093 A | 6/2000 | Hart |
| 6,071,258 A | 6/2000 | Dalke et al. |
| 6,082,105 A | 7/2000 | Miyata |
| 6,101,406 A | 8/2000 | Hacker et al. |
| 6,106,509 A | 8/2000 | Loubser |
| 6,113,536 A | 9/2000 | Aboul Hosn et al. |
| 6,117,130 A | 9/2000 | Kung |
| 6,117,390 A | 9/2000 | Corey |
| 6,120,537 A | 9/2000 | Wampler |
| 6,123,726 A | 9/2000 | Mori et al. |
| 6,129,660 A | 10/2000 | Nakazeki et al. |
| 6,136,025 A | 10/2000 | Barbut et al. |
| 6,139,487 A | 10/2000 | Siess |
| 6,142,752 A | 11/2000 | Akamatsu et al. |
| 6,146,771 A | 11/2000 | Wirt et al. |
| 6,149,683 A | 11/2000 | Lancisi et al. |
| 6,152,704 A | 11/2000 | Aboul Hosn et al. |
| 6,155,969 A | 12/2000 | Schima et al. |
| 6,180,058 B1 | 1/2001 | Lindsay |
| 6,197,055 B1 | 3/2001 | Matthews |
| 6,197,289 B1 | 3/2001 | Wirt et al. |
| 6,210,133 B1 | 4/2001 | Aboul Hosn et al. |
| 6,210,318 B1 | 4/2001 | Lederman |
| 6,228,023 B1 | 5/2001 | Zaslavsky et al. |
| 6,236,883 B1 | 5/2001 | Ciaccio et al. |
| 6,254,359 B1 | 7/2001 | Aber |
| 6,270,831 B2 | 8/2001 | Kumar et al. |
| 6,273,861 B1 | 8/2001 | Bates et al. |
| 6,283,949 B1 | 9/2001 | Roorda |
| 6,287,319 B1 | 9/2001 | Aboul Hosn et al. |
| 6,290,685 B1 | 9/2001 | Insley et al. |
| 6,312,462 B1 | 11/2001 | McDermott et al. |
| 6,314,322 B1 | 11/2001 | Rosenberg |
| 6,319,231 B1 | 11/2001 | Andrulitis |
| 6,361,292 B1 | 3/2002 | Chang et al. |
| 6,361,501 B1 | 3/2002 | Amano et al. |
| 6,364,833 B1 | 4/2002 | Valerio et al. |
| 6,398,715 B1 | 6/2002 | Magovern et al. |
| 6,400,991 B1 | 6/2002 | Kung |
| 6,406,267 B1 | 6/2002 | Mondiere |
| 6,406,422 B1 | 6/2002 | Landesberg |
| 6,419,657 B1 | 7/2002 | Pacetti |
| 6,422,990 B1 | 7/2002 | Prem |
| 6,432,136 B1 | 8/2002 | Weiss et al. |
| 6,443,944 B1 | 9/2002 | Doshi et al. |
| 6,443,983 B1 | 9/2002 | Nagyszalanczy et al. |
| 6,445,956 B1 | 9/2002 | Laird et al. |
| 6,447,265 B1 | 9/2002 | Antaki et al. |
| 6,447,266 B2 | 9/2002 | Antaki et al. |
| 6,447,441 B1 | 9/2002 | Yu et al. |
| 6,497,680 B1 | 12/2002 | Holst et al. |
| 6,503,224 B1 | 1/2003 | Forman et al. |
| 6,503,450 B1 | 1/2003 | Afzal et al. |
| 6,508,787 B2 | 1/2003 | Erbel et al. |
| 6,508,806 B1 | 1/2003 | Hoste |
| 6,527,699 B1 | 3/2003 | Goldowsky |
| 6,533,716 B1 | 3/2003 | Schmitz-Rode et al. |
| 6,533,724 B2 | 3/2003 | McNair |
| 6,537,315 B2 | 3/2003 | Yamazaki et al. |
| 6,540,658 B1 | 4/2003 | Fasciano et al. |
| 6,540,659 B1 | 4/2003 | Milbocker |
| 6,544,543 B1 | 4/2003 | Mandrusov et al. |
| 6,547,716 B1 | 4/2003 | Milbocker |
| 6,562,022 B2 | 5/2003 | Hoste et al. |
| 6,572,529 B2 | 6/2003 | Wilk |
| 6,572,534 B1 | 6/2003 | Milbocker et al. |
| 6,595,943 B1 | 7/2003 | Burbank |
| 6,602,182 B1 | 8/2003 | Milbocker |
| 6,616,596 B1 | 9/2003 | Milbocker |
| 6,620,120 B2 | 9/2003 | Landry et al. |
| 6,623,420 B2 | 9/2003 | Reich et al. |
| 6,626,821 B1 | 9/2003 | Kung et al. |
| 6,626,889 B1 | 9/2003 | Simpson et al. |
| 6,626,935 B1 | 9/2003 | Ainsworth et al. |
| 6,632,215 B1 | 10/2003 | Lemelson |
| 6,635,083 B1 | 10/2003 | Cheng et al. |
| 6,656,220 B1 | 12/2003 | Gomez et al. |
| 6,669,624 B2 | 12/2003 | Frazier |
| 6,669,662 B1 | 12/2003 | Webler |
| 6,676,679 B1 | 1/2004 | Mueller et al. |
| 6,688,869 B1 | 2/2004 | Simonds |
| 6,699,231 B1 | 3/2004 | Sterman et al. |
| 6,709,382 B1 | 3/2004 | Horner |
| 6,730,102 B1 | 5/2004 | Burdulis et al. |
| 6,746,416 B2 | 6/2004 | Hubbard et al. |
| 6,749,615 B2 | 6/2004 | Burdulis et al. |
| 6,769,871 B2 | 8/2004 | Yamazaki |
| 6,790,171 B1 | 9/2004 | Grundeman et al. |
| 6,811,749 B2 | 11/2004 | Lindsay |
| 6,821,295 B1 | 11/2004 | Farrar |
| 6,837,890 B1 | 1/2005 | Chludzinski et al. |
| 6,846,296 B1 | 1/2005 | Milbocker et al. |
| 6,866,650 B2 | 3/2005 | Stevens et al. |
| 6,879,126 B2 | 4/2005 | Paden et al. |
| 6,884,210 B2 | 4/2005 | Nose et al. |
| 6,908,280 B2 | 6/2005 | Yamazaki |
| 6,908,435 B1 | 6/2005 | Mueller et al. |
| 6,929,632 B2 | 8/2005 | Nita et al. |
| 6,929,660 B1 | 8/2005 | Ainsworth et al. |
| 6,942,672 B2 | 9/2005 | Heilman et al. |
| 6,945,978 B1 | 9/2005 | Hyde |
| 6,949,066 B2 | 9/2005 | Bearnson et al. |
| 6,969,345 B2 | 11/2005 | Jassawalla et al. |
| 6,981,942 B2 | 1/2006 | Khaw et al. |
| 7,022,100 B1 | 4/2006 | Aboul Hosn et al. |
| 7,025,742 B2 | 4/2006 | Rubenstein et al. |
| 7,027,875 B2 | 4/2006 | Siess et al. |
| 7,029,483 B2 | 4/2006 | Schwartz |
| 7,037,253 B2 | 5/2006 | French et al. |
| 7,048,747 B2 | 5/2006 | Arcia et al. |
| 7,074,018 B2 | 7/2006 | Chang |
| 7,108,652 B2 | 9/2006 | Stenberg et al. |
| 7,118,525 B2 | 10/2006 | Coleman et al. |
| 7,122,151 B2 | 10/2006 | Reeder et al. |
| 7,125,376 B2 | 10/2006 | Viole et al. |
| 7,126,310 B1 | 10/2006 | Barron |
| 7,150,711 B2 | 12/2006 | Nüsser et al. |
| 7,155,291 B2 | 12/2006 | Zarinetchi et al. |
| 7,172,551 B2 | 2/2007 | Leasure |
| 7,189,260 B2 | 3/2007 | Horvath et al. |
| 7,229,258 B2 | 6/2007 | Wood et al. |
| 7,229,402 B2 | 6/2007 | Diaz et al. |
| 7,238,151 B2 | 7/2007 | Frazier |
| 7,244,224 B2 | 7/2007 | Tsukahara et al. |
| 7,247,166 B2 | 7/2007 | Pienknagura |
| 7,303,581 B2 | 12/2007 | Peralta |
| 7,331,972 B1 | 2/2008 | Cox |
| 7,331,987 B1 | 2/2008 | Cox |
| 7,361,726 B2 | 4/2008 | Pacetti et al. |
| 7,377,927 B2 | 5/2008 | Burdulis et al. |
| 7,392,077 B2 | 6/2008 | Mueller et al. |
| 7,393,181 B2 | 7/2008 | McBride et al. |
| 7,396,327 B2 | 7/2008 | Morello |
| 7,479,102 B2 | 1/2009 | Jarvik |
| 7,520,850 B2 | 4/2009 | Brockway |

(56) References Cited

U.S. PATENT DOCUMENTS

| | | |
|---|---|---|
| 7,524,277 B1 | 4/2009 | Wang et al. |
| 7,541,000 B2 | 6/2009 | Stringer et al. |
| 7,544,160 B2 | 6/2009 | Gross |
| 7,547,391 B2 | 6/2009 | Petrie |
| 7,585,322 B2 | 9/2009 | Azzolina |
| 7,588,530 B2 | 9/2009 | Heilman et al. |
| 7,588,549 B2 | 9/2009 | Eccleston |
| 7,591,199 B2 | 9/2009 | Weldon et al. |
| 7,611,478 B2 | 11/2009 | Lucke et al. |
| 7,628,756 B2 | 12/2009 | Hacker et al. |
| 7,713,259 B2 | 5/2010 | Gosiengfiao et al. |
| RE41,394 E | 6/2010 | Bugge et al. |
| 7,736,296 B2 | 6/2010 | Siess et al. |
| 7,736,375 B2 | 6/2010 | Crow |
| 7,758,492 B2 | 7/2010 | Weatherbee |
| 7,776,991 B2 | 8/2010 | Pacetti et al. |
| 7,780,628 B1 | 8/2010 | Keren et al. |
| 7,794,419 B2 | 9/2010 | Paolini et al. |
| 7,794,743 B2 | 9/2010 | Simhambhatla et al. |
| 7,819,834 B2 | 10/2010 | Paul |
| 7,828,710 B2 | 11/2010 | Shifflette |
| 7,833,239 B2 | 11/2010 | Nash |
| 7,841,976 B2 | 11/2010 | McBride et al. |
| 7,850,594 B2 | 12/2010 | Sutton et al. |
| 7,862,501 B2 | 1/2011 | Woodard |
| 7,878,967 B1 | 2/2011 | Khanal |
| 7,914,436 B1 | 3/2011 | Kung |
| 7,922,657 B2 | 4/2011 | Gillinov et al. |
| 7,942,804 B2 | 5/2011 | Khaw |
| 7,963,905 B2 | 6/2011 | Salmonsen et al. |
| 7,972,122 B2 | 7/2011 | LaRose et al. |
| 7,972,291 B2 | 7/2011 | Ibragimov |
| 7,985,442 B2 | 7/2011 | Gong |
| 7,988,728 B2 | 8/2011 | Ayre |
| 7,993,259 B2 | 8/2011 | Kang et al. |
| 7,993,260 B2 | 8/2011 | Bolling |
| 7,993,358 B2 | 8/2011 | O'Brien |
| 7,998,054 B2 | 8/2011 | Bolling |
| 7,998,190 B2 | 8/2011 | Gharib et al. |
| 8,012,079 B2 | 9/2011 | Delgado |
| 8,012,194 B2 | 9/2011 | Edwin et al. |
| 8,012,508 B2 | 9/2011 | Ludwig |
| 8,029,728 B2 | 10/2011 | Lindsay |
| 8,034,098 B1 | 10/2011 | Callas et al. |
| 8,048,442 B1 | 11/2011 | Hossainy et al. |
| 8,052,749 B2 | 11/2011 | Salahieh et al. |
| 8,070,742 B2 | 12/2011 | Woo |
| 8,070,804 B2 | 12/2011 | Hyde et al. |
| 8,075,472 B2 | 12/2011 | Zilbershlag et al. |
| 8,079,948 B2 | 12/2011 | Shifflette |
| 8,083,726 B1 | 12/2011 | Wang |
| 8,123,669 B2 | 2/2012 | Siess et al. |
| 8,123,674 B2 | 2/2012 | Kuyava |
| 8,133,272 B2 | 3/2012 | Hyde |
| RE43,299 E | 4/2012 | Siess |
| 8,152,035 B2 | 4/2012 | Earl |
| 8,152,845 B2 | 4/2012 | Bourque |
| 8,153,083 B2 | 4/2012 | Briggs |
| 8,157,719 B1 | 4/2012 | Ainsworth et al. |
| 8,157,721 B2 | 4/2012 | Sugiura |
| 8,157,758 B2 | 4/2012 | Pecor et al. |
| 8,158,062 B2 | 4/2012 | Dykes et al. |
| 8,162,021 B2 | 4/2012 | Tomasetti et al. |
| 8,167,589 B2 | 5/2012 | Hidaka et al. |
| 8,172,783 B1 | 5/2012 | Ray |
| 8,177,750 B2 | 5/2012 | Steinbach et al. |
| 8,187,324 B2 | 5/2012 | Webler et al. |
| 8,197,463 B2 | 6/2012 | Intoccia |
| 8,210,829 B2 | 7/2012 | Horvath et al. |
| 8,241,199 B2 | 8/2012 | Maschke |
| 8,257,258 B2 | 9/2012 | Zocchi |
| 8,257,375 B2 | 9/2012 | Maschke |
| 8,266,943 B2 | 9/2012 | Miyakoshi et al. |
| D669,585 S | 10/2012 | Bourque |
| 8,277,476 B2 | 10/2012 | Taylor et al. |
| 8,282,359 B2 | 10/2012 | Ayre et al. |
| 8,292,908 B2 | 10/2012 | Nieman et al. |
| D671,646 S | 11/2012 | Bourque et al. |
| 8,303,482 B2 | 11/2012 | Schima et al. |
| 8,323,173 B2 | 12/2012 | Benkowski et al. |
| 8,328,750 B2 | 12/2012 | Peters et al. |
| 8,329,114 B2 | 12/2012 | Temple |
| 8,329,158 B2 | 12/2012 | Hossainy et al. |
| 8,366,599 B2 | 2/2013 | Tansley et al. |
| 8,372,137 B2 | 2/2013 | Pienknagura |
| 8,377,033 B2 | 2/2013 | Basu et al. |
| 8,377,083 B2 | 2/2013 | Mauch et al. |
| 8,382,695 B1 | 2/2013 | Patel |
| 8,388,649 B2 | 3/2013 | Woodard et al. |
| 8,419,609 B2 | 4/2013 | Shambaugh et al. |
| 8,419,944 B2 | 4/2013 | Alkanhal |
| 8,439,909 B2 | 5/2013 | Wang et al. |
| 8,449,444 B2 | 5/2013 | Poirier |
| 8,454,683 B2 | 6/2013 | Rafiee et al. |
| 8,485,961 B2 | 7/2013 | Campbell et al. |
| 8,496,874 B2 | 7/2013 | Gellman et al. |
| 8,500,620 B2 | 8/2013 | Lu et al. |
| 8,506,471 B2 | 8/2013 | Bourque |
| 8,535,211 B2 | 9/2013 | Campbell et al. |
| 8,535,212 B2 | 9/2013 | Robert |
| 8,538,515 B2 | 9/2013 | Atanasoska et al. |
| 8,545,382 B2 | 10/2013 | Suzuki et al. |
| 8,545,447 B2 | 10/2013 | Demarais et al. |
| 8,562,509 B2 | 10/2013 | Bates |
| 8,568,289 B2 | 10/2013 | Mazur |
| 8,579,858 B2 | 11/2013 | Reitan et al. |
| 8,579,967 B2 | 11/2013 | Webler et al. |
| 8,585,572 B2 | 11/2013 | Mehmanesh |
| 8,586,527 B2 | 11/2013 | Singh |
| 8,591,393 B2 | 11/2013 | Walters et al. |
| 8,591,394 B2 | 11/2013 | Peters et al. |
| 8,591,449 B2 | 11/2013 | Hudson |
| 8,591,538 B2 | 11/2013 | Gellman |
| 8,591,539 B2 | 11/2013 | Gellman |
| D696,769 S | 12/2013 | Schenck et al. |
| 8,597,170 B2 | 12/2013 | Walters et al. |
| 8,608,661 B1 | 12/2013 | Mandrusov et al. |
| 8,613,777 B2 | 12/2013 | Siess et al. |
| 8,613,892 B2 | 12/2013 | Stafford |
| 8,617,239 B2 | 12/2013 | Reitan |
| 8,631,680 B2 | 1/2014 | Fleischli et al. |
| 8,632,449 B2 | 1/2014 | Masuzawa et al. |
| 8,641,594 B2 | 2/2014 | LaRose et al. |
| 8,657,871 B2 | 2/2014 | Limon |
| 8,657,875 B2 | 2/2014 | Kung et al. |
| 8,668,473 B2 | 3/2014 | LaRose et al. |
| 8,684,903 B2 | 4/2014 | Nour |
| 8,690,749 B1 | 4/2014 | Nunez |
| 8,690,823 B2 | 4/2014 | Yribarren et al. |
| 8,697,058 B2 | 4/2014 | Basu et al. |
| 8,708,948 B2 | 4/2014 | Consigny et al. |
| 8,715,151 B2 | 5/2014 | Poirier |
| 8,715,156 B2 | 5/2014 | Jayaraman |
| 8,715,707 B2 | 5/2014 | Hossainy et al. |
| 8,721,516 B2 | 5/2014 | Scheckel |
| 8,721,517 B2 | 5/2014 | Zeng et al. |
| 8,734,331 B2 | 5/2014 | Evans et al. |
| 8,734,508 B2 | 5/2014 | Hastings et al. |
| 8,739,727 B2 | 6/2014 | Austin et al. |
| 8,740,920 B2 | 6/2014 | Goldfarb et al. |
| 8,741,287 B2 | 6/2014 | Brophy et al. |
| 8,758,388 B2 | 6/2014 | Pah |
| 8,766,788 B2 | 7/2014 | D'Ambrosio |
| 8,777,832 B1 | 7/2014 | Wang et al. |
| 8,790,399 B2 | 7/2014 | Frazier et al. |
| 8,795,576 B2 | 8/2014 | Tao et al. |
| 8,814,543 B2 | 8/2014 | Liebing |
| 8,814,776 B2 | 8/2014 | Hastie et al. |
| 8,814,933 B2 | 8/2014 | Siess |
| 8,815,274 B2 | 8/2014 | DesNoyer et al. |
| 8,821,366 B2 | 9/2014 | Farnan et al. |
| 8,837,096 B2 | 9/2014 | Seebruch |
| 8,840,539 B2 | 9/2014 | Zilbershlag |
| 8,840,566 B2 | 9/2014 | Seibel et al. |

(56) References Cited

U.S. PATENT DOCUMENTS

| | | |
|---|---|---|
| 8,849,398 B2 | 9/2014 | Evans |
| 8,862,232 B2 | 10/2014 | Zarinetchi et al. |
| 8,864,642 B2 | 10/2014 | Scheckel |
| 8,876,685 B2 | 11/2014 | Crosby et al. |
| 8,882,744 B2 | 11/2014 | Dormanen et al. |
| 8,888,675 B2 | 11/2014 | Stankus et al. |
| 8,894,387 B2 | 11/2014 | White |
| 8,894,561 B2 | 11/2014 | Callaway et al. |
| 8,897,873 B2 | 11/2014 | Schima et al. |
| 8,900,060 B2 | 12/2014 | Liebing |
| 8,905,910 B2 | 12/2014 | Reichenbach et al. |
| 8,927,700 B2 | 1/2015 | McCauley et al. |
| 8,932,141 B2 | 1/2015 | Liebing |
| 8,932,197 B2 | 1/2015 | Gregoric et al. |
| 8,942,828 B1 | 1/2015 | Schecter |
| 8,944,748 B2 | 2/2015 | Liebing |
| 8,945,159 B2 | 2/2015 | Nussbaum |
| 8,956,402 B2 | 2/2015 | Cohn |
| 8,961,387 B2 | 2/2015 | Duncan |
| 8,961,466 B2 | 2/2015 | Steinbach |
| 8,971,980 B2 | 3/2015 | Mace et al. |
| 8,974,519 B2 | 3/2015 | Gennrich et al. |
| 8,992,406 B2 | 3/2015 | Corbett |
| 8,997,349 B2 | 4/2015 | Mori et al. |
| 9,002,468 B2 | 4/2015 | Shea et al. |
| 9,023,010 B2 | 5/2015 | Chiu et al. |
| 9,028,216 B2 | 5/2015 | Schumacher et al. |
| 9,028,392 B2 | 5/2015 | Shifflette |
| 9,028,859 B2 | 5/2015 | Hossainy et al. |
| 9,033,863 B2 | 5/2015 | Jarvik |
| 9,033,909 B2 | 5/2015 | Aihara |
| 9,039,595 B2 | 5/2015 | Ayre et al. |
| 9,044,236 B2 | 6/2015 | Nguyen et al. |
| 9,056,159 B2 | 6/2015 | Medvedev et al. |
| 9,066,992 B2 | 6/2015 | Stankus et al. |
| 9,067,005 B2 | 6/2015 | Ozaki et al. |
| 9,067,006 B2 | 6/2015 | Toellner |
| 9,072,825 B2 | 7/2015 | Pfeffer et al. |
| 9,078,692 B2 | 7/2015 | Shturman et al. |
| 9,089,329 B2 | 7/2015 | Hoarau et al. |
| 9,089,634 B2 | 7/2015 | Schumacher et al. |
| 9,089,635 B2 | 7/2015 | Reichenbach et al. |
| 9,089,670 B2 | 7/2015 | Scheckel |
| 9,095,428 B2 | 8/2015 | Kabir et al. |
| 9,096,703 B2 | 8/2015 | Li et al. |
| 9,101,302 B2 | 8/2015 | Mace et al. |
| 9,125,977 B2 | 9/2015 | Nishimura et al. |
| 9,127,680 B2 | 9/2015 | Yanai et al. |
| 9,138,516 B2 | 9/2015 | Vischer et al. |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,168,361 B2 | 10/2015 | Ehrenreich et al. |
| 9,180,227 B2 | 11/2015 | Ludwig et al. |
| 9,180,235 B2 | 11/2015 | Forsell |
| 9,192,705 B2 | 11/2015 | Yanai et al. |
| 9,199,020 B2 | 12/2015 | Siess |
| 9,217,442 B2 | 12/2015 | Wiessler et al. |
| D746,975 S | 1/2016 | Schenck et al. |
| 9,227,002 B1 | 1/2016 | Giridharan et al. |
| 9,239,049 B2 | 1/2016 | Jamagin et al. |
| 9,265,870 B2 | 2/2016 | Reichenbach et al. |
| 9,278,189 B2 | 3/2016 | Corbett |
| 9,283,314 B2 | 3/2016 | Prasad et al. |
| 9,291,591 B2 | 3/2016 | Simmons et al. |
| 9,295,550 B2 | 3/2016 | Nguyen et al. |
| 9,295,767 B2 | 3/2016 | Schmid et al. |
| 9,308,302 B2 | 4/2016 | Zeng |
| 9,308,304 B2 | 4/2016 | Peters et al. |
| 9,314,558 B2 | 4/2016 | Er |
| 9,314,559 B2 | 4/2016 | Smith et al. |
| 9,328,741 B2 | 5/2016 | Liebing |
| 9,333,284 B2 | 5/2016 | Thompson et al. |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,255 B2 | 6/2016 | Weber |
| 9,364,592 B2 | 6/2016 | McBride et al. |
| 9,370,613 B2 | 6/2016 | Hsu et al. |
| 9,375,445 B2 | 6/2016 | Hossainy et al. |
| 9,381,285 B2 | 7/2016 | Ozaki et al. |
| 9,387,284 B2 | 7/2016 | Heilman et al. |
| 9,409,012 B2 | 8/2016 | Eidenschink et al. |
| 9,416,783 B2 | 8/2016 | Schumacher et al. |
| 9,416,791 B2 | 8/2016 | Toellner |
| 9,421,311 B2 | 8/2016 | Tanner et al. |
| 9,433,713 B2 | 9/2016 | Corbett et al. |
| 9,435,450 B2 | 9/2016 | Muennich |
| 9,446,179 B2 | 9/2016 | Keenan et al. |
| 9,452,249 B2 | 9/2016 | Kearsley et al. |
| 9,474,840 B2 | 10/2016 | Siess |
| 9,486,565 B2 | 11/2016 | Göllner et al. |
| 9,492,601 B2 | 11/2016 | Casas et al. |
| 9,504,491 B2 | 11/2016 | Callas et al. |
| 9,511,179 B2 | 12/2016 | Casas et al. |
| 9,522,257 B2 | 12/2016 | Webler |
| 9,526,818 B2 | 12/2016 | Kearsley et al. |
| 9,533,084 B2 | 1/2017 | Siess et al. |
| 9,533,085 B2 | 1/2017 | Hanna |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,555,177 B2 | 1/2017 | Curtis et al. |
| 9,556,873 B2 | 1/2017 | Yanai et al. |
| 9,561,309 B2 | 2/2017 | Glauser et al. |
| 9,561,313 B2 | 2/2017 | Taskin |
| 9,592,328 B2 | 3/2017 | Jeevanandam et al. |
| 9,603,983 B2 | 3/2017 | Roehn et al. |
| 9,603,984 B2 | 3/2017 | Romero et al. |
| 9,611,743 B2 | 4/2017 | Toellner et al. |
| 9,612,182 B2 | 4/2017 | Olde et al. |
| 9,616,157 B2 | 4/2017 | Akdis |
| 9,616,159 B2 | 4/2017 | Anderson et al. |
| 9,623,163 B1 | 4/2017 | Fischi |
| 9,631,754 B2 | 4/2017 | Richardson et al. |
| 9,642,984 B2 | 5/2017 | Schumacher et al. |
| 9,656,010 B2 | 5/2017 | Burke |
| 9,656,030 B1 | 5/2017 | Webler et al. |
| 9,662,211 B2 | 5/2017 | Hodson et al. |
| 9,669,141 B2 | 6/2017 | Parker et al. |
| 9,669,142 B2 | 6/2017 | Spanier et al. |
| 9,669,143 B2 | 6/2017 | Guerrero |
| 9,675,450 B2 | 6/2017 | Straka et al. |
| 9,675,738 B2 | 6/2017 | Tanner et al. |
| 9,675,739 B2 | 6/2017 | Tanner et al. |
| 9,675,742 B2 | 6/2017 | Casas et al. |
| 9,687,596 B2 | 6/2017 | Poirier |
| 9,687,630 B2 | 6/2017 | Basu et al. |
| 9,700,659 B2 | 7/2017 | Kantrowitz et al. |
| 9,713,662 B2 | 7/2017 | Rosenberg et al. |
| 9,713,663 B2 | 7/2017 | Medvedev et al. |
| 9,715,839 B2 | 7/2017 | Pybus et al. |
| 9,717,615 B2 | 8/2017 | Grandt |
| 9,717,832 B2 | 8/2017 | Taskin et al. |
| 9,717,839 B2 | 8/2017 | Hashimoto |
| 9,726,195 B2 | 8/2017 | Cecere et al. |
| 9,731,058 B2 | 8/2017 | Siebenhaar et al. |
| 9,731,101 B2 | 8/2017 | Bertrand et al. |
| 9,737,361 B2 | 8/2017 | Magana et al. |
| 9,737,651 B2 | 8/2017 | Wampler |
| 9,744,280 B2 | 8/2017 | Schade et al. |
| 9,744,287 B2 | 8/2017 | Bulent et al. |
| 9,750,859 B2 | 9/2017 | Bulent et al. |
| 9,757,502 B2 | 9/2017 | Burke et al. |
| 9,770,202 B2 | 9/2017 | Ralston et al. |
| 9,770,543 B2 | 9/2017 | Tanner et al. |
| 9,771,801 B2 | 9/2017 | Schumacher et al. |
| 9,775,930 B2 | 10/2017 | Michal et al. |
| 9,782,279 B2 | 10/2017 | Kassab |
| 9,782,527 B2 | 10/2017 | Thomas et al. |
| 9,795,780 B2 | 10/2017 | Serna et al. |
| 9,801,987 B2 | 10/2017 | Farnan et al. |

(56) References Cited

U.S. PATENT DOCUMENTS

| | | |
|---|---|---|
| 9,801,992 B2 | 10/2017 | Giordano et al. |
| 9,821,098 B2 | 11/2017 | Horvath et al. |
| 9,821,146 B2 | 11/2017 | Tao et al. |
| 9,827,356 B2 | 11/2017 | Muller et al. |
| 9,833,314 B2 | 12/2017 | Corbett |
| 9,833,550 B2 | 12/2017 | Siess |
| 9,833,551 B2 | 12/2017 | Criscione et al. |
| 9,839,734 B1 | 12/2017 | Menon et al. |
| 9,844,618 B2 | 12/2017 | Muller-Spanka et al. |
| 9,850,906 B2 | 12/2017 | Ozaki et al. |
| 9,855,437 B2 | 1/2018 | Nguyen et al. |
| 9,861,504 B2 | 1/2018 | Abunassar et al. |
| 9,861,731 B2 | 1/2018 | Tamburino |
| 9,872,948 B2 | 1/2018 | Siess |
| 9,878,087 B2 | 1/2018 | Richardson et al. |
| 9,878,169 B2 | 1/2018 | Hossainy |
| 9,889,242 B2 | 2/2018 | Pfeffer et al. |
| 9,895,244 B2 | 2/2018 | Papp et al. |
| 9,895,475 B2 | 2/2018 | Toellner et al. |
| 9,907,890 B2 | 3/2018 | Muller |
| 9,907,892 B2 | 3/2018 | Broen et al. |
| 9,913,937 B2 | 3/2018 | Schwammenthal et al. |
| 9,918,822 B2 | 3/2018 | Abunassar et al. |
| 9,919,085 B2 | 3/2018 | Throckmorton et al. |
| 9,919,088 B2 | 3/2018 | Bonde et al. |
| 9,919,089 B2 | 3/2018 | Garrigue |
| 9,950,101 B2 | 4/2018 | Smith et al. |
| 9,956,410 B2 | 5/2018 | Deem et al. |
| 9,962,258 B2 | 5/2018 | Seguin et al. |
| 9,974,893 B2 | 5/2018 | Toellner |
| 9,974,894 B2 | 5/2018 | Morello |
| 9,981,078 B2 | 5/2018 | Jin et al. |
| 9,985,374 B2 | 5/2018 | Hodges |
| 9,987,407 B2 | 6/2018 | Grant et al. |
| 10,010,273 B2 | 7/2018 | Sloan et al. |
| 10,022,499 B2 | 7/2018 | Galasso |
| 10,028,835 B2 | 7/2018 | Kermode et al. |
| 10,029,037 B2 | 7/2018 | Muller et al. |
| 10,029,038 B2 | 7/2018 | Hodges |
| 10,029,039 B2 | 7/2018 | Dague et al. |
| 10,031,124 B2 | 7/2018 | Galasso |
| 10,034,972 B2 | 7/2018 | Wampler et al. |
| 10,039,873 B2 | 8/2018 | Siegenthaler |
| 10,046,146 B2 | 8/2018 | Manderfeld et al. |
| 10,058,349 B2 | 8/2018 | Gunderson et al. |
| 10,058,641 B2 | 8/2018 | Mollison et al. |
| 10,058,652 B2 | 8/2018 | Tsoukalis |
| 10,058,653 B2 | 8/2018 | Wang et al. |
| 10,077,777 B2 | 9/2018 | Horvath et al. |
| 10,080,828 B2 | 9/2018 | Wiesener et al. |
| 10,080,834 B2 | 9/2018 | Federspiel et al. |
| 10,080,871 B2 | 9/2018 | Schumacher et al. |
| 10,569,005 B2 | 2/2020 | Solem et al. |
| 2001/0003802 A1 | 6/2001 | Vitale |
| 2001/0023369 A1 | 9/2001 | Chobotov |
| 2001/0053928 A1 | 12/2001 | Edelman et al. |
| 2002/0057989 A1 | 5/2002 | Afzal et al. |
| 2002/0058971 A1 | 5/2002 | Zarinetchi et al. |
| 2002/0068848 A1 | 6/2002 | Zadini et al. |
| 2002/0072679 A1 | 6/2002 | Schock et al. |
| 2002/0128709 A1 | 9/2002 | Pless |
| 2002/0147495 A1 | 10/2002 | Petroff |
| 2003/0069465 A1 | 4/2003 | Benkowski et al. |
| 2003/0088151 A1 | 5/2003 | Kung et al. |
| 2003/0131995 A1 | 7/2003 | de Rouffignac et al. |
| 2003/0155111 A1 | 8/2003 | Vinegar et al. |
| 2003/0173081 A1 | 9/2003 | Vinegar et al. |
| 2003/0173082 A1 | 9/2003 | Vinegar et al. |
| 2003/0173085 A1 | 9/2003 | Vinegar et al. |
| 2003/0178191 A1 | 9/2003 | Maher et al. |
| 2003/0209348 A1 | 11/2003 | Ward et al. |
| 2004/0024285 A1 | 2/2004 | Muckter |
| 2004/0040715 A1 | 3/2004 | Wellington et al. |
| 2004/0097782 A1 | 5/2004 | Korakianitis et al. |
| 2004/0097783 A1 | 5/2004 | Peters et al. |
| 2004/0228724 A1 | 11/2004 | Capone et al. |
| 2004/0249363 A1 | 12/2004 | Burke et al. |
| 2005/0010077 A1 | 1/2005 | Calderon |
| 2005/0043805 A1 | 2/2005 | Chudik |
| 2005/0049696 A1* | 3/2005 | Siess ............... A61F 2/2433 623/2.11 |
| 2005/0060036 A1 | 3/2005 | Schultz et al. |
| 2005/0113632 A1 | 5/2005 | Ortiz et al. |
| 2005/0119599 A1 | 6/2005 | Kanz et al. |
| 2005/0187616 A1 | 8/2005 | Realyvasquez |
| 2005/0209617 A1 | 9/2005 | Koven et al. |
| 2005/0220636 A1 | 10/2005 | Henein et al. |
| 2005/0254976 A1 | 11/2005 | Carrier et al. |
| 2005/0256540 A1 | 11/2005 | Silver et al. |
| 2006/0111641 A1 | 5/2006 | Manera et al. |
| 2006/0116700 A1 | 6/2006 | Crow |
| 2006/0129082 A1 | 6/2006 | Rozga |
| 2006/0155158 A1 | 7/2006 | Aboul Hosn |
| 2006/0177343 A1 | 8/2006 | Brian et al. |
| 2006/0195098 A1 | 8/2006 | Schumacher |
| 2006/0257355 A1 | 11/2006 | Stewart et al. |
| 2006/0293664 A1 | 12/2006 | Schumacher |
| 2007/0106274 A1 | 5/2007 | Ayre et al. |
| 2007/0167091 A1 | 7/2007 | Schumacher |
| 2007/0203453 A1 | 8/2007 | Mori et al. |
| 2007/0213690 A1 | 9/2007 | Phillips et al. |
| 2007/0265673 A1 | 11/2007 | Ransbury et al. |
| 2007/0270633 A1 | 11/2007 | Cook et al. |
| 2007/0299314 A1 | 12/2007 | Bertolero et al. |
| 2008/0045779 A1 | 2/2008 | Rinaldi et al. |
| 2008/0065014 A1 | 3/2008 | Von Oepen et al. |
| 2008/0076101 A1 | 3/2008 | Hyde et al. |
| 2008/0097273 A1 | 4/2008 | Levin et al. |
| 2008/0097562 A1 | 4/2008 | Tan |
| 2008/0119421 A1 | 5/2008 | Tuszynski et al. |
| 2008/0132748 A1 | 6/2008 | Shifflette |
| 2008/0132749 A1 | 6/2008 | Hegde et al. |
| 2008/0167711 A1 | 7/2008 | Roorda |
| 2008/0188923 A1 | 8/2008 | Chu |
| 2008/0200750 A1 | 8/2008 | James |
| 2008/0208329 A1 | 8/2008 | Bishop et al. |
| 2008/0228026 A1 | 9/2008 | Manera et al. |
| 2008/0240947 A1 | 10/2008 | Allaire et al. |
| 2008/0243030 A1 | 10/2008 | Seibel et al. |
| 2008/0275295 A1 | 11/2008 | Gertner |
| 2008/0275354 A1 | 11/2008 | Thuramalla et al. |
| 2008/0296433 A1 | 12/2008 | Brenner et al. |
| 2008/0300677 A1 | 12/2008 | Schrayer |
| 2009/0063402 A1 | 3/2009 | Hayter |
| 2009/0143635 A1 | 6/2009 | Benkowski et al. |
| 2009/0171448 A1 | 7/2009 | Eli |
| 2009/0177028 A1 | 7/2009 | White |
| 2009/0182307 A1 | 7/2009 | Yap et al. |
| 2009/0188964 A1 | 7/2009 | Orlov |
| 2009/0259089 A1 | 10/2009 | Gelbart et al. |
| 2010/0016703 A1 | 1/2010 | Batkin et al. |
| 2010/0022943 A1 | 1/2010 | Mauch et al. |
| 2010/0076380 A1 | 3/2010 | Hui |
| 2010/0084326 A1 | 4/2010 | Takesawa |
| 2010/0087742 A1 | 4/2010 | Bishop et al. |
| 2010/0105978 A1 | 4/2010 | Matsui et al. |
| 2010/0152523 A1 | 6/2010 | MacDonald et al. |
| 2010/0152525 A1 | 6/2010 | Weizman et al. |
| 2010/0152526 A1 | 6/2010 | Pacella et al. |
| 2010/0160751 A1 | 6/2010 | Hete et al. |
| 2010/0185220 A1 | 7/2010 | Naghavi et al. |
| 2010/0222635 A1 | 9/2010 | Poirier |
| 2010/0222878 A1 | 9/2010 | Poirier |
| 2010/0249489 A1 | 9/2010 | Jarvik |
| 2011/0098548 A1 | 4/2011 | Budiman et al. |
| 2011/0152999 A1* | 6/2011 | Hastings ............... A61M 60/40 623/1.15 |
| 2011/0178596 A1 | 7/2011 | Hauck et al. |
| 2011/0224655 A1 | 9/2011 | Asirvatham et al. |
| 2011/0301625 A1 | 12/2011 | Mauch et al. |
| 2011/0304240 A1 | 12/2011 | Meitav et al. |
| 2012/0022316 A1 | 1/2012 | Aboul-Hosn et al. |
| 2012/0028908 A1 | 2/2012 | Viswanath et al. |
| 2012/0039711 A1 | 2/2012 | Roehn |

(56) References Cited

U.S. PATENT DOCUMENTS

| | | |
|---|---|---|
| 2012/0109060 A1 | 5/2012 | Kick et al. |
| 2012/0165641 A1 | 6/2012 | Burnett et al. |
| 2012/0172655 A1* | 7/2012 | Campbell ............. A61M 25/04 600/16 |
| 2012/0179184 A1 | 7/2012 | Orlov |
| 2012/0184803 A1 | 7/2012 | Simon et al. |
| 2012/0190918 A1 | 7/2012 | Oepen et al. |
| 2012/0239139 A1 | 9/2012 | Wnendt et al. |
| 2012/0252709 A1 | 10/2012 | Felts et al. |
| 2012/0302458 A1 | 11/2012 | Adamczyk et al. |
| 2012/0316586 A1 | 12/2012 | Demarais et al. |
| 2012/0330683 A1 | 12/2012 | Ledwidge et al. |
| 2013/0023373 A1 | 1/2013 | Janek |
| 2013/0040407 A1 | 2/2013 | Brophy et al. |
| 2013/0053693 A1 | 2/2013 | Breznock et al. |
| 2013/0144144 A1 | 6/2013 | Laster et al. |
| 2013/0211489 A1 | 8/2013 | Makower et al. |
| 2013/0233798 A1 | 9/2013 | Wiktor et al. |
| 2013/0245360 A1 | 9/2013 | Schumacher |
| 2013/0267892 A1 | 10/2013 | Woolford |
| 2013/0281761 A1 | 10/2013 | Kapur |
| 2013/0303831 A1* | 11/2013 | Evans .................. A61M 1/101 600/16 |
| 2013/0310845 A1 | 11/2013 | Thor et al. |
| 2013/0317604 A1 | 11/2013 | Min et al. |
| 2013/0344047 A1 | 12/2013 | Pacetti et al. |
| 2014/0017200 A1 | 1/2014 | Michal et al. |
| 2014/0039465 A1 | 2/2014 | Schulz et al. |
| 2014/0039603 A1 | 2/2014 | Wang |
| 2014/0051908 A1 | 2/2014 | Khanal et al. |
| 2014/0058190 A1 | 2/2014 | Gohean et al. |
| 2014/0066693 A1 | 3/2014 | Goldfarb et al. |
| 2014/0128659 A1 | 5/2014 | Heuring et al. |
| 2014/0128795 A1 | 5/2014 | Keren et al. |
| 2014/0163664 A1 | 6/2014 | Goldsmith |
| 2014/0190523 A1 | 7/2014 | Garvey et al. |
| 2014/0194678 A1 | 7/2014 | Wildhirt et al. |
| 2014/0194717 A1 | 7/2014 | Wildhirt et al. |
| 2014/0199377 A1 | 7/2014 | Stankus et al. |
| 2014/0200655 A1 | 7/2014 | Webler et al. |
| 2014/0207232 A1 | 7/2014 | Garrigue |
| 2014/0228741 A1 | 8/2014 | Frankowski et al. |
| 2014/0243970 A1 | 8/2014 | Yanai |
| 2014/0255176 A1 | 9/2014 | Bredenbreuker et al. |
| 2014/0275721 A1 | 9/2014 | Yanai et al. |
| 2014/0275725 A1 | 9/2014 | Schenck et al. |
| 2014/0288354 A1 | 9/2014 | Timms et al. |
| 2014/0309481 A1 | 10/2014 | Medvedev et al. |
| 2014/0336444 A1 | 11/2014 | Bonde |
| 2014/0336486 A1 | 11/2014 | Ouyang et al. |
| 2014/0336747 A1 | 11/2014 | Rapoza et al. |
| 2014/0341726 A1 | 11/2014 | Wu et al. |
| 2014/0350328 A1 | 11/2014 | Mohl |
| 2014/0357938 A1 | 12/2014 | Pilla et al. |
| 2014/0370073 A1 | 12/2014 | Tang et al. |
| 2015/0005571 A1 | 1/2015 | Jeffery et al. |
| 2015/0018747 A1 | 1/2015 | Michal et al. |
| 2015/0031938 A1 | 1/2015 | Crosby et al. |
| 2015/0051437 A1 | 2/2015 | Miyakoshi et al. |
| 2015/0068069 A1 | 3/2015 | Tran et al. |
| 2015/0080639 A1 | 3/2015 | Radziemski et al. |
| 2015/0080743 A1 | 3/2015 | Siess |
| 2015/0087890 A1 | 3/2015 | Spanier et al. |
| 2015/0112210 A1 | 4/2015 | Webler |
| 2015/0120323 A1 | 4/2015 | Galasso et al. |
| 2015/0134048 A1 | 5/2015 | Ding |
| 2015/0152878 A1 | 6/2015 | McBride et al. |
| 2015/0159643 A1 | 6/2015 | Koob |
| 2015/0174060 A1 | 6/2015 | Heit et al. |
| 2015/0191607 A1 | 7/2015 | McDaniel |
| 2015/0207331 A1 | 7/2015 | Petersen |
| 2015/0216685 A1 | 8/2015 | Spence et al. |
| 2015/0222128 A1 | 8/2015 | Hansen |
| 2015/0222139 A1 | 8/2015 | Petersen et al. |
| 2015/0226691 A1 | 8/2015 | Wang et al. |
| 2015/0230709 A1 | 8/2015 | Milner et al. |
| 2015/0231317 A1 | 8/2015 | Schima et al. |
| 2015/0238671 A1 | 8/2015 | Mesallum |
| 2015/0265757 A1 | 9/2015 | Dowling et al. |
| 2015/0283027 A1 | 10/2015 | Lampe et al. |
| 2015/0285258 A1 | 10/2015 | Foster |
| 2015/0290370 A1 | 10/2015 | Crunkleton et al. |
| 2015/0290377 A1 | 10/2015 | Kearsley et al. |
| 2015/0306291 A1 | 10/2015 | Bonde et al. |
| 2015/0320926 A1 | 11/2015 | Fitzpatrick et al. |
| 2015/0328382 A1 | 11/2015 | Corbett et al. |
| 2015/0364861 A1 | 12/2015 | Lucke et al. |
| 2015/0366495 A1 | 12/2015 | Gable, III et al. |
| 2015/0367050 A1 | 12/2015 | Bulent et al. |
| 2015/0368335 A1 | 12/2015 | Banerjee et al. |
| 2015/0374892 A1 | 12/2015 | Yanai et al. |
| 2016/0022887 A1 | 1/2016 | Wampler |
| 2016/0030649 A1 | 2/2016 | Zeng |
| 2016/0038315 A1 | 2/2016 | Consigny et al. |
| 2016/0045098 A1 | 2/2016 | Tsubouchi |
| 2016/0045652 A1 | 2/2016 | Cornen |
| 2016/0045654 A1 | 2/2016 | Connor |
| 2016/0058434 A1 | 3/2016 | Delaloye et al. |
| 2016/0067395 A1 | 3/2016 | Jimenez et al. |
| 2016/0085714 A1 | 3/2016 | Goodnow et al. |
| 2016/0175044 A1 | 6/2016 | Abunassar et al. |
| 2016/0182158 A1 | 6/2016 | Lee et al. |
| 2016/0184499 A1 | 6/2016 | Ricci et al. |
| 2016/0199556 A1 | 7/2016 | Ayre et al. |
| 2016/0199557 A1 | 7/2016 | Bluvshtein et al. |
| 2016/0203275 A1 | 7/2016 | Benjamin et al. |
| 2016/0220269 A1 | 8/2016 | Labropoulos et al. |
| 2016/0220785 A1 | 8/2016 | Fabro |
| 2016/0222969 A1 | 8/2016 | Heide et al. |
| 2016/0250399 A1 | 9/2016 | Tiller et al. |
| 2016/0250400 A1 | 9/2016 | Schumacher |
| 2016/0251720 A1 | 9/2016 | Schulze et al. |
| 2016/0256619 A1* | 9/2016 | Throckmorton .... A61M 1/1006 |
| 2016/0256620 A1 | 9/2016 | Scheckel et al. |
| 2016/0263299 A1 | 9/2016 | Xu et al. |
| 2016/0271161 A1 | 9/2016 | Dobson |
| 2016/0271309 A1 | 9/2016 | Throckmorton et al. |
| 2016/0279310 A1 | 9/2016 | Scheckel et al. |
| 2016/0303301 A1 | 10/2016 | Bluvshtein et al. |
| 2016/0308403 A1 | 10/2016 | Bluvshtein et al. |
| 2016/0317291 A1 | 11/2016 | Bishop et al. |
| 2016/0317333 A1 | 11/2016 | Ainsworth et al. |
| 2016/0325034 A1 | 11/2016 | Wiktor et al. |
| 2016/0348688 A1 | 12/2016 | Schumacher et al. |
| 2016/0354526 A1 | 12/2016 | Whisenant et al. |
| 2016/0375187 A1 | 12/2016 | Lee et al. |
| 2017/0000361 A1 | 1/2017 | Meyering et al. |
| 2017/0000935 A1 | 1/2017 | Vasilyev et al. |
| 2017/0007552 A1 | 1/2017 | Slepian |
| 2017/0007762 A1 | 1/2017 | Hayter et al. |
| 2017/0014401 A1 | 1/2017 | Dalton et al. |
| 2017/0021074 A1 | 1/2017 | Opfermann et al. |
| 2017/0028114 A1 | 2/2017 | Göllner et al. |
| 2017/0028115 A1 | 2/2017 | Muller |
| 2017/0035952 A1* | 2/2017 | Muller ................ A61M 1/1008 |
| 2017/0035954 A1 | 2/2017 | Muller et al. |
| 2017/0043076 A1 | 2/2017 | Wampler et al. |
| 2017/0063143 A1 | 3/2017 | Hoarau et al. |
| 2017/0080136 A1 | 3/2017 | Janeczek et al. |
| 2017/0100527 A1 | 4/2017 | Schwammenthal et al. |
| 2017/0112984 A1 | 4/2017 | Fonseca |
| 2017/0119946 A1 | 5/2017 | McChrystal et al. |
| 2017/0136165 A1 | 5/2017 | Hansen et al. |
| 2017/0136225 A1 | 5/2017 | Siess et al. |
| 2017/0143883 A1 | 5/2017 | Spence |
| 2017/0143952 A1 | 5/2017 | Siess et al. |
| 2017/0157309 A1 | 6/2017 | Begg et al. |
| 2017/0193184 A1 | 7/2017 | Hayter et al. |
| 2017/0196638 A1 | 7/2017 | Serna et al. |
| 2017/0202575 A1 | 7/2017 | Stanfield et al. |
| 2017/0215918 A1 | 8/2017 | Tao et al. |
| 2017/0224896 A1 | 8/2017 | Graham et al. |
| 2017/0232168 A1 | 8/2017 | Reichenbach et al. |
| 2017/0232169 A1 | 8/2017 | Muller |

(56) References Cited

U.S. PATENT DOCUMENTS

| | | | |
|---|---|---|---|
| 2017/0232172 A1 | 8/2017 | Mesallum | |
| 2017/0239407 A1 | 8/2017 | Hayward | |
| 2017/0250575 A1 | 8/2017 | Wong et al. | |
| 2017/0265994 A1 | 9/2017 | Krone | |
| 2017/0274128 A1* | 9/2017 | Tamburino | A61M 60/205 |
| 2017/0281025 A9 | 10/2017 | Glover et al. | |
| 2017/0281841 A1 | 10/2017 | Larose et al. | |
| 2017/0281842 A1 | 10/2017 | Larose et al. | |
| 2017/0290964 A1 | 10/2017 | Barry | |
| 2017/0296227 A1 | 10/2017 | Osypka | |
| 2017/0296725 A1 | 10/2017 | Peters et al. | |
| 2017/0312106 A1 | 11/2017 | Gomez et al. | |
| 2017/0312416 A1 | 11/2017 | Strueber | |
| 2017/0312492 A1 | 11/2017 | Fantuzzi et al. | |
| 2017/0319113 A1 | 11/2017 | Hurd et al. | |
| 2017/0323713 A1 | 11/2017 | Moeller et al. | |
| 2017/0325943 A1 | 11/2017 | Robin et al. | |
| 2017/0333607 A1 | 11/2017 | Zarins | |
| 2017/0333673 A1 | 11/2017 | Tuval et al. | |
| 2017/0340789 A1 | 11/2017 | Bonde et al. | |
| 2017/0340790 A1 | 11/2017 | Wiesener et al. | |
| 2017/0360309 A1 | 12/2017 | Moore et al. | |
| 2017/0361001 A1 | 12/2017 | Canatella et al. | |
| 2017/0361011 A1 | 12/2017 | Muennich et al. | |
| 2017/0363103 A1 | 12/2017 | Canatella et al. | |
| 2017/0363210 A1 | 12/2017 | Durst et al. | |
| 2017/0363620 A1 | 12/2017 | Beshiri et al. | |
| 2017/0368246 A1 | 12/2017 | Criscione et al. | |
| 2017/0370365 A1 | 12/2017 | Fritz et al. | |
| 2018/0001003 A1 | 1/2018 | Moran et al. | |
| 2018/0001007 A1 | 1/2018 | Stratton | |
| 2018/0001012 A1 | 1/2018 | Ardehali | |
| 2018/0001062 A1 | 1/2018 | O'Carrol et al. | |
| 2018/0015214 A1 | 1/2018 | Lynch | |
| 2018/0021494 A1 | 1/2018 | Muller et al. | |
| 2018/0021495 A1 | 1/2018 | Muller et al. | |
| 2018/0021497 A1 | 1/2018 | Nunez et al. | |
| 2018/0028736 A1 | 2/2018 | Wong et al. | |
| 2018/0035926 A1 | 2/2018 | Stafford | |
| 2018/0040418 A1 | 2/2018 | Hansen et al. | |
| 2018/0047282 A1 | 2/2018 | He et al. | |
| 2018/0050139 A1 | 2/2018 | Siess et al. | |
| 2018/0050140 A1 | 2/2018 | Siess et al. | |
| 2018/0050142 A1 | 2/2018 | Siess et al. | |
| 2018/0055383 A1 | 3/2018 | Manera | |
| 2018/0055983 A1 | 3/2018 | Bourque | |
| 2018/0058437 A1 | 3/2018 | Eilers et al. | |
| 2018/0064862 A1 | 3/2018 | Keenan et al. | |
| 2018/0071020 A1 | 3/2018 | Laufer et al. | |
| 2018/0078159 A1 | 3/2018 | Edelman et al. | |
| 2018/0085505 A1 | 3/2018 | Casas | |
| 2018/0085507 A1 | 3/2018 | Casas et al. | |
| 2018/0085509 A1 | 3/2018 | Petersen | |
| 2018/0093026 A1 | 4/2018 | Angwin et al. | |
| 2018/0097368 A1 | 4/2018 | Hansen | |
| 2018/0099076 A1 | 4/2018 | Larose | |
| 2018/0099078 A1 | 4/2018 | Tuseth et al. | |
| 2018/0100507 A1 | 4/2018 | Wu et al. | |
| 2018/0103611 A1 | 4/2018 | Mainini et al. | |
| 2018/0103870 A1 | 4/2018 | Limaye et al. | |
| 2018/0108275 A1 | 4/2018 | Newberry et al. | |
| 2018/0110514 A1 | 4/2018 | Hoarau et al. | |
| 2018/0114426 A1 | 4/2018 | Lee | |
| 2018/0133380 A1 | 5/2018 | Liebing | |
| 2018/0140759 A1 | 5/2018 | Kaiser et al. | |
| 2018/0140801 A1 | 5/2018 | Voss et al. | |
| 2018/0146968 A1 | 5/2018 | Nitzan et al. | |
| 2018/0149164 A1 | 5/2018 | Siess | |
| 2018/0149165 A1 | 5/2018 | Siess et al. | |
| 2018/0154051 A1 | 6/2018 | Hossainy et al. | |
| 2018/0154128 A1 | 6/2018 | Woo et al. | |
| 2018/0161540 A1 | 6/2018 | Fantuzzi et al. | |
| 2018/0161555 A1 | 6/2018 | Zhadkevich | |
| 2018/0168469 A1 | 6/2018 | Granegger | |
| 2018/0169313 A1 | 6/2018 | Schwammenthal et al. | |
| 2018/0193543 A1 | 7/2018 | Sun | |
| 2018/0193614 A1 | 7/2018 | Nitzan et al. | |
| 2018/0193616 A1 | 7/2018 | Nitzan et al. | |
| 2018/0200420 A1 | 7/2018 | Di Paola et al. | |
| 2018/0200422 A1 | 7/2018 | Nguyen et al. | |
| 2018/0202962 A1 | 7/2018 | Simmons et al. | |
| 2018/0207334 A1 | 7/2018 | Siess | |
| 2018/0207337 A1 | 7/2018 | Spence et al. | |
| 2018/0207338 A1 | 7/2018 | Bluvshtein et al. | |
| 2018/0228953 A1 | 8/2018 | Siess et al. | |
| 2018/0228957 A1 | 8/2018 | Colella | |
| 2018/0242891 A1 | 8/2018 | Bernstein et al. | |
| 2018/0242976 A1 | 8/2018 | Kizuka | |
| 2018/0243086 A1 | 8/2018 | Barbarino et al. | |
| 2018/0243488 A1 | 8/2018 | Callaway et al. | |
| 2018/0243489 A1 | 8/2018 | Haddadi | |
| 2018/0243490 A1 | 8/2018 | Kallenbach et al. | |
| 2018/0243492 A1 | 8/2018 | Salys | |
| 2018/0250457 A1 | 9/2018 | Morello et al. | |
| 2018/0250458 A1 | 9/2018 | Petersen et al. | |
| 2018/0256242 A1 | 9/2018 | Bluvshtein et al. | |
| 2018/0256794 A1 | 9/2018 | Rodefeld | |
| 2018/0256795 A1 | 9/2018 | Schade et al. | |
| 2018/0256797 A1 | 9/2018 | Schenck et al. | |
| 2018/0256798 A1 | 9/2018 | Botterbusch et al. | |
| 2018/0256859 A1 | 9/2018 | Korkuch | |
| 2018/0264183 A1 | 9/2018 | Jahangir | |
| 2018/0264184 A1 | 9/2018 | Jeffries et al. | |
| 2018/0269692 A1 | 9/2018 | Petersen et al. | |
| 2018/0280598 A1 | 10/2018 | Curran et al. | |
| 2018/0280599 A1 | 10/2018 | Harjes et al. | |
| 2018/0280600 A1 | 10/2018 | Harjes et al. | |
| 2018/0280601 A1 | 10/2018 | Harjes et al. | |
| 2018/0280604 A1 | 10/2018 | Hobro et al. | |
| 2018/0289295 A1 | 10/2018 | Hoss et al. | |
| 2018/0289876 A1 | 10/2018 | Nguyen et al. | |
| 2018/0289877 A1 | 10/2018 | Schumacher et al. | |
| 2018/0296572 A1 | 10/2018 | Deisher | |
| 2019/0143018 A1 | 5/2019 | Salahieh et al. | |
| 2019/0167873 A1 | 6/2019 | Koike et al. | |
| 2019/0269840 A1* | 9/2019 | Tuval | A61M 1/125 |
| 2020/0029951 A1 | 1/2020 | Bessler et al. | |
| 2020/0114053 A1 | 4/2020 | Salahieh et al. | |
| 2021/0008261 A1 | 1/2021 | Calomeni et al. | |
| 2021/0023285 A1 | 1/2021 | Brandt | |

FOREIGN PATENT DOCUMENTS

| | | |
|---|---|---|
| CN | 1008307 B | 6/1990 |
| CN | 1053108 A | 7/1991 |
| CN | 1105103 A | 7/1995 |
| CN | 1146329 A | 4/1997 |
| CN | 1179708 A | 4/1998 |
| CN | 2326258 Y | 6/1999 |
| CN | 1222862 A | 7/1999 |
| CN | 1045058 C | 9/1999 |
| CN | 1235849 A | 11/1999 |
| CN | 2361290 Y | 2/2000 |
| CN | 1254598 A | 5/2000 |
| CN | 2386827 Y | 7/2000 |
| CN | 2412579 Y | 1/2001 |
| CN | 2417173 Y | 1/2001 |
| CN | 1310647 A | 8/2001 |
| CN | 1342497 A | 4/2002 |
| CN | 1088795 C | 8/2002 |
| CN | 2504815 Y | 8/2002 |
| CN | 1376523 A | 10/2002 |
| CN | 1097138 C | 12/2002 |
| CN | 1105581 C | 4/2003 |
| CN | 1421248 A | 6/2003 |
| CN | 2558386 Y | 7/2003 |
| CN | 1118304 C | 8/2003 |
| CN | 1436048 A | 8/2003 |
| CN | 1120729 C | 9/2003 |
| CN | 2574609 Y | 9/2003 |
| CN | 1140228 C | 3/2004 |
| CN | 1161581 C | 8/2004 |
| CN | 1167472 C | 9/2004 |
| CN | 1527906 A | 9/2004 |

(56) References Cited

FOREIGN PATENT DOCUMENTS

| | | | |
|---|---|---|---|
| CN | 1559361 | A | 1/2005 |
| CN | 1559626 | A | 1/2005 |
| CN | 1572331 | A | 2/2005 |
| CN | 1202871 | C | 5/2005 |
| CN | 1679974 | A | 10/2005 |
| CN | 1694338 | A | 11/2005 |
| CN | 1705462 | A | 12/2005 |
| CN | 1239133 | C | 2/2006 |
| CN | 1239209 | C | 2/2006 |
| CN | 2754637 | Y | 2/2006 |
| CN | 1244381 | C | 3/2006 |
| CN | 1249339 | C | 4/2006 |
| CN | 2776418 | Y | 5/2006 |
| CN | 2787222 | Y | 6/2006 |
| CN | 1799652 | A | 7/2006 |
| CN | 1806774 | A | 7/2006 |
| CN | 1826463 | A | 8/2006 |
| CN | 1833735 | A | 9/2006 |
| CN | 1833736 | A | 9/2006 |
| CN | 2831716 | Y | 10/2006 |
| CN | 1874805 | A | 12/2006 |
| CN | 1301583 | C | 2/2007 |
| CN | 1921947 | A | 2/2007 |
| CN | 2880096 | Y | 3/2007 |
| CN | 2899800 | Y | 5/2007 |
| CN | 101001765 | A | 7/2007 |
| CN | 1329666 | C | 8/2007 |
| CN | 101024098 | A | 8/2007 |
| CN | 101031302 | A | 9/2007 |
| CN | 101112628 | A | 1/2008 |
| CN | 101121045 | A | 2/2008 |
| CN | 101124002 | A | 2/2008 |
| CN | 101132830 | A | 2/2008 |
| CN | 100382855 | C | 4/2008 |
| CN | 101256992 | A | 9/2008 |
| CN | 100429406 | C | 10/2008 |
| CN | 100439717 | C | 12/2008 |
| CN | 100472042 | C | 3/2009 |
| CN | 201208423 | Y | 3/2009 |
| CN | 100488577 | C | 5/2009 |
| CN | 201230980 | Y | 5/2009 |
| CN | 201239369 | Y | 5/2009 |
| CN | 201246310 | Y | 5/2009 |
| CN | 101522115 | A | 9/2009 |
| CN | 101534883 | A | 9/2009 |
| CN | 201308666 | Y | 9/2009 |
| CN | 101563605 | A | 10/2009 |
| CN | 100558416 | C | 11/2009 |
| CN | 100566765 | C | 12/2009 |
| CN | 101595276 | A | 12/2009 |
| CN | 101631578 | A | 1/2010 |
| CN | 101652069 | A | 2/2010 |
| CN | 101678025 | A | 3/2010 |
| CN | 101687791 | A | 3/2010 |
| CN | 101244296 | B | 6/2010 |
| CN | 101730552 | A | 6/2010 |
| CN | 101208058 | B | 8/2010 |
| CN | 101808515 | A | 8/2010 |
| CN | 101401981 | B | 9/2010 |
| CN | 101843528 | A | 9/2010 |
| CN | 101232952 | B | 11/2010 |
| CN | 101361994 | B | 11/2010 |
| CN | 201618200 | U | 11/2010 |
| CN | 201710717 | U | 1/2011 |
| CN | 101417155 | B | 2/2011 |
| CN | 101581307 | B | 4/2011 |
| CN | 102065923 | A | 5/2011 |
| CN | 101269245 | B | 7/2011 |
| CN | 101618240 | B | 8/2011 |
| CN | 102166379 | A | 8/2011 |
| CN | 101484093 | B | 9/2011 |
| CN | 102292053 | A | 12/2011 |
| CN | 102422018 | A | 4/2012 |
| CN | 102438673 | A | 5/2012 |
| CN | 102475923 | A | 5/2012 |
| CN | 202218993 | U | 5/2012 |
| CN | 101983732 | B | 7/2012 |
| CN | 102553005 | A | 7/2012 |
| CN | 101590295 | B | 8/2012 |
| CN | 101822854 | B | 9/2012 |
| CN | 101822855 | B | 9/2012 |
| CN | 101189431 | B | 10/2012 |
| CN | 101810891 | B | 10/2012 |
| CN | 102711894 | A | 10/2012 |
| CN | 102869318 | A | 1/2013 |
| CN | 102088920 | B | 4/2013 |
| CN | 103026234 | A | 4/2013 |
| CN | 103068417 | A | 4/2013 |
| CN | 103172739 | A | 6/2013 |
| CN | 101420993 | B | 7/2013 |
| CN | 103206402 | A | 7/2013 |
| CN | 103228300 | A | 7/2013 |
| CN | 103356306 | A | 10/2013 |
| CN | 103381277 | A | 11/2013 |
| CN | 103432637 | A | 12/2013 |
| CN | 103437951 | A | 12/2013 |
| CN | 103446635 | A | 12/2013 |
| CN | 103458832 | A | 12/2013 |
| CN | 102319457 | B | 1/2014 |
| CN | 103509116 | A | 1/2014 |
| CN | 103541857 | A | 1/2014 |
| CN | 103635212 | A | 3/2014 |
| CN | 203507200 | U | 4/2014 |
| CN | 203539803 | U | 4/2014 |
| CN | 203591299 | U | 5/2014 |
| CN | 102317629 | B | 8/2014 |
| CN | 203756589 | U | 8/2014 |
| CN | 104043153 | A | 9/2014 |
| CN | 203829160 | U | 9/2014 |
| CN | 104105511 | A | 10/2014 |
| CN | 203935281 | U | 11/2014 |
| CN | 104208763 | A | 12/2014 |
| CN | 203971002 | U | 12/2014 |
| CN | 204050452 | U | 12/2014 |
| CN | 102271728 | B | 1/2015 |
| CN | 102294057 | B | 1/2015 |
| CN | 104271075 | A | 1/2015 |
| CN | 102588255 | B | 3/2015 |
| CN | 104470454 | A | 3/2015 |
| CN | 102300501 | B | 4/2015 |
| CN | 103055363 | B | 4/2015 |
| CN | 104473676 | A | 4/2015 |
| CN | 104524663 | A | 4/2015 |
| CN | 204293210 | U | 4/2015 |
| CN | 102686316 | B | 5/2015 |
| CN | 104586469 | A | 5/2015 |
| CN | 104602987 | A | 5/2015 |
| CN | 102458275 | B | 6/2015 |
| CN | 102458498 | B | 6/2015 |
| CN | 104684607 | A | 6/2015 |
| CN | 104721899 | A | 6/2015 |
| CN | 204419151 | U | 6/2015 |
| CN | 102397598 | B | 7/2015 |
| CN | 103446634 | B | 7/2015 |
| CN | 104758029 | A | 7/2015 |
| CN | 104771797 | A | 7/2015 |
| CN | 101868628 | B | 8/2015 |
| CN | 102665784 | B | 8/2015 |
| CN | 103706018 | B | 9/2015 |
| CN | 104955420 | A | 9/2015 |
| CN | 104984425 | A | 10/2015 |
| CN | 104997550 | A | 10/2015 |
| CN | 105007960 | A | 10/2015 |
| CN | 105142719 | A | 12/2015 |
| CN | 105208927 | A | 12/2015 |
| CN | 102176933 | B | 1/2016 |
| CN | 102947092 | B | 1/2016 |
| CN | 103717837 | B | 1/2016 |
| CN | 105228688 | A | 1/2016 |
| CN | 105283149 | A | 1/2016 |
| CN | 204972635 | U | 1/2016 |
| CN | 103228232 | B | 2/2016 |
| CN | 103355925 | B | 2/2016 |
| CN | 105311692 | A | 2/2016 |

(56) References Cited

FOREIGN PATENT DOCUMENTS

| | | | |
|---|---|---|---|
| CN | 102257279 B | 3/2016 |
| CN | 102472719 B | 3/2016 |
| CN | 103154738 B | 3/2016 |
| CN | 105451787 A | 3/2016 |
| CN | 205083494 U | 3/2016 |
| CN | 103850979 B | 4/2016 |
| CN | 105477706 A | 4/2016 |
| CN | 105517589 A | 4/2016 |
| CN | 205163763 U | 4/2016 |
| CN | 103002833 B | 5/2016 |
| CN | 103861163 B | 5/2016 |
| CN | 105555204 A | 5/2016 |
| CN | 205215814 U | 5/2016 |
| CN | 102940911 B | 6/2016 |
| CN | 105641762 A | 6/2016 |
| CN | 105641763 A | 6/2016 |
| CN | 105662439 A | 6/2016 |
| CN | 105709287 A | 6/2016 |
| CN | 105722477 A | 6/2016 |
| CN | 205322884 U | 6/2016 |
| CN | 104069555 B | 7/2016 |
| CN | 105744915 A | 7/2016 |
| CN | 105790453 A | 7/2016 |
| CN | 105792780 A | 7/2016 |
| CN | 105792864 A | 7/2016 |
| CN | 103260666 B | 8/2016 |
| CN | 103732171 B | 8/2016 |
| CN | 103928971 B | 8/2016 |
| CN | 105833370 A | 8/2016 |
| CN | 205411785 U | 8/2016 |
| CN | 205460099 U | 8/2016 |
| CN | 205528886 U | 8/2016 |
| CN | 103889369 B | 9/2016 |
| CN | 104849482 B | 9/2016 |
| CN | 105980660 A | 9/2016 |
| CN | 106075621 A | 11/2016 |
| CN | 106102657 A | 11/2016 |
| CN | 205681272 U | 11/2016 |
| CN | 205698666 U | 11/2016 |
| CN | 205698725 U | 11/2016 |
| CN | 205753678 U | 11/2016 |
| CN | 106214288 A | 12/2016 |
| CN | 106256321 A | 12/2016 |
| CN | 205779766 U | 12/2016 |
| CN | 106334224 A | 1/2017 |
| CN | 205867186 U | 1/2017 |
| CN | 205876589 U | 1/2017 |
| CN | 103281971 B | 2/2017 |
| CN | 106390218 A | 2/2017 |
| CN | 103533970 B | 3/2017 |
| CN | 104826183 B | 3/2017 |
| CN | 106512117 A | 3/2017 |
| CN | 106581840 A | 4/2017 |
| CN | 104068947 B | 5/2017 |
| CN | 106620912 A | 5/2017 |
| CN | 106691363 A | 5/2017 |
| CN | 106716137 A | 5/2017 |
| CN | 106794293 A | 5/2017 |
| CN | 104225696 B | 6/2017 |
| CN | 104918578 B | 6/2017 |
| CN | 105915005 B | 6/2017 |
| CN | 106902404 A | 6/2017 |
| CN | 206325049 U | 7/2017 |
| CN | 206355093 U | 7/2017 |
| CN | 105377321 B | 8/2017 |
| CN | 107050543 A | 8/2017 |
| CN | 107050544 A | 8/2017 |
| CN | 107080870 A | 8/2017 |
| CN | 107080871 A | 8/2017 |
| CN | 107110875 A | 8/2017 |
| CN | 206414547 U | 8/2017 |
| CN | 206443963 U | 8/2017 |
| CN | 103930214 B | 9/2017 |
| CN | 104619361 B | 9/2017 |
| CN | 104936550 B | 9/2017 |
| CN | 105188618 B | 9/2017 |
| CN | 107115162 A | 9/2017 |
| CN | 107126588 A | 9/2017 |
| CN | 107134208 A | 9/2017 |
| CN | 107157623 A | 9/2017 |
| CN | 103857363 B | 10/2017 |
| CN | 104768500 B | 10/2017 |
| CN | 105008841 B | 10/2017 |
| CN | 105492036 B | 10/2017 |
| CN | 107252339 A | 10/2017 |
| CN | 107281567 A | 10/2017 |
| CN | 206592332 U | 10/2017 |
| CN | 107349484 A | 11/2017 |
| CN | 206660203 U | 11/2017 |
| CN | 105287050 B | 12/2017 |
| CN | 105597172 B | 12/2017 |
| CN | 105854097 B | 12/2017 |
| CN | 107412892 A | 12/2017 |
| CN | 107440681 A | 12/2017 |
| CN | 107496054 A | 12/2017 |
| CN | 104602647 B | 1/2018 |
| CN | 106061523 B | 1/2018 |
| CN | 107551341 A | 1/2018 |
| CN | 206934393 U | 1/2018 |
| CN | 107693868 A | 2/2018 |
| CN | 107693869 A | 2/2018 |
| CN | 107708765 A | 2/2018 |
| CN | 207018256 U | 2/2018 |
| CN | 106029120 B | 3/2018 |
| CN | 107753153 A | 3/2018 |
| CN | 107754071 A | 3/2018 |
| CN | 107798980 A | 3/2018 |
| CN | 107835826 A | 3/2018 |
| CN | 107837430 A | 3/2018 |
| CN | 107862963 A | 3/2018 |
| CN | 207125933 U | 3/2018 |
| CN | 207136890 U | 3/2018 |
| CN | 105120796 B | 4/2018 |
| CN | 105214153 B | 4/2018 |
| CN | 107865988 A | 4/2018 |
| CN | 107886825 A | 4/2018 |
| CN | 107913442 A | 4/2018 |
| CN | 107921195 A | 4/2018 |
| CN | 107923311 A | 4/2018 |
| CN | 108025120 A | 5/2018 |
| CN | 108025123 A | 5/2018 |
| CN | 108066834 A | 5/2018 |
| CN | 207410652 U | 5/2018 |
| CN | 104470579 B | 6/2018 |
| CN | 105188604 B | 6/2018 |
| CN | 105492909 B | 6/2018 |
| CN | 105498002 B | 6/2018 |
| CN | 106535824 B | 6/2018 |
| CN | 108136110 A | 6/2018 |
| CN | 108144146 A | 6/2018 |
| CN | 108175884 A | 6/2018 |
| CN | 106028807 B | 7/2018 |
| CN | 106310410 B | 7/2018 |
| CN | 108273148 A | 7/2018 |
| CN | 108310486 A | 7/2018 |
| CN | 108348667 A | 7/2018 |
| CN | 207614108 U | 7/2018 |
| CN | 105640635 B | 8/2018 |
| CN | 105923112 B | 8/2018 |
| CN | 108367106 A | 8/2018 |
| CN | 108430533 A | 8/2018 |
| CN | 108457844 A | 8/2018 |
| CN | 108472138 A | 8/2018 |
| CN | 108472395 A | 8/2018 |
| CN | 108472424 A | 8/2018 |
| CN | 207708246 U | 8/2018 |
| CN | 207708250 U | 8/2018 |
| CN | 105407937 B | 9/2018 |
| CN | 105902298 B | 9/2018 |
| CN | 106420113 B | 9/2018 |
| CN | 106510902 B | 9/2018 |
| CN | 108525039 A | 9/2018 |
| CN | 108525040 A | 9/2018 |
| CN | 108601653 A | 9/2018 |

(56) References Cited

FOREIGN PATENT DOCUMENTS

| | | | |
|---|---|---|---|
| CN | 108601872 A | 9/2018 |
| CN | 108601874 A | 9/2018 |
| CN | 108601875 A | 9/2018 |
| CN | 207924984 U | 9/2018 |
| CN | 106377810 B | 10/2018 |
| EP | 96495 B1 | 9/1986 |
| EP | 79373 B1 | 12/1986 |
| EP | 54049 B1 | 1/1988 |
| EP | 292510 A4 | 8/1989 |
| EP | 167562 B1 | 4/1990 |
| EP | 230532 B1 | 9/1990 |
| EP | 241950 B1 | 12/1990 |
| EP | 129779 B1 | 4/1991 |
| EP | 202649 B1 | 8/1991 |
| EP | 445782 A1 | 9/1991 |
| EP | 464714 A1 | 1/1992 |
| EP | 293592 B1 | 11/1992 |
| EP | 297723 B1 | 8/1993 |
| EP | 396575 B1 | 3/1994 |
| EP | 397668 B1 | 3/1994 |
| EP | 593574 A1 | 4/1994 |
| EP | 378251 B1 | 6/1994 |
| EP | 605621 A1 | 7/1994 |
| EP | 467999 B1 | 8/1994 |
| EP | 350282 B1 | 11/1994 |
| EP | 478635 B1 | 12/1994 |
| EP | 397720 B1 | 3/1995 |
| EP | 421558 B1 | 4/1995 |
| EP | 364799 B1 | 5/1995 |
| EP | 660726 A1 | 7/1995 |
| EP | 672386 A1 | 9/1995 |
| EP | 349581 B1 | 1/1996 |
| EP | 464973 B1 | 1/1996 |
| EP | 505270 B1 | 1/1996 |
| EP | 480101 B1 | 5/1996 |
| EP | 583781 B1 | 5/1996 |
| EP | 583012 B1 | 7/1996 |
| EP | 756500 A1 | 2/1997 |
| EP | 767318 A2 | 4/1997 |
| EP | 788808 A2 | 8/1997 |
| EP | 799060 A1 | 10/1997 |
| EP | 823567 A1 | 2/1998 |
| EP | 832357 A1 | 4/1998 |
| EP | 841917 A1 | 5/1998 |
| EP | 560000 B1 | 9/1998 |
| EP | 879012 A1 | 11/1998 |
| EP | 925078 A1 | 6/1999 |
| EP | 807141 B1 | 7/1999 |
| EP | 681654 B1 | 9/1999 |
| EP | 958066 A1 | 11/1999 |
| EP | 964718 A1 | 12/1999 |
| EP | 725657 B1 | 2/2000 |
| EP | 986409 A1 | 3/2000 |
| EP | 1007140 A1 | 6/2000 |
| EP | 1009466 A1 | 6/2000 |
| EP | 1027898 A1 | 8/2000 |
| EP | 1032437 A1 | 9/2000 |
| EP | 1045708 A1 | 10/2000 |
| EP | 1059885 A2 | 12/2000 |
| EP | 746712 B1 | 10/2001 |
| EP | 1139862 A1 | 10/2001 |
| EP | 1147317 A1 | 10/2001 |
| EP | 1148900 A1 | 10/2001 |
| EP | 699447 B1 | 11/2001 |
| EP | 591896 B1 | 2/2002 |
| EP | 731664 B1 | 2/2002 |
| EP | 797734 B1 | 2/2002 |
| EP | 1217954 A1 | 7/2002 |
| EP | 1231981 A1 | 8/2002 |
| EP | 950057 B1 | 11/2002 |
| EP | 751769 B1 | 1/2003 |
| EP | 1278461 A1 | 1/2003 |
| EP | 860046 B1 | 2/2003 |
| EP | 597881 B2 | 3/2003 |
| EP | 732949 B1 | 3/2003 |
| EP | 814701 B1 | 4/2003 |
| EP | 898479 B1 | 5/2003 |
| EP | 905379 B1 | 5/2003 |
| EP | 655625 B1 | 7/2003 |
| EP | 764448 B1 | 7/2003 |
| EP | 768091 B1 | 7/2003 |
| EP | 825888 B1 | 12/2003 |
| EP | 1379197 A1 | 1/2004 |
| EP | 1382366 A1 | 1/2004 |
| EP | 868145 B1 | 2/2004 |
| EP | 895480 B1 | 5/2004 |
| EP | 1441777 A2 | 8/2004 |
| EP | 916359 B1 | 9/2004 |
| EP | 1482999 A1 | 12/2004 |
| EP | 1291027 B1 | 3/2005 |
| EP | 877633 B1 | 7/2005 |
| EP | 611228 B2 | 8/2005 |
| EP | 1212516 B1 | 10/2005 |
| EP | 1597457 A2 | 11/2005 |
| EP | 1261385 B1 | 2/2006 |
| EP | 1648309 A1 | 4/2006 |
| EP | 1354606 B1 | 6/2006 |
| EP | 1663081 A1 | 6/2006 |
| EP | 1321166 B1 | 7/2006 |
| EP | 1191956 B1 | 9/2006 |
| EP | 1722767 A2 | 11/2006 |
| EP | 1070510 B1 | 1/2007 |
| EP | 1317295 B1 | 1/2007 |
| EP | 1327455 B1 | 1/2007 |
| EP | 1776095 A1 | 4/2007 |
| EP | 1141670 B1 | 7/2007 |
| EP | 1807148 A2 | 7/2007 |
| EP | 1827448 A1 | 9/2007 |
| EP | 1374928 B1 | 12/2007 |
| EP | 1877133 A2 | 1/2008 |
| EP | 1379294 B1 | 5/2008 |
| EP | 1930034 A1 | 6/2008 |
| EP | 1318848 B1 | 7/2008 |
| EP | 1356859 B1 | 8/2008 |
| EP | 1955725 A2 | 8/2008 |
| EP | 2058017 A2 | 5/2009 |
| EP | 1731957 B1 | 8/2009 |
| EP | 1173238 B1 | 10/2009 |
| EP | 2043553 B1 | 3/2010 |
| EP | 2158491 A2 | 3/2010 |
| EP | 2178580 A2 | 4/2010 |
| EP | 2182844 A1 | 5/2010 |
| EP | 2194278 A1 | 6/2010 |
| EP | 1471952 B1 | 7/2010 |
| EP | 2207578 A1 | 7/2010 |
| EP | 2216059 A1 | 8/2010 |
| EP | 2218469 A1 | 8/2010 |
| EP | 2219699 A1 | 8/2010 |
| EP | 2222635 A2 | 9/2010 |
| EP | 2222788 A1 | 9/2010 |
| EP | 2229965 A1 | 9/2010 |
| EP | 2235204 A1 | 10/2010 |
| EP | 1280581 B1 | 11/2010 |
| EP | 2246078 A1 | 11/2010 |
| EP | 2248544 A1 | 11/2010 |
| EP | 2252337 A1 | 11/2010 |
| EP | 2266640 A1 | 12/2010 |
| EP | 2269670 A1 | 1/2011 |
| EP | 2297583 A2 | 3/2011 |
| EP | 2298371 A1 | 3/2011 |
| EP | 2298372 A1 | 3/2011 |
| EP | 2298373 A1 | 3/2011 |
| EP | 2299119 A1 | 3/2011 |
| EP | 1464348 B1 | 4/2011 |
| EP | 2314330 A1 | 4/2011 |
| EP | 2314331 A1 | 4/2011 |
| EP | 2338539 A1 | 6/2011 |
| EP | 2338540 A1 | 6/2011 |
| EP | 2338541 A1 | 6/2011 |
| EP | 1654027 B1 | 7/2011 |
| EP | 2343091 A1 | 7/2011 |
| EP | 2347778 A1 | 7/2011 |
| EP | 1812094 B1 | 8/2011 |
| EP | 2349385 A1 | 8/2011 |

(56) References Cited

FOREIGN PATENT DOCUMENTS

| | | | |
|---|---|---|---|
| EP | 2353626 | A1 | 8/2011 |
| EP | 2356458 | A1 | 8/2011 |
| EP | 2363157 | A1 | 9/2011 |
| EP | 2366412 | A2 | 9/2011 |
| EP | 1907049 | B1 | 11/2011 |
| EP | 2388027 | A1 | 11/2011 |
| EP | 2388029 | A1 | 11/2011 |
| EP | 2399639 | A1 | 12/2011 |
| EP | 1514571 | B1 | 1/2012 |
| EP | 2407185 | A1 | 1/2012 |
| EP | 2407186 | A1 | 1/2012 |
| EP | 2407187 | A1 | 1/2012 |
| EP | 2422735 | A1 | 2/2012 |
| EP | 2322600 | B1 | 3/2012 |
| EP | 2429603 | A2 | 3/2012 |
| EP | 2459269 | A1 | 6/2012 |
| EP | 2497521 | A1 | 9/2012 |
| EP | 2140892 | B1 | 10/2012 |
| EP | 2505228 | A1 | 10/2012 |
| EP | 2150811 | B1 | 1/2013 |
| EP | 1833529 | B1 | 2/2013 |
| EP | 2554191 | A1 | 2/2013 |
| EP | 2277463 | B1 | 3/2013 |
| EP | 2564771 | A1 | 3/2013 |
| EP | 2151257 | B1 | 4/2013 |
| EP | 2575922 | A2 | 4/2013 |
| EP | 1623730 | B1 | 5/2013 |
| EP | 2606919 | A1 | 6/2013 |
| EP | 2606920 | A1 | 6/2013 |
| EP | 2607712 | A1 | 6/2013 |
| EP | 1919550 | B1 | 7/2013 |
| EP | 2620173 | A1 | 7/2013 |
| EP | 1331017 | B1 | 8/2013 |
| EP | 2101840 | B1 | 9/2013 |
| EP | 2401003 | B1 | 10/2013 |
| EP | 2654878 | A2 | 10/2013 |
| EP | 2654883 | A2 | 10/2013 |
| EP | 2671083 | A1 | 12/2013 |
| EP | 1412001 | B1 | 1/2014 |
| EP | 1942965 | B1 | 1/2014 |
| EP | 2231222 | B1 | 2/2014 |
| EP | 2697890 | A2 | 2/2014 |
| EP | 1017433 | B1 | 3/2014 |
| EP | 1629855 | B1 | 4/2014 |
| EP | 2736581 | A2 | 6/2014 |
| EP | 2744460 | A1 | 6/2014 |
| EP | 2745869 | A1 | 6/2014 |
| EP | 1485613 | B1 | 7/2014 |
| EP | 1605988 | B1 | 8/2014 |
| EP | 2792696 | A2 | 10/2014 |
| EP | 2195043 | B1 | 12/2014 |
| EP | 1962949 | B1 | 2/2015 |
| EP | 2030641 | B1 | 2/2015 |
| EP | 2643927 | B1 | 4/2015 |
| EP | 2868331 | A2 | 5/2015 |
| EP | 1460972 | B1 | 6/2015 |
| EP | 2150569 | B1 | 6/2015 |
| EP | 2152783 | B1 | 6/2015 |
| EP | 2345439 | B1 | 6/2015 |
| EP | 2895215 | A2 | 7/2015 |
| EP | 1761306 | B1 | 8/2015 |
| EP | 2663347 | B1 | 8/2015 |
| EP | 2209508 | B1 | 9/2015 |
| EP | 2915129 | A1 | 9/2015 |
| EP | 2920421 | A2 | 9/2015 |
| EP | 2533732 | B1 | 11/2015 |
| EP | 1317305 | B1 | 12/2015 |
| EP | 1339443 | B1 | 1/2016 |
| EP | 2967284 | A1 | 1/2016 |
| EP | 2967547 | A1 | 1/2016 |
| EP | 2984731 | A1 | 2/2016 |
| EP | 2167158 | B1 | 3/2016 |
| EP | 2061531 | B1 | 4/2016 |
| EP | 2519274 | B1 | 4/2016 |
| EP | 1996252 | B1 | 5/2016 |
| EP | 2464395 | B1 | 5/2016 |
| EP | 3047873 | A1 | 7/2016 |
| EP | 3047911 | A1 | 7/2016 |
| EP | 2643053 | B1 | 8/2016 |
| EP | 2734251 | B1 | 8/2016 |
| EP | 3050537 | A1 | 8/2016 |
| EP | 1942128 | B1 | 9/2016 |
| EP | 2099509 | B1 | 9/2016 |
| EP | 2719403 | B1 | 9/2016 |
| EP | 3072210 | A1 | 9/2016 |
| EP | 3072211 | A1 | 9/2016 |
| EP | 2405140 | B1 | 10/2016 |
| EP | 2197507 | B1 | 11/2016 |
| EP | 2538086 | B1 | 11/2016 |
| EP | 3086834 | A1 | 11/2016 |
| EP | 2806911 | B1 | 12/2016 |
| EP | 3110468 | A1 | 1/2017 |
| EP | 3113808 | A1 | 1/2017 |
| EP | 3119452 | A1 | 1/2017 |
| EP | 3120811 | A2 | 1/2017 |
| EP | 3131595 | A1 | 2/2017 |
| EP | 3131596 | A1 | 2/2017 |
| EP | 3131599 | A1 | 2/2017 |
| EP | 3131600 | A1 | 2/2017 |
| EP | 3131615 | A1 | 2/2017 |
| EP | 2585129 | B1 | 3/2017 |
| EP | 2594799 | B1 | 3/2017 |
| EP | 3146987 | A1 | 3/2017 |
| EP | 3157597 | A1 | 4/2017 |
| EP | 3173110 | A1 | 5/2017 |
| EP | 2825107 | B1 | 7/2017 |
| EP | 3185924 | A1 | 7/2017 |
| EP | 3185925 | A1 | 7/2017 |
| EP | 3189526 | A1 | 7/2017 |
| EP | 3191164 | A1 | 7/2017 |
| EP | 2618001 | B1 | 8/2017 |
| EP | 3197602 | A1 | 8/2017 |
| EP | 3198677 | A1 | 8/2017 |
| EP | 3204989 | A1 | 8/2017 |
| EP | 3212250 | A1 | 9/2017 |
| EP | 3219339 | A1 | 9/2017 |
| EP | 3223880 | A1 | 10/2017 |
| EP | 3232948 | A1 | 10/2017 |
| EP | 1885409 | B1 | 11/2017 |
| EP | 2292282 | B1 | 11/2017 |
| EP | 2945661 | B1 | 11/2017 |
| EP | 3238764 | A1 | 11/2017 |
| EP | 3244814 | A1 | 11/2017 |
| EP | 3247420 | A1 | 11/2017 |
| EP | 3247421 | A2 | 11/2017 |
| EP | 3248628 | A1 | 11/2017 |
| EP | 2136861 | B1 | 12/2017 |
| EP | 3256183 | A1 | 12/2017 |
| EP | 3256184 | A1 | 12/2017 |
| EP | 3256185 | A1 | 12/2017 |
| EP | 3256186 | A1 | 12/2017 |
| EP | 3007742 | B1 | 1/2018 |
| EP | 3277200 | A1 | 2/2018 |
| EP | 3287155 | A1 | 2/2018 |
| EP | 2482916 | B1 | 3/2018 |
| EP | 2948202 | B1 | 3/2018 |
| EP | 3294367 | A1 | 3/2018 |
| EP | 2945662 | B1 | 4/2018 |
| EP | 3310409 | A1 | 4/2018 |
| EP | 3222301 | B1 | 5/2018 |
| EP | 3222302 | B1 | 5/2018 |
| EP | 3313471 | A1 | 5/2018 |
| EP | 3324840 | A1 | 5/2018 |
| EP | 3325035 | A1 | 5/2018 |
| EP | 3326487 | A1 | 5/2018 |
| EP | 1789129 | B1 | 6/2018 |
| EP | 1990358 | B1 | 6/2018 |
| EP | 3329953 | A1 | 6/2018 |
| EP | 3335647 | A2 | 6/2018 |
| EP | 3341069 | A1 | 7/2018 |
| EP | 3349839 | A1 | 7/2018 |
| EP | 2219698 | B1 | 8/2018 |
| EP | 2890420 | B1 | 8/2018 |
| EP | 3352808 | A1 | 8/2018 |

(56) References Cited

FOREIGN PATENT DOCUMENTS

| | | |
|---|---|---|
| EP | 3352835 A1 | 8/2018 |
| EP | 3360233 A1 | 8/2018 |
| EP | 3360515 A1 | 8/2018 |
| EP | 1534381 B1 | 9/2018 |
| EP | 3108909 B1 | 9/2018 |
| EP | 3377001 A1 | 9/2018 |
| EP | 3377002 A1 | 9/2018 |
| EP | 3377134 A1 | 9/2018 |
| EP | 3377135 A1 | 9/2018 |
| EP | 3377136 A1 | 9/2018 |
| EP | 2249746 B1 | 10/2018 |
| EP | 2988795 B1 | 10/2018 |
| EP | 3383300 A1 | 10/2018 |
| EP | 3383448 A1 | 10/2018 |
| EP | 3388005 A1 | 10/2018 |
| JP | 64-52472 A | 2/1989 |
| JP | 02289241 A | 11/1990 |
| JP | 04176471 A | 6/1992 |
| JP | 04224760 A | 8/1992 |
| JP | 11062856 A | 3/1999 |
| JP | H11-062856 A | 3/1999 |
| JP | 02888609 B2 | 5/1999 |
| JP | 02927460 B2 | 7/1999 |
| JP | H11-244376 A | 9/1999 |
| JP | 2000102604 A | 4/2000 |
| JP | 2000107281 A | 4/2000 |
| JP | 2000283062 A | 10/2000 |
| JP | 03131696 B2 | 2/2001 |
| JP | 2001061957 A | 3/2001 |
| JP | 2001090687 A | 4/2001 |
| JP | 03174338 B2 | 6/2001 |
| JP | 2001173402 A | 6/2001 |
| JP | 03278160 B2 | 4/2002 |
| JP | 2002191123 A | 7/2002 |
| JP | 03313061 B2 | 8/2002 |
| JP | 2003047656 A | 2/2003 |
| JP | 2003070906 A | 3/2003 |
| JP | 2003205030 A | 7/2003 |
| JP | 2004011525 A | 1/2004 |
| JP | 2004016426 A | 1/2004 |
| JP | 2004028102 A | 1/2004 |
| JP | 2004073400 A | 3/2004 |
| JP | 2004209240 A | 7/2004 |
| JP | 2004278375 A | 10/2004 |
| JP | 03612581 B2 | 1/2005 |
| JP | 2005058617 A | 3/2005 |
| JP | 2005192687 A | 7/2005 |
| JP | 2005199076 A | 7/2005 |
| JP | 2005348996 A | 12/2005 |
| JP | 2006000631 A | 1/2006 |
| JP | 03786289 B2 | 6/2006 |
| JP | 03803417 B2 | 8/2006 |
| JP | 2006280571 A | 10/2006 |
| JP | 03854972 B2 | 12/2006 |
| JP | 2007044302 A | 2/2007 |
| JP | 2007075541 A | 3/2007 |
| JP | 2007089607 A | 4/2007 |
| JP | 2007089973 A | 4/2007 |
| JP | 2007236564 A | 9/2007 |
| JP | 04016441 B2 | 12/2007 |
| JP | 04022372 B2 | 12/2007 |
| JP | 2008018242 A | 1/2008 |
| JP | 04051812 B2 | 2/2008 |
| JP | 04072721 B2 | 4/2008 |
| JP | 04077902 B2 | 4/2008 |
| JP | 04078245 B2 | 4/2008 |
| JP | 04084060 B2 | 4/2008 |
| JP | 04086185 B2 | 5/2008 |
| JP | 04108054 B2 | 6/2008 |
| JP | 04121709 B2 | 7/2008 |
| JP | 04163384 B2 | 10/2008 |
| JP | 04179634 B2 | 11/2008 |
| JP | 2008264586 A | 11/2008 |
| JP | 04198986 B2 | 12/2008 |
| JP | 04209412 B2 | 1/2009 |
| JP | 2009090882 A | 4/2009 |
| JP | 04279494 B2 | 6/2009 |
| JP | 04308723 B2 | 8/2009 |
| JP | 2009178570 A | 8/2009 |
| JP | 2009254436 A | 11/2009 |
| JP | 2009273214 A | 11/2009 |
| JP | 04387106 B2 | 12/2009 |
| JP | 04391680 B2 | 12/2009 |
| JP | 04414925 B2 | 2/2010 |
| JP | 04440499 B2 | 3/2010 |
| JP | 04467187 B2 | 5/2010 |
| JP | 04468965 B2 | 5/2010 |
| JP | 04484320 B2 | 6/2010 |
| JP | 04512150 B2 | 7/2010 |
| JP | 2010158532 A | 7/2010 |
| JP | 04523961 B2 | 8/2010 |
| JP | 04523962 B2 | 8/2010 |
| JP | 04548450 B2 | 9/2010 |
| JP | 04549407 B2 | 9/2010 |
| JP | 2010246941 A | 11/2010 |
| JP | 04611364 B2 | 1/2011 |
| JP | 04611365 B2 | 1/2011 |
| JP | 04646393 B2 | 3/2011 |
| JP | 04655231 B2 | 3/2011 |
| JP | 04656332 B2 | 3/2011 |
| JP | 04674978 B2 | 4/2011 |
| JP | 2011072533 A | 4/2011 |
| JP | 2011116765 A | 6/2011 |
| JP | 04728351 B2 | 7/2011 |
| JP | 04741242 B2 | 8/2011 |
| JP | 04741489 B2 | 8/2011 |
| JP | 2011161401 A | 8/2011 |
| JP | 04795536 B2 | 10/2011 |
| JP | 04851333 B2 | 1/2012 |
| JP | 04865825 B2 | 2/2012 |
| JP | 04881154 B2 | 2/2012 |
| JP | 04897811 B2 | 3/2012 |
| JP | 04907028 B2 | 3/2012 |
| JP | 04908737 B2 | 4/2012 |
| JP | 04964854 B2 | 7/2012 |
| JP | 04987999 B2 | 8/2012 |
| JP | 05047447 B2 | 10/2012 |
| JP | 05048749 B2 | 10/2012 |
| JP | 05093869 B2 | 12/2012 |
| JP | 05102033 B2 | 12/2012 |
| JP | 05164558 B2 | 3/2013 |
| JP | 05185629 B2 | 4/2013 |
| JP | 05193059 B2 | 5/2013 |
| JP | 05197636 B2 | 5/2013 |
| JP | 2013078564 A | 5/2013 |
| JP | 05215580 B2 | 6/2013 |
| JP | 05267227 B2 | 8/2013 |
| JP | 05286268 B2 | 9/2013 |
| JP | 2013192711 A | 9/2013 |
| JP | 2014004303 A | 1/2014 |
| JP | 05427620 B2 | 2/2014 |
| JP | 05429714 B2 | 2/2014 |
| JP | 05440528 B2 | 3/2014 |
| JP | 05440529 B2 | 3/2014 |
| JP | 05461710 B2 | 4/2014 |
| JP | 05500348 B2 | 5/2014 |
| JP | 2014114784 A | 6/2014 |
| JP | 05539484 B2 | 7/2014 |
| JP | 05557175 B2 | 7/2014 |
| JP | 05590213 B2 | 9/2014 |
| JP | 05596974 B2 | 10/2014 |
| JP | 05611948 B2 | 10/2014 |
| JP | 05633512 B2 | 12/2014 |
| JP | 05656835 B2 | 1/2015 |
| JP | 05673795 B2 | 2/2015 |
| JP | 05675786 B2 | 2/2015 |
| JP | 05676118 B2 | 2/2015 |
| JP | 05701848 B2 | 4/2015 |
| JP | 05711245 B2 | 4/2015 |
| JP | 05750492 B2 | 7/2015 |
| JP | 05781597 B2 | 9/2015 |
| JP | 2015159947 A | 9/2015 |
| JP | 05837162 B2 | 12/2015 |
| JP | 05868180 B2 | 2/2016 |

(56) References Cited

FOREIGN PATENT DOCUMENTS

| | | |
|---|---|---|
| JP | 05894116 B2 | 3/2016 |
| JP | 05894678 B2 | 3/2016 |
| JP | 2016028764 A | 3/2016 |
| JP | 2016182342 A | 10/2016 |
| JP | 06034858 B2 | 11/2016 |
| JP | 06038018 B2 | 12/2016 |
| JP | 06054106 B2 | 12/2016 |
| JP | 2016202553 A | 12/2016 |
| JP | 06083929 B2 | 2/2017 |
| JP | 2017035323 A | 2/2017 |
| JP | 2017517306 A | 6/2017 |
| JP | 2017127675 A | 7/2017 |
| JP | 06178666 B2 | 8/2017 |
| JP | 2017159083 A | 9/2017 |
| JP | 06220867 B2 | 10/2017 |
| JP | 06236451 B2 | 11/2017 |
| JP | 06267625 B2 | 1/2018 |
| JP | 2018020199 A | 2/2018 |
| JP | 06295204 B2 | 3/2018 |
| JP | 06329358 B2 | 5/2018 |
| JP | 06339371 B2 | 6/2018 |
| JP | 06345112 B2 | 6/2018 |
| JP | 06353787 B2 | 7/2018 |
| JP | 06382285 B2 | 8/2018 |
| JP | 2018122146 A | 8/2018 |
| JP | 2018523541 A | 8/2018 |
| WO | WO87/002894 A2 | 5/1987 |
| WO | WO88/009874 A1 | 12/1988 |
| WO | WO92/002263 A1 | 2/1992 |
| WO | WO92/003181 A1 | 3/1992 |
| WO | WO95/031196 A1 | 11/1995 |
| WO | WO96/016684 A1 | 6/1996 |
| WO | WO98/042984 A1 | 10/1998 |
| WO | WO00/019097 A1 | 4/2000 |
| WO | WO00/027446 A1 | 5/2000 |
| WO | WO00/035515 A1 | 6/2000 |
| WO | WO01/041070 A1 | 6/2001 |
| WO | WO01/074419 A1 | 10/2001 |
| WO | WO01/087176 A1 | 11/2001 |
| WO | WO01/095813 A1 | 12/2001 |
| WO | WO02/053226 A2 | 7/2002 |
| WO | WO02/070039 A2 | 9/2002 |
| WO | WO02/072000 A1 | 9/2002 |
| WO | WO02/081021 A1 | 10/2002 |
| WO | WO03/061727 A2 | 7/2003 |
| WO | WO03/094716 A1 | 11/2003 |
| WO | WO03/103745 A2 | 12/2003 |
| WO | WO2004/026394 A1 | 4/2004 |
| WO | WO2004/034034 A1 | 4/2004 |
| WO | WO2004/088480 A2 | 10/2004 |
| WO | WO2004/098677 A1 | 11/2004 |
| WO | WO2005/020848 A2 | 3/2005 |
| WO | WO2005/033671 A1 | 4/2005 |
| WO | WO2005/037348 A1 | 4/2005 |
| WO | WO2005/054680 A1 | 6/2005 |
| WO | WO2005/108796 A1 | 11/2005 |
| WO | WO2006/040252 A1 | 4/2006 |
| WO | WO2006/053384 A1 | 5/2006 |
| WO | WO2006/081255 A2 | 8/2006 |
| WO | WO2006/121698 A2 | 11/2006 |
| WO | WO2007/008907 A2 | 1/2007 |
| WO | WO2007/033933 A1 | 3/2007 |
| WO | WO2007/053881 A1 | 5/2007 |
| WO | WO2007/065408 A2 | 6/2007 |
| WO | WO2007/092494 A2 | 8/2007 |
| WO | WO2007/105842 A1 | 9/2007 |
| WO | WO2007/146231 A2 | 12/2007 |
| WO | WO2008/005747 A2 | 1/2008 |
| WO | WO2008/008427 A2 | 1/2008 |
| WO | WO2008/088874 A2 | 7/2008 |
| WO | WO2008/102015 A1 | 8/2008 |
| WO | WO2008/121143 A1 | 10/2008 |
| WO | WO2008/121145 A1 | 10/2008 |
| WO | WO2008/137237 A2 | 11/2008 |
| WO | WO2008/140034 A1 | 11/2008 |
| WO | WO2009/017549 A1 | 2/2009 |
| WO | WO2009035581 A1 | 3/2009 |
| WO | WO2009/046789 A1 | 4/2009 |
| WO | WO2009/075668 A2 | 6/2009 |
| WO | WO2010/025411 A2 | 3/2010 |
| WO | WO2011/003043 A1 | 1/2011 |
| WO | WO2011/024928 A1 | 3/2011 |
| WO | WO2011/035925 A1 | 3/2011 |
| WO | WO2011/039091 A1 | 4/2011 |
| WO | WO2011/081629 A1 | 7/2011 |
| WO | WO2011/082212 A1 | 7/2011 |
| WO | WO2011/085040 A1 | 7/2011 |
| WO | WO2011/117566 A1 | 9/2011 |
| WO | WO2011/119060 A2 | 9/2011 |
| WO | WO2012/051454 A2 | 4/2012 |
| WO | WO2012/064674 A1 | 5/2012 |
| WO | WO2012/075152 A1 | 6/2012 |
| WO | WO2012/075262 A1 | 6/2012 |
| WO | WO2012/087811 A2 | 6/2012 |
| WO | WO2012/094535 A2 | 7/2012 |
| WO | WO2012/094641 A2 | 7/2012 |
| WO | WO2012/112129 A1 | 8/2012 |
| WO | WO2013/034547 A1 | 3/2013 |
| WO | WO2013/093058 A1 | 6/2013 |
| WO | WO2013/127182 A1 | 9/2013 |
| WO | WO2013/134319 A1 | 9/2013 |
| WO | WO2013/148560 A1 | 10/2013 |
| WO | WO2013/148697 A1 | 10/2013 |
| WO | WO2014/070458 A1 | 5/2014 |
| WO | WO2014/096408 A1 | 6/2014 |
| WO | WO2014/106635 A1 | 7/2014 |
| WO | WO2014/116639 A1 | 7/2014 |
| WO | WO2014/142754 A1 | 9/2014 |
| WO | WO2014/143593 A1 | 9/2014 |
| WO | WO2014/164136 A1 | 10/2014 |
| WO | WO2014/164292 A1 | 10/2014 |
| WO | WO2014/166128 A1 | 10/2014 |
| WO | WO2014/169023 A2 | 10/2014 |
| WO | WO2015/119705 A1 | 8/2015 |
| WO | WO2015/160943 A1 | 10/2015 |
| WO | WO2015/160979 A1 | 10/2015 |
| WO | WO2015/171156 A1 | 11/2015 |
| WO | WO2015/175711 A1 | 11/2015 |
| WO | WO2015/175718 A1 | 11/2015 |
| WO | WO2015/187659 A2 | 12/2015 |
| WO | WO2016/100600 A2 | 6/2016 |
| WO | WO2016/113266 A1 | 7/2016 |
| WO | WO2016/116630 A2 | 7/2016 |
| WO | WO2017/001358 A1 | 1/2017 |
| WO | WO2017/011257 A1 | 1/2017 |
| WO | WO2017/032751 A1 | 3/2017 |
| WO | WO2017/048733 A1 | 3/2017 |
| WO | WO2017/060254 A1 | 4/2017 |
| WO | WO2017/060257 A1 | 4/2017 |
| WO | WO2017/075322 A1 | 5/2017 |
| WO | WO2017/087380 A1 | 5/2017 |
| WO | WO2017/120453 A1 | 7/2017 |
| WO | WO2017/133425 A1 | 8/2017 |
| WO | WO2017/134657 A1 | 8/2017 |
| WO | WO2017/139113 A1 | 8/2017 |
| WO | WO2017/139246 A1 | 8/2017 |
| WO | WO2017/147082 A1 | 8/2017 |
| WO | WO2017/147103 A1 | 8/2017 |
| WO | WO2017/147291 A1 | 8/2017 |
| WO | WO2017/151987 A1 | 9/2017 |
| WO | WO2017/156386 A1 | 9/2017 |
| WO | WO2017/159849 A1 | 9/2017 |
| WO | WO2017/165372 A1 | 9/2017 |
| WO | WO2017/178904 A1 | 10/2017 |
| WO | WO2017/183124 A1 | 10/2017 |
| WO | WO2017/190155 A2 | 11/2017 |
| WO | WO2017/192119 A1 | 11/2017 |
| WO | WO2017/196271 A1 | 11/2017 |
| WO | WO2017/205909 A1 | 12/2017 |
| WO | WO2017/210318 A2 | 12/2017 |
| WO | WO2017/214118 A1 | 12/2017 |
| WO | WO2017/214183 A1 | 12/2017 |
| WO | WO2017/217946 A1 | 12/2017 |
| WO | WO2018/007120 A1 | 1/2018 |

(56) References Cited

FOREIGN PATENT DOCUMENTS

| | | |
|---|---|---|
| WO | WO2018/007471 A1 | 1/2018 |
| WO | WO2018/017678 A1 | 1/2018 |
| WO | WO2018/017683 A1 | 1/2018 |
| WO | WO2018/017716 A1 | 1/2018 |
| WO | WO2018/026764 A1 | 2/2018 |
| WO | WO2018/026769 A1 | 2/2018 |
| WO | WO2018/031741 A1 | 2/2018 |
| WO | WO2018/035069 A1 | 2/2018 |
| WO | WO2018/039124 A1 | 3/2018 |
| WO | WO2018/039326 A1 | 3/2018 |
| WO | WO2018/041963 A1 | 3/2018 |
| WO | WO2018/045299 A1 | 3/2018 |
| WO | WO2018/051091 A1 | 3/2018 |
| WO | WO2018/052482 A1 | 3/2018 |
| WO | WO2018/057482 A1 | 3/2018 |
| WO | WO2018/057563 A1 | 3/2018 |
| WO | WO2018/061002 A1 | 4/2018 |
| WO | WO2018/064437 A1 | 4/2018 |
| WO | WO2018/067410 A1 | 4/2018 |
| WO | WO2018/073150 A1 | 4/2018 |
| WO | WO2018/078370 A1 | 5/2018 |
| WO | WO2018/078615 A1 | 5/2018 |
| WO | WO2018/082987 A1 | 5/2018 |
| WO | WO2018/088939 A1 | 5/2018 |
| WO | WO2018/089970 A1 | 5/2018 |
| WO | WO2018/093663 A1 | 5/2018 |
| WO | WO2018/096531 A1 | 5/2018 |
| WO | WO2018/118756 A1 | 6/2018 |
| WO | WO2018/132181 A1 | 7/2018 |
| WO | WO2018/132182 A1 | 7/2018 |
| WO | WO2018/135477 A1 | 7/2018 |
| WO | WO2018/135478 A1 | 7/2018 |
| WO | WO2018/136592 A2 | 7/2018 |
| WO | WO2018/139508 A1 | 8/2018 |
| WO | WO2018/145434 A1 | 8/2018 |
| WO | WO2018/146045 A1 | 8/2018 |
| WO | WO2018/146170 A1 | 8/2018 |
| WO | WO2018/146173 A1 | 8/2018 |
| WO | WO2018/146177 A1 | 8/2018 |
| WO | WO2018/148456 A1 | 8/2018 |
| WO | WO2018/156524 A1 | 8/2018 |
| WO | WO2018/158636 A1 | 9/2018 |
| WO | WO2018/177344 A1 | 10/2018 |
| WO | WO2018/178939 A1 | 10/2018 |
| WO | WO2018/183128 A1 | 10/2018 |
| WO | WO2018/187576 A2 | 10/2018 |
| WO | WO2018/226991 A1 | 12/2018 |
| WO | WO2019/094963 A1 | 5/2019 |
| WO | WO2019/158996 A1 | 8/2019 |

OTHER PUBLICATIONS

Hildebrand et al.; U.S. Appl. No. 16/595,280 entitled "Intravascular blood pumps and methods of use," filed Oct. 7, 2019.

Calomeni et al.; U.S. Appl. No. 16/988,221 entitled "Catheter blood pumps and collapsible pump housings," filed Aug. 7, 2020.

Calomeni et al.; U.S. Appl. No. 17/033,455 entitled "Catheter blood pump and collapsible blood conduits," filed Sep. 25, 2020.

Wallin et al.; U.S. Appl. No. 17/033,482 entitled "Intravascular blood pump system and methods of use and control thereof," filed Sep. 25, 2020.

Dhaliwal et al.; U.S. Appl. No. 17/033,493 entitled "Catheter blood pumps and collapsible pump housings," filed Sep. 25, 2020.

Reitan et al.; First human use of the reitan catheter pump; Asaio Journal; 47(2); p. 124; Mar.-Apr. 2001.

Salahieh et al., U.S. Appl. No. 16/189,876; entitled "Intravascular fluid movement devices, systems, and methods of use," filed Nov. 13, 2018.

Salahieh et al.; U.S. Appl. No. 16/265,828 entitled "Intravascular blood pumps and methods of use and manufacture," filed Feb. 1, 2019.

* cited by examiner

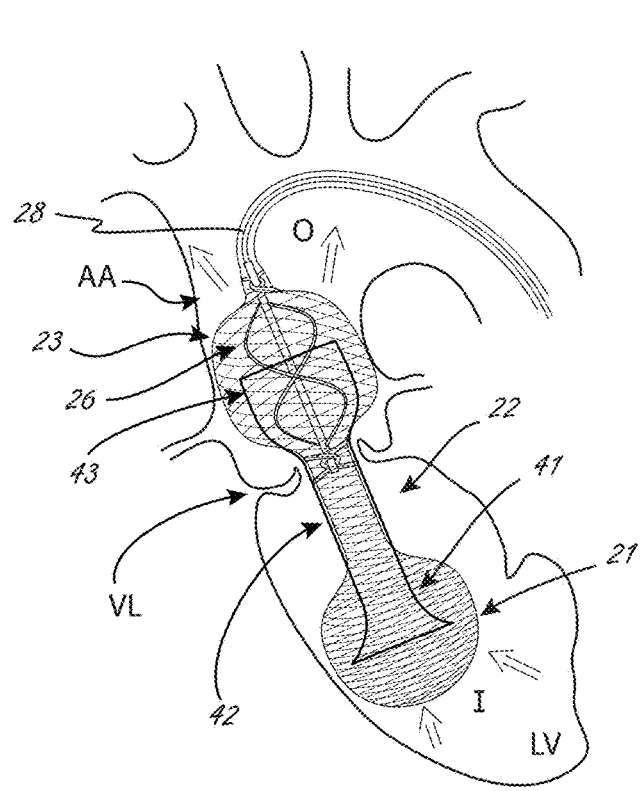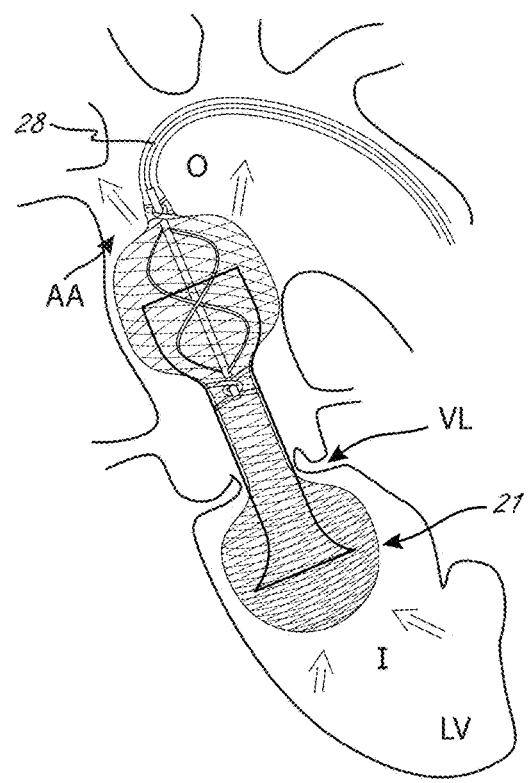
Fig. 4A   Fig. 4B
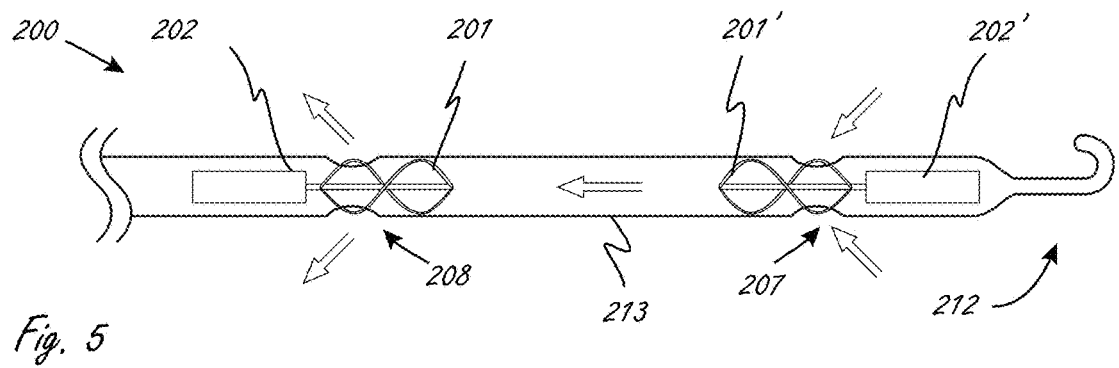
Fig. 5

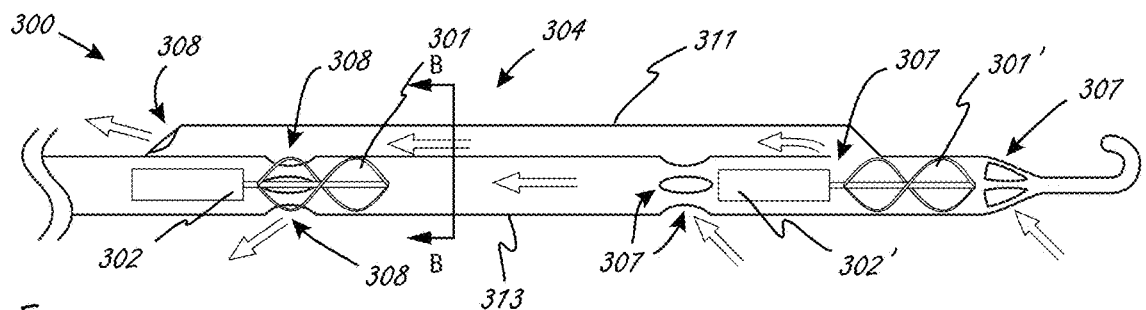
Fig. 6A
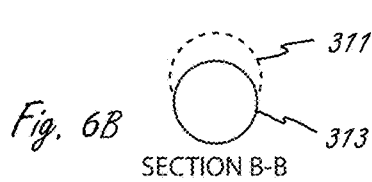
Fig. 6B SECTION B-B
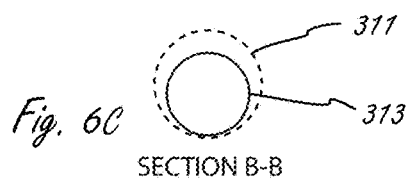
Fig. 6C SECTION B-B
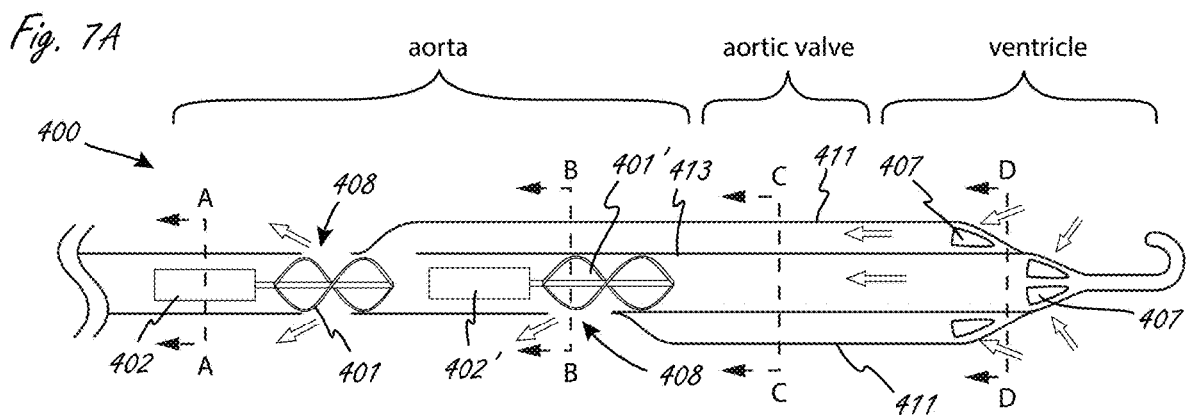
Fig. 7A
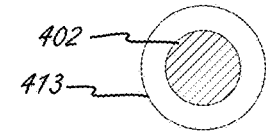
Fig. 7B
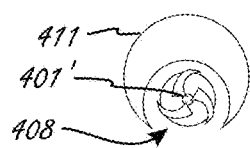
Fig. 7C
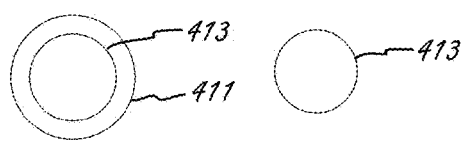
Fig. 7D
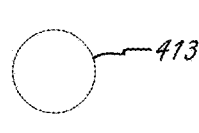
Fig. 7E

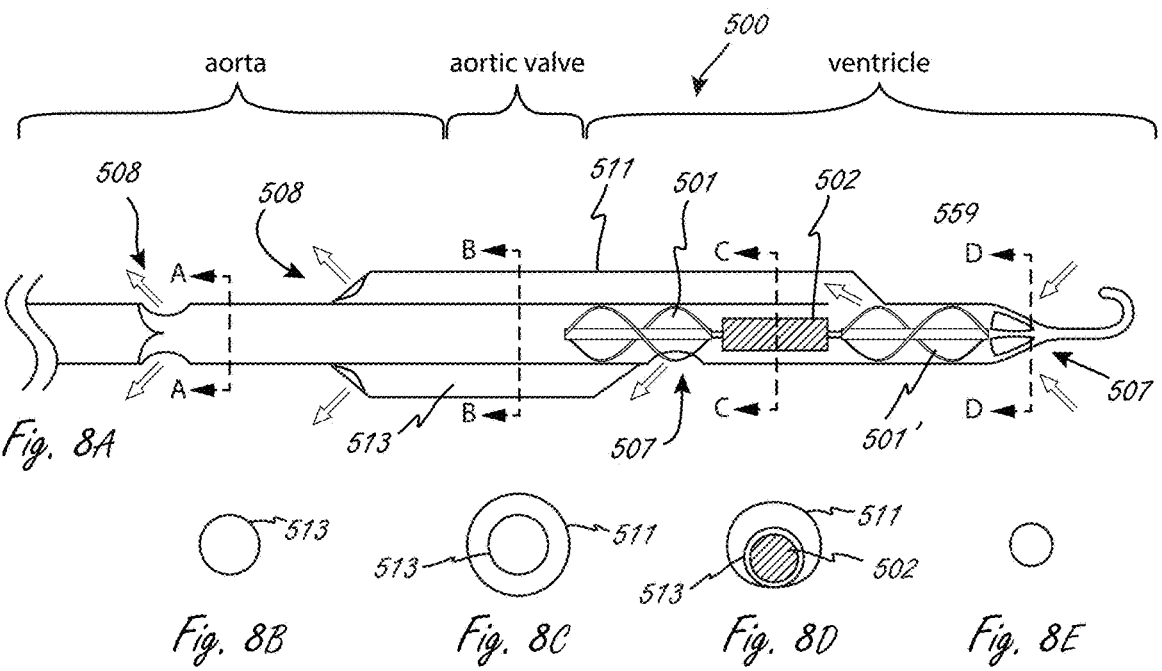
Fig. 8A
Fig. 8B  Fig. 8C  Fig. 8D  Fig. 8E
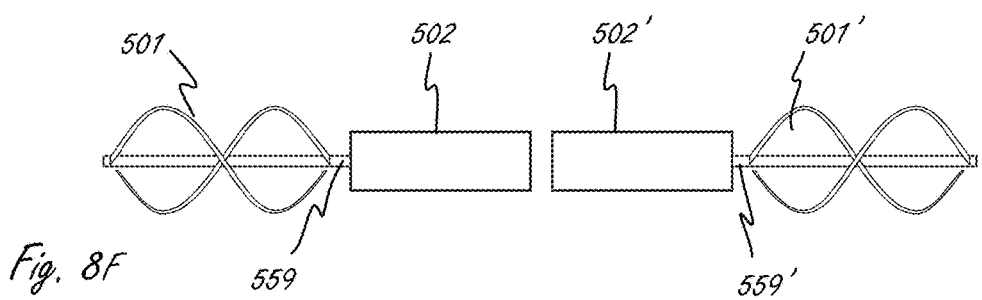
Fig. 8F
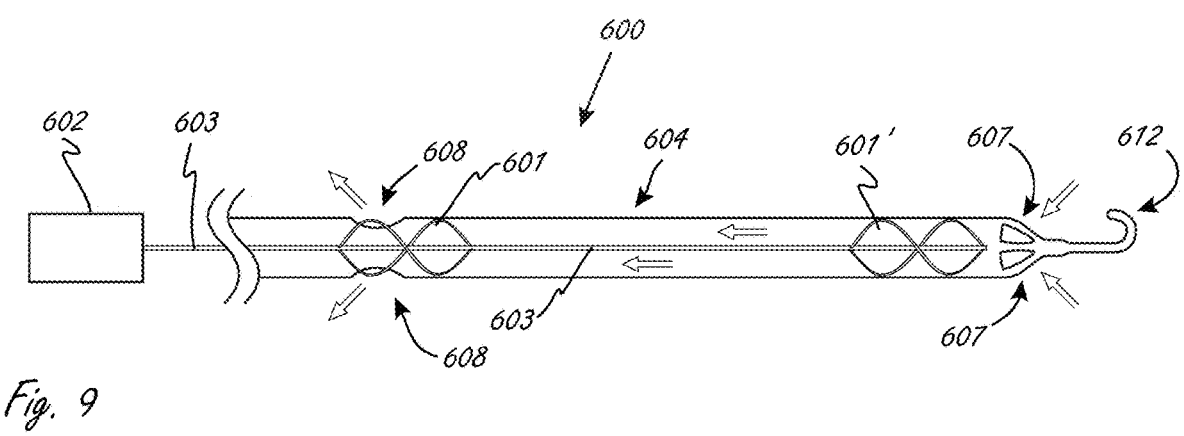
Fig. 9

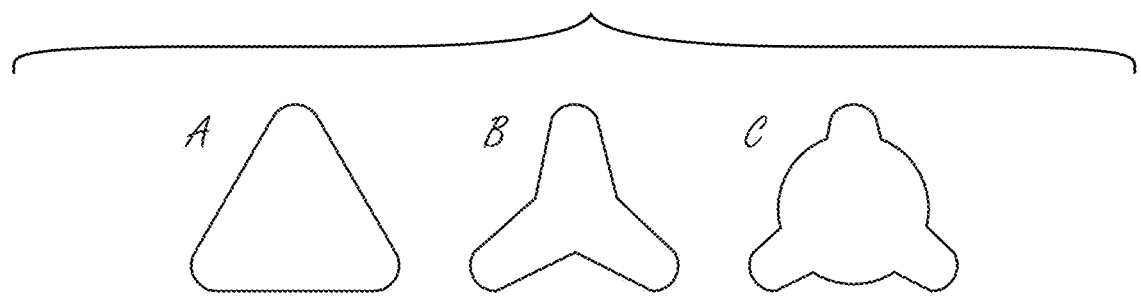
variations for non-circular pump body as deformed by aortic valve
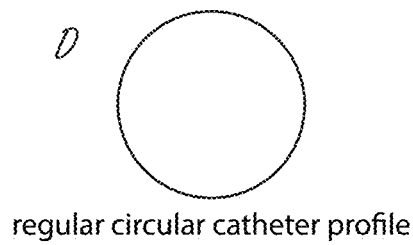
regular circular catheter profile
Fig. 15A-D
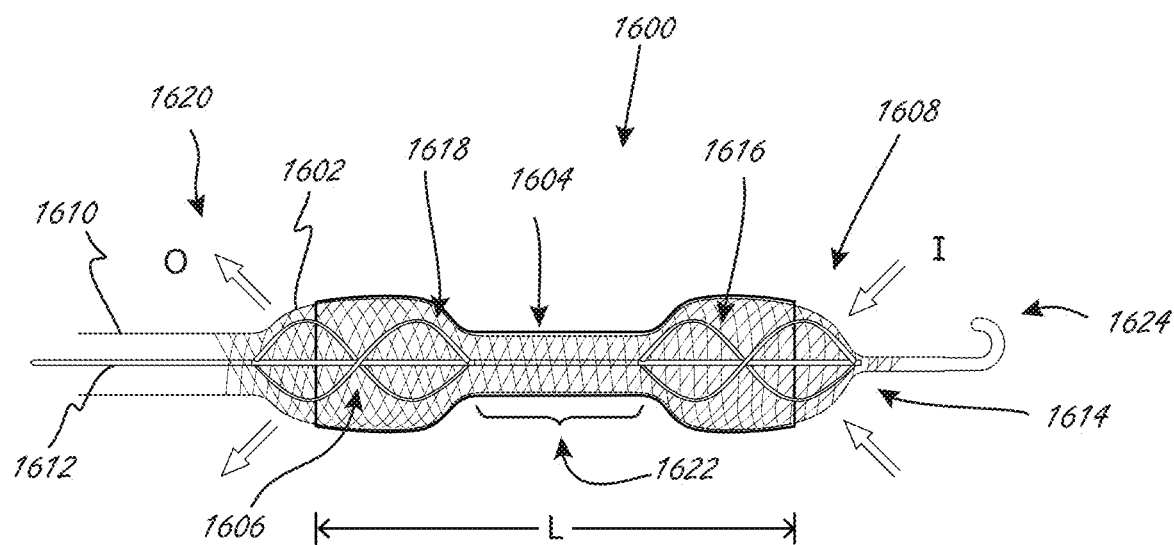
Fig. 16

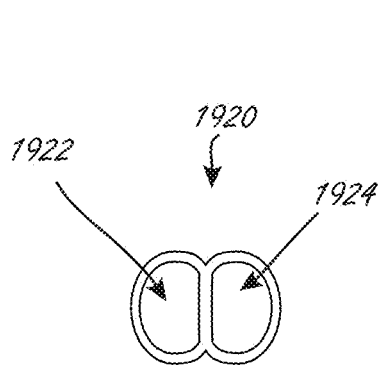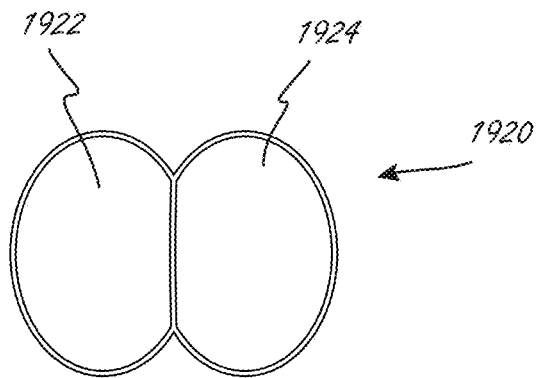
Fig. 25A  Fig. 25B
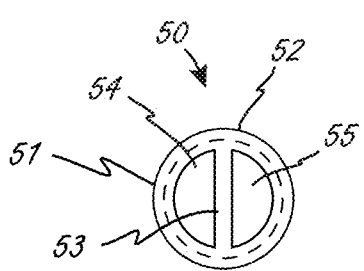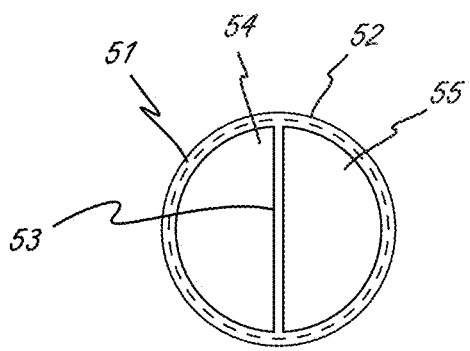
Fig. 26A  Fig. 26B
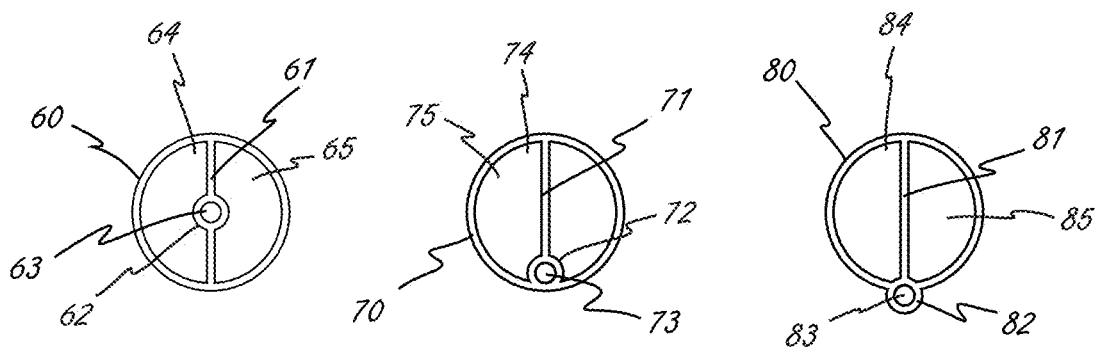
Fig. 27A  Fig. 27B  Fig. 27vC

INTRAVASCULAR FLUID MOVEMENT DEVICES, SYSTEMS, AND METHODS OF USE

CROSS REFERENCE TO RELATED APPLICATIONS

This application is a continuation of International Application No. PCT/US2018/036506, filed Jun. 7, 2018; which application claims priority to the following U.S. Provisional Patent Applications, all which are incorporated by reference herein: App. No. 62/516,296, filed Jun. 7, 2017, and App. No. 62/542,488, filed Aug. 8, 2017.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular assist device ("pVAD").

There is a need to provide additional improvements to the field of pVADs and similar blood pumps for treating compromised cardiac blood flow. Current pVADs that are designed to add to or replace cardiac output can be undesirably large for insertion into the patient's blood vessels (e.g., requiring a large femoral artery access sheath or cutdown that increases the complication rate after the procedure), provide insufficient blood flow or create a significant amount of hemolysis damage to the blood cells, which can lead to adverse outcomes and in some cases death.

There is a need for improvements to pVAD or similar devices to minimize the insertion profile, thus minimizing procedure complications associated with vascular access, to maximize the flow of blood created or assisted by the devices, to minimize blood hemolysis and thrombosis, and to facilitate the procedure steps that physicians and their staff need to manage during use of the product.

In one aspect, there is a need for smaller delivery profile devices that can be inserted through access sheaths optionally less than 12 FR, such as 8 FR or 9 FR, and that can also pump blood flow in the range of 3.5 to 6.0 L/min, such as 4.0 to 5.0 L/min, for example, at approximately 60 mmHg of head pressure. Because higher rotary pump impeller speeds are known to increase the risk of hemolysis, in one aspect there is a need for a pump that can provide sufficient flow at rotational speeds significantly less than the 50,000 rpm speed that some pVAD pumps employ. These needs and other problems with existing approaches are addressed by the disclosure herein.

SUMMARY OF THE DISCLOSURE

The disclosure is related to medical devices that are adapted to, when in use, move fluid such as a blood.

One aspect of the disclosure is an intravascular blood pump including an expandable member having a collapsed, delivery configuration and an expanded, deployed configuration, the expandable member having a proximal end and a distal end; an impeller disposed radially and axially within the expandable member; and a conduit coupled to the expandable member, the conduit at least partially defining a blood flow lumen between a distal end of the conduit and a proximal end of the conduit, and wherein the conduit disposed solely radially inside of the expandable member in a distal section of the expandable member.

A proximal section and the distal section of the expandable member can each have outermost dimensions that are greater than an outermost dimension of a central region of the expandable member that is disposed axially in between the proximal and distal sections.

A distal end of the conduit can have a configuration that is flared outward. A proximal end of the conduit may not have a flared configuration.

The blood pump can further comprise a drive cable in operable communication with the impeller.

The blood pump can further include a plurality of distal centering struts that are coupled to the expandable member and extend around the drive cable distal to the impeller, and a plurality of proximal centering struts that are coupled to the expandable member and extend around the drive cable proximal to the impeller.

In some instances, the conduit can be non-permeable, semi-permeable, or even porous.

The expandable member can comprise a plurality of elongate elements that define a plurality of apertures.

The conduit can be disposed radially within the expandable member from the proximal end of the conduit to the distal end of the conduit.

The conduit, where it is disposed solely radially inside of the expandable member, can be radially spaced away from the expandable member with a gap between the conduit and the expandable member.

The conduit can also be disposed radially outside of the expandable member in a proximal region of the expandable member.

One aspect of the disclosure is an intravascular fluid pump with a working portion with a deployed configuration. The working portion includes a distal expandable member with a collapsed delivery configuration and a deployed configuration, the distal expandable member having a proximal end and a distal end, a distal impeller disposed radially within the distal expandable member; a proximal expandable member with a collapsed delivery configuration and a deployed configuration, the proximal expandable member having a proximal end and a distal end, the distal end of which is axially spaced from the proximal end of the distal expandable member; a proximal impeller disposed radially within the proximal expandable member, the proximal impeller spaced proximally from the distal impeller; a conduit extending axially between the proximal end of the distal expandable member and the distal end of the proximal expandable member, the conduit at least partially defining a blood flow lumen between a distal end of the conduit and a proximal end of the conduit, wherein a central region of the conduit spans an axial distance, and the distal expandable member and the proximal expandable member do not extend axially into the central region, wherein the distal end of the distal expandable member extends further distally than the distal end of the conduit, and the proximal end of the proximal expandable member extends further proximally than the proximal end of the conduit; and an elongate portion extending proximally from the working portion.

The conduit can be coupled to the distal expandable member and the proximal expandable member.

The working portion can further include a central tubular element that is coupled to the expandable members, wherein the central tubular element is disposed in the lumen and is disposed between the proximal and distal expandable members. The distal end of the proximal expandable member can be coupled to a proximal end of the central tubular element, and the proximal end of the distal expandable member can be coupled to a distal end of the central tubular element, the central tubular element can extend between the proximal and distal expandable members. The central tubular element can have the same outermost dimension in both the collapsed and deployed configurations.

The proximal and distal impellers can optionally be driven by a common drive mechanism, such as a common drive cable that can be coupled to the proximal impeller and to the distal impeller. A common drive mechanism can define a lumen, which can optionally be used as a guidewire lumen.

A common drive cable can include a first section coupled to a second section with the second section adjacent the first section, the first and second sections having a common longitudinal axis and a common outer dimension measured orthogonally relative to the common axis, wherein the first section is stiffer than second section, and either the distal impeller or the proximal impeller is coupled to the first section. The first section can include a first tubular member and the second section can include a wound member. The drive cable can further include a third section adjacent the second section, the third section being coupled to the other of the distal impeller and the proximal impeller.

The proximal and distal impellers can be in operative communication with a common motor.

The distal expandable member can be coupled to a distal bearing and to a proximal bearing, wherein a drive mechanism extends through the distal and proximal bearings.

The proximal expandable member can be is coupled to a distal bearing and to a proximal bearing, wherein a drive mechanism extends through the distal and proximal bearings.

The distal expandable member can comprise a plurality of elongate segments disposed relative to one another to define a plurality of apertures, wherein at least a portion of one of the plurality of apertures is distal to the distal end of the conduit, defining at least one blood inlet aperture to allow blood to enter the lumen. The proximal expandable member can comprise a plurality of elongate segments disposed relative to one another to define a second plurality of apertures, wherein at least a portion of one of the second plurality of apertures is proximal to the proximal end of the conduit, defining at least one outlet aperture to allow blood to exit the lumen.

At least one of the distal and proximal expandable members has a plurality of elongate segments that are braided.

The conduit is optionally impermeable, optionally semipermeable, and optionally porous.

The conduit can be made of material such that, in the central region axially between the distal and proximal expandable members, the material is adapted to deform radially inward more easily than the expandable members in response to radially inward forces on the working portion.

The conduit can be coupled to the proximal expandable member at a location along the proximal expandable member with a greatest radial dimension measured orthogonally relative to a longitudinal axis of the proximal expandable member, and the conduit can be coupled to the distal expandable member at a location along the distal expandable member with a greatest radial dimension measured orthogonally relative to a longitudinal axis of the distal expandable member.

The conduit, at a location where it is coupled to the proximal expandable member, can be disposed radially within the proximal expandable member, and the conduit, at a location where it is coupled to the distal expandable member, can be disposed radially within the distal expandable member. The conduit, at a location where it is coupled to the proximal expandable member, can also be disposed radially outside of the proximal expandable member, and the conduit, at the location where it is coupled to the distal expandable member, can also be disposed radially outside of the distal expandable member. The proximal expandable member can have a distal section that tapers radially inward and distally, and the distal expandable member can have a proximal section that tapers radially inward and proximally, and wherein the conduit can be disposed solely radially outside of the proximal expandable member at a first location in the distal section and not coupled directly to the proximal expandable member at the first location, and wherein the conduit can be disposed solely radially outside of the distal expandable member at a second location in the proximal section and not coupled directly to the distal expandable member at the second location.

A distal end of the distal impeller, in the expanded configuration may not extend further distally than a distal end of the conduit.

A proximal end of the proximal impeller, in the expanded configuration, may not extend further proximally than a proximal end of the conduit.

The conduit can be flexible, and may optionally be conformable.

The proximal impeller may extend further proximally than a proximal end of the conduit in the deployed configuration.

The distal impeller may extend further distally than a distal end of the conduit in the deployed configuration.

A first portion of the conduit can be disposed solely radially outside of the proximal expandable member, and a second portion of the conduit that is proximal to the first portion of the conduit can be disposed radially inside the proximal expandable member. The first portion of the conduit can be distal to a distal end of the proximal impeller.

A first portion of the conduit can be disposed solely radially outside of the distal expandable member, and wherein a second portion of the conduit that is distal to the first portion of the conduit can be disposed radially inside the distal expandable member. The first portion of the conduit can be proximal to a proximal end of the distal impeller.

One aspect of the disclosure is related to methods of deploying an intravascular blood pump across a valve such as an aortic valve.

BRIEF DESCRIPTION OF THE DRAWINGS

FIGS. 4A and 4B illustrate an exemplary placement of the device from FIG. 3B.

FIG. 5 is a side view of an exemplary working portion.

FIGS. 6A, 6B and 6C illustrate at least a portion of an exemplary working portion.

FIGS. 7A-7E illustrate at least a portion of an exemplary working portion.

FIGS. 8A-8F illustrate at least a portion of an exemplary working portion.

FIG. 9 illustrates at least a portion of an exemplary medical device that has a working portion.

FIGS. 15A-15D are end views showing exemplary outer profiles of exemplary working portions in use.

FIG. 16 is a side view of an exemplary working portion that includes a conduit, a plurality of impellers, an expandable member

FIGS. 25A and 25B illustrate an exemplary multi-lumen working portion in a collapsed, delivery configuration (FIG. 25A) and an expanded configuration (FIG. 25B).

FIGS. 26A and 26B illustrates an exemplary multi-lumen design for a working portion, showing deployed and expanded configurations, respectively.

FIGS. 27A-C illustrate exemplary embodiments of a working portion with at least one additional lumens.

DETAILED DESCRIPTION

The present disclosure is related to medical devices, systems, and methods of use and manufacture. Medical devices herein may include a distal working portion adapted to be disposed within a physiologic vessel, wherein the distal working portion includes one or more components that act upon fluid. For example, distal working portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein unless specifically indicated otherwise.

Figure 1A:
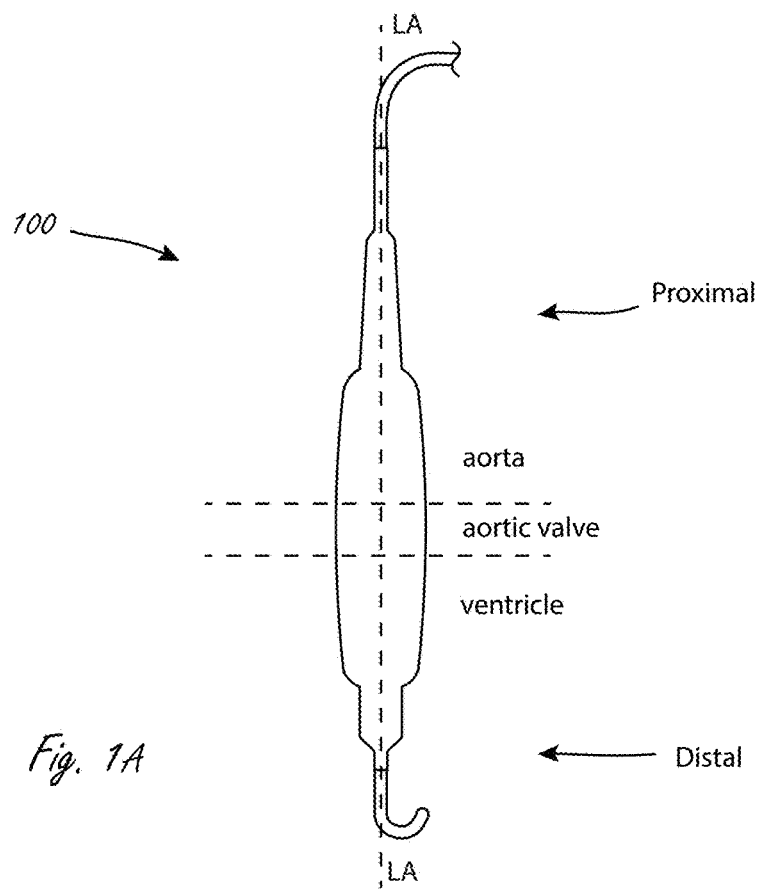
FIGS. 1A, 1B, 1C, 1D and 1E illustrate merely exemplary exterior profiles for working portions of medical devices herein.

FIGS. 1A-1E illustrate exemplary exterior profiles (i.e., outer configuration) for working portions (described in more detail below) of medical devices that extend across, or cross, a valve such as an aortic valve. Only a portion of the elongate proximal portions are shown, which extend proximally from the working portions. The relative positions of an aortic valve, ascending aorta, and left ventricle, are shown. FIG. 1A illustrates an exemplary embodiment in which a medical device includes working portion 100 that has a generally cylindrical (i.e., not a true cylinder but closely resembling a cylinder such that one of ordinary skill in the art would understand it to be considered to be cylindrical) expanded configuration, with a central region that spans a valve having the greatest outer dimension (measured orthogonally relative to longitudinal axis LA, shown only in FIG. 1A for simplicity), and wherein the outer dimension gets smaller in the proximal and distal directions. The working portion is sized such that a distal end is disposed in the left ventricle when a proximal end is disposed in the ascending aorta.

When a working portion is expanded at the location of a valve, the working portion may contact the valve leaflets (regardless of whether they are native leaflets or part of a replacement heart valve) and may cause damage to them when the leaflets are pressed against the working portion during heart pumping and to facilitate closure of an effective valve seal against the working portion. It may thus be advantageous to minimize or reduce the profile of the working portion at the location where it crosses or spans the valve (e.g., aortic) to minimize damage to the valve leaflets. FIGS. 1B-1E illustrate exemplary working portion configurations that have central regions with reduced profile dimensions and can be positioned at the location of a valve to reduce the likelihood of valve damage.

Figures 1B, 1C, 1D, 1E:
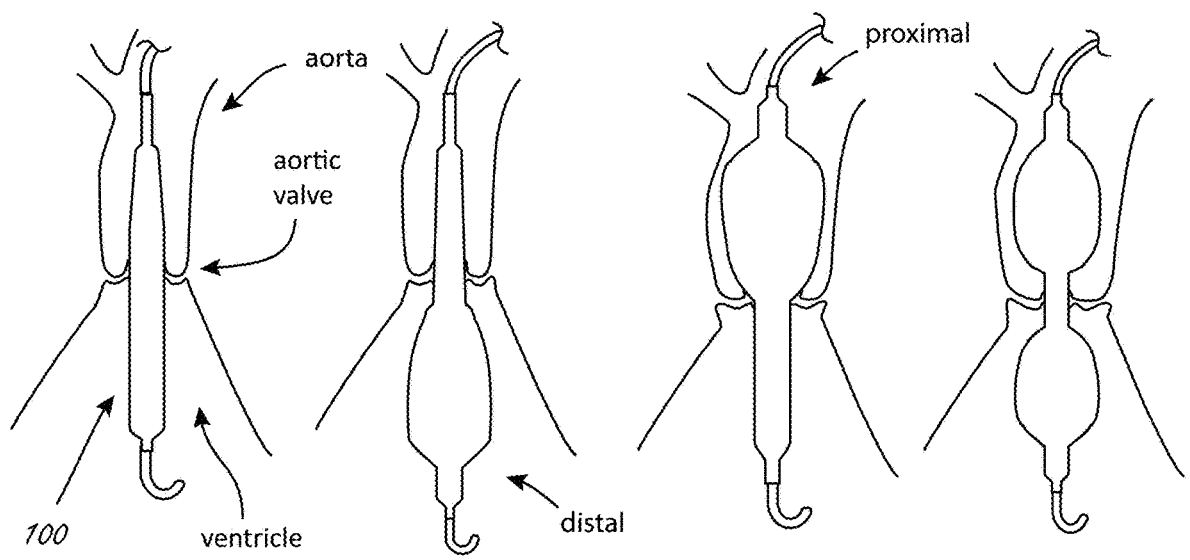

FIG. 1B shows an exemplary working portion that has a generally cylindrical expanded configuration as shown, and is sized such that a distal region is in the ventricle when a proximal region is in the ascending aorta. A central region of the working portion spans the valve. The expanded outer configuration is generally cylindrical.

FIG. 1C shows an exemplary working portion in an expanded configuration in which a distal region of the working portion expands to a greater outer dimension than a proximal region of the working portion. The outer dimension becomes substantially smaller (e.g., at least half as much) at the location of the valve and extending proximally.

FIG. 1D shows an exemplary working portion in an expanded configuration in which a proximal region of the working portion (which is disposed in the ascending aorta) expands to a greater outer dimension than a distal region of the working portion. The outer dimension becomes substantially smaller (e.g., at least half as much) at the location of the valve and extending distally.

FIG. 1E shows an exemplary working portion in an expanded configuration in which a proximal region and a distal region are configured to expand to a greater dimension that a central region, wherein the central region is disposed between the proximal and distal regions. The central region can have an outer dimension that is half as much or less than either or both of the proximal and distal regions. The working portion in FIG. 1E can be thought of as having a general dumbbell configuration when expanded.

In alternative embodiments, the working portion can have a generally uniform collapsed delivery profile, and is configured to expand to a generally uniform expanded larger profile. "Uniform" may refer to dimensions in this context of varying no more than 10%.

Figure 2A:
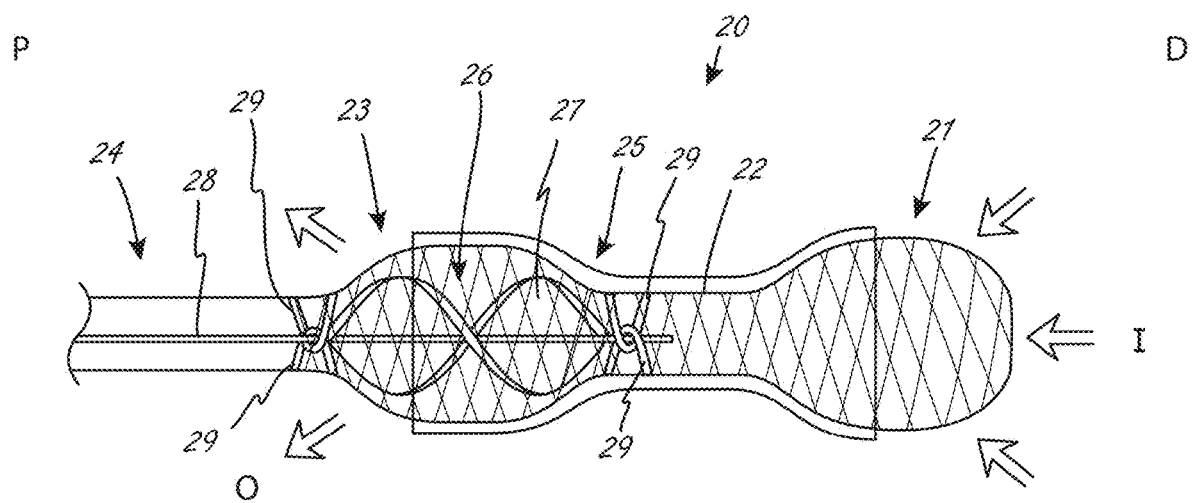
FIG. 2A is a side view of an exemplary working portion, which includes an expandable member, and impeller, and a conduit.
Figure 2B:
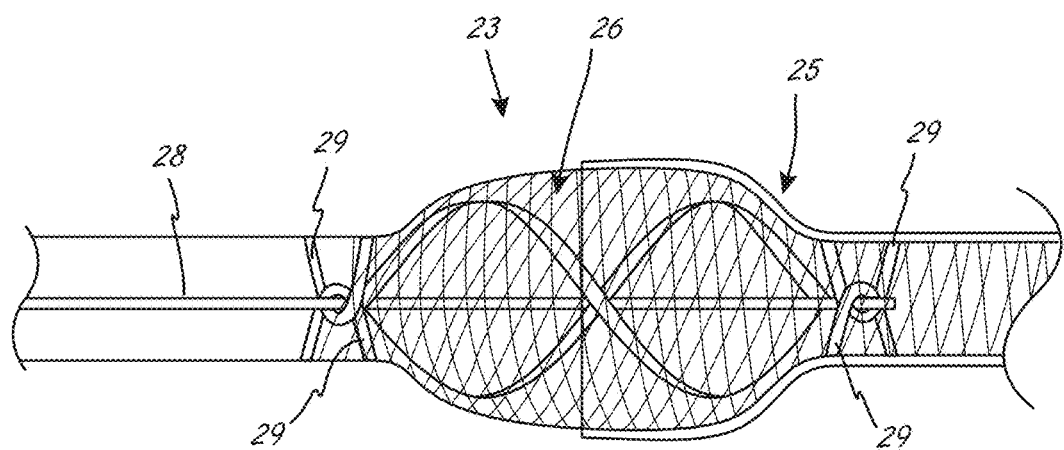
FIG. 2B is a close-up view of a portion of the view from FIG. 2A.

FIGS. 2A and 2B illustrate an exemplary fluid pump working portion that includes impeller 26 that is disposed radially within an expandable member. FIGS. 2A and 2B show the working portion configuration when it is expanded extracorporeally. The expandable member includes distal region 21, central region 22, and proximal region 23. Distal region 21 and proximal region 23 have larger outer dimensions than central region 22, and the expandable member can be thought of as having a dumbbell configuration. In use, central region 22, or at least a portion of it, can be positioned across a valve. The proximal and distal regions 23 and 21, respectively, have tapered end regions that taper down from a larger outer dimension in more central regions. Impeller 26 is disposed radially within proximal region 23, and a short portion of impeller 26 may also extend slightly within central region 22. Elongate shaft 28, which can be a drive shaft or drive cable, is coupled to impeller and drives the rotation of impeller 26 when activated (e.g., by a motor). Centering struts 29 (four of which are shown) are disposed at the ends of impeller 26, and extend around and function to center the shaft 28. Struts 29 are coupled to the expandable member and extend around shaft 28 to stabilize it. Two struts 29 at each end define an aperture through which shaft 29 extends. By centering the shaft 28, the struts 29 also center the impeller 26 within the expandable member and prevent the impeller blades from engaging the expandable member when they are rotating.

Working portion 20 also includes conduit 25 that is coupled to the expandable member. Conduit 25 extends from a location within distal region 21 to a location within proximal region 23, but does not extend to the distal and proximal ends of the expandable member. The conduit acts and is configured and made of material(s) that create a fluid lumen therein between an inflow region and an outflow end region. Flow into the inflow region is labeled "I," and flow out at the outflow region is labeled "O." The expandable member includes a plurality of elongate members that together define a plurality of apertures through which fluid can flow at the inflow and outflow regions. Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. In this embodiment conduit 25 is coupled to an exterior of the expandable member. The distal end of working portion has a large open surface area that permits sufficient blood inlet flow even if it is pushed against (i.e., contacting) an inner surface of a hollow anatomical structure such as, for example, a left ventricle of the heart. The proximal region of conduit 25 opens as an impeller shroud to permit efficient axial pump flow.

Any of the conduits herein, unless indicated to the contrary, can be secured to an expandable member such that the conduit, where is it secured, can be radially inside and/or outside of the expandable member. For example, a conduit can extend radially within the expandable member so that inner surface of the conduit is radially within the expandable member where it is secured to the expandable member.

FIG. 2A is an example of a working portion in which the conduit has flared distal and proximal regions, due to the configuration of the expandable member, as well as how far along (axially) the expandable member the conduit extends. FIG. 2A is also an example of a working portion with distal and proximal regions that are larger in outer dimension than a central region.

In alternative embodiments, the distal region of the conduit has a flared configuration like a trumpet bell to reduce the work energy required for fluid to enter the inlet region.

The expandable member can be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

The working portion in FIG. 2A can be adapted to be collapsible to a lower profile delivery configuration. The expandable member and impeller can be adapted to be collapsed to the delivery configuration. The conduit collapses with the expandable member due to its coupling with the expandable member. FIG. 2B illustrates a portion of the view from FIG. 2A, showing components amplified for clarity.

When the impeller is activated to rotate, the rotation pulls fluid into the inflow end, through the lumen defined by the conduit, and out of the outflow end.

In some embodiments, the expandable member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other.

Figure 3A:
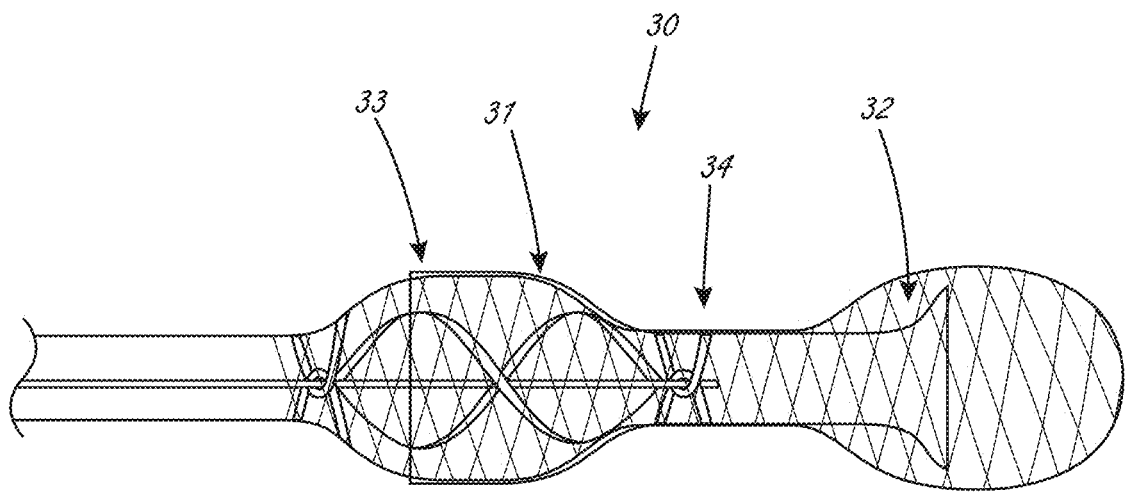
FIG. 3A is a side view of an exemplary working portion where a portion of a conduit is solely radially within an expandable member.

FIG. 3A illustrates an exemplary working portion 30 that is similar to that shown in FIGS. 2A and 2B. Components that are the same as in working portion 20 are not labeled for clarity, but are incorporated into this figure. Working portion 30 includes conduit 31 that includes distal region 32, central region 34, and proximal region 33. This embodiment differs from working portion 20 in FIG. 2A in that conduit distal region 32 is radially within the expandable member and is not attached directly to a portion of distal region 32. In the case of a working portion that is located across the aortic valve, for instance, this arrangement near the distal end of the expandable member allows for native cardiac ejection blood flow to go around (radially outside of) the more distal end of the conduit and through the aortic valve that is disposed adjacent to the conduit. Conduit 31 transitions from outside to inside the expandable member between the ends of the expandable member, and in this embodiment it transitions in a central region of the expandable member that has a reduced outer dimension.

Figure 3B:
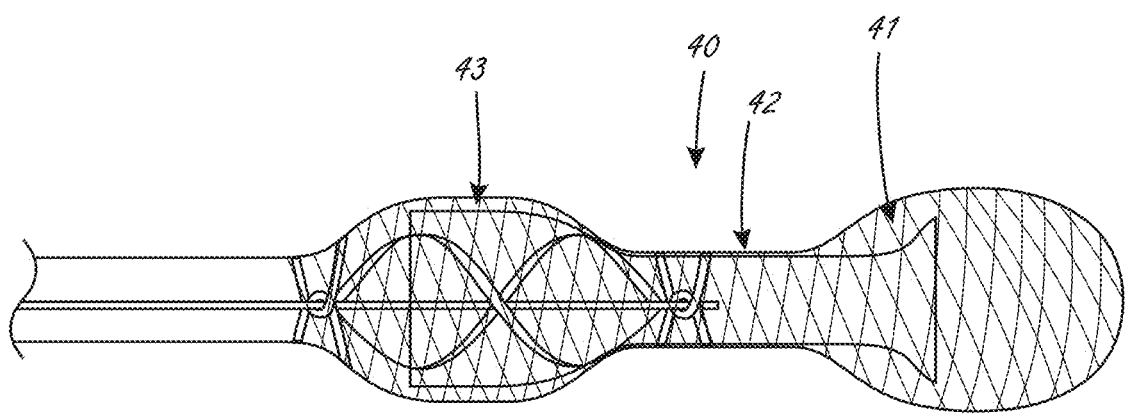
FIG. 3B is a side view of an exemplary working portion that includes an impeller.

FIG. 3B illustrates an exemplary working portion that is similar to that shown in FIGS. 2A and 3A. Parts that are the same are not re-labeled for clarity, but are incorporated into this figure. In FIG. 3B, working portion 40 has a conduit that extends radially within the expandable member, including distal region 41, central region 42 and proximal region 43. In distal region 41, there is a region where the conduit is solely radially within the expandable member, and not attached thereto, as shown. In the method of use that positions the working portion across the aortic valve, for instance, this arrangement near the proximal end of the expandable member allows for more native cardiac ejection blood flow that goes around (radially outside of) the conduit distal end and through the aortic valve adjacent to the conduit to enter the left and right main coronary arteries without obstruction by the conduit.

The fluid movement devices, system and methods herein can be used and positioned in a variety of locations within a body. While specific examples may be provided herein, it is understood that that the working portions can be positioned in different regions of a body than those specifically described herein.

FIGS. 4A and 4B show an exemplary working position of working portion 40 from FIG. 3B. Working portion 40 has been deployed to a deployed configuration and extends across an aortic valve, which includes aortic valve leaflets "VL." The expandable member distal region 21 is positioned in a left ventricle "LV," central region 22 extends across the valve, and proximal region 23 is positioned in the ascending aorta. A distal end of the proximal region 23 engages the leaflets as well, as is shown. The proximal region 23 has a configuration and size, relative to the opening of the valve, that prevent the proximal region 23 from passing through the valve, ensuring that the outflow opening(s) remain in the ascending aorta. Distal region 21 also has a configuration and size that prevents distal region 21 from passing through the aortic valve, ensuring that the blood inflow port(s) remain within the left ventricle (see FIG. 4B). As can be seen, the working portion has a length between the blood inflow and the blood outflow ports that ensures that the blood outflow port(s) are located within the ascending aorta when the blood inflow port(s) are disposed within the left ventricle.

This disclosure also includes working portions that include a plurality of impellers.

FIG. 5 illustrates an exemplary working portion 200 of a medical device that includes a proximal impeller (with blades 201) in communication with first motor 202, and a distal impeller (with blades 201') in communication with second motor 202'. By incorporating two motors into the fluid pump, the available torque can be doubled while maintaining the same maximum diameter as a single motor. This can help reduce the profile of the device. In the push-pull embodiment shown in FIG. 5, proximal motor 202 pulls blood through the working portion (which generally includes a reinforced elongate body 213, such as a coil-reinforced polymer or a braid-reinforced polymer, for example without limitation) while distal motor 202' pushes blood through the working portion. When used for left ventricle assistance, the aortic valve would be placed between the blood inflow ports 207 and the blood outflow ports 208. Elongate body 213 has inflow apertures 207 on a radially outer portion of body 213, and outflow apertures 208 on a radially outer portion of body 213. The arrows show the direction of blood flowing through the apertures, with "distal" being on the right of the page.

FIGS. 6A-6C illustrate an exemplary embodiment of working portion 300 in which proximal motor 302 pulls blood through the working portion (which can include a reinforced body 313 such as a coil-reinforced polymer or a braid-reinforced polymer, for example) while distal motor 302' pushes blood through the working portion via expandable side lumen 311. Proximal motor 302 controls and causes rotation of proximal impeller 301, and distal motor 302' controls and causes rotation of distal impeller 301'. Apertures 307 and 308 in the working portion are labeled. Expandable side lumen 311 can be expanded using mechanical techniques, such as, for example without limitation, deploying an expandable generally braided structure, or simply by inflation of the side lumen by the increased pressure generated by the distal impeller 301.' The working portion also includes inlet aperture 307 at the distal region. Side lumen 311 can be configured to expand to one side of elongate body 313, which would create a non-circular profile to the exterior of the catheter, or, as shown in the alternative FIG. 6C cross-section, it could expand more generally encircling the main reinforced catheter. At least a portion of space along a side of the reinforced body should be left exposed (e.g., one of inlet ports 307) to allow blood inflow into body 313 to support inflow to the proximal motor 302 and impeller 301. When in use for left ventricle assistance, the aortic valve could be placed between the two sets of blood inflow ports 307 and the blood outflow ports 308.

FIGS. 7A-7E illustrate another exemplary embodiment of a working portion (400) with a plurality of impellers. In this pull-pull embodiment, two impellers each pull blood through a lumen of the working portion and push the blood through side-exiting exit holes, as shown by the arrows indicating flow. Apertures 407 are inflow apertures, and outflow apertures 408 are outflow apertures. Because these impellers draw a relative vacuum to convey the blood, the lumens should be reinforced to prevent or minimize collapse. FIGS. 7B-7E illustrate the sectional views shown in FIG. 7A, respectively, and are underneath the section from which they are taken. The embodiment in FIGS. 7A-7E show a primary lumen 413 in which the motors and impellers are coaxially located. Primary lumen 413 may be coil-reinforced or braid- or similar structure-reinforced. Secondary lumen 411 expands outward from primary lumen 413, such as by an expanding braid, stent or basket-like design, similar to the secondary lumen in 311 in FIGS. 6A-6C. Blood inflow is near the distal end of the working portion. Distal motor 402' and impeller 401' drive blood to exit from at least side holes 408 that are adjacent or near the impeller 401', which can be seen in the cross-sectional view B-B of FIG. 7C showing crescent-shaped outer lumen 411 above the exit hole 408. The proximal motor 402 and impeller 401 drive blood to exit from side holes 408 adjacent or near the proximal impeller 401.

FIGS. 8A-8F illustrate another exemplary embodiment of a working portion (500) that includes a plurality of impellers, 500 and 501', with the arrows indicating direction of flow. In this push-push embodiment, the working portion 500 includes dual motors and impellers arranged in a push-push configuration, where each impeller pushes blood through a lumen of the working portion (511 or 513) and pushes the blood through side-exiting apertures or proximal-end-exiting apertures 508. Because these impellers create pressure to convey the blood, the lumens 511 and 513 do not necessarily need to be reinforced to prevent collapse and the outer lumen 511 can be fluid-inflated by pump-elevated blood pressure. This embodiment shows primary lumen 513 in which the motors and impellers are coaxially located. Primary lumen 513 may be coil-reinforced or braid- or similar structure-reinforced, for example. Secondary lumen 511 can expand outward as any of the secondary lumens above, or by fluid-inflation from pump-elevated blood pressure. Blood inflow is near the distal end of the working portion. Both lumens 511 and 513 exit blood from a proximal portion of the working portion, such as through side apertures 508, an open braid structure or similar exit passage. The two impellers 501 and 501' could be driven by a single motor with spindles exiting each end, or, as is shown in FIG. 8F, two motors 502 and 502' faced back-to-back and adjacent one another would effectively double the available torque to drive the blood pumping.

FIG. 9 illustrates an exemplary embodiment of a medical device wherein the working portion (600) includes a plurality of impellers. The medical device includes a remote motor 602 disposed at a proximal end of an elongate portion of the medical device. The remote motor 602 is coupled to drive cable 603, which is coupled to impellers 601 and 601'. Motor 602 drives the impellers. By locating the motor remotely, a larger motor can be used than would fit within a desirably smaller insertable catheter shaft. Any of the embodiments herein that include a motor within the catheter can be modified to instead have one or more remote motors. Working portion 600 can have a variety of inflow and outflow configurations and placements, such as catheter side holes 608 for each impeller or either one, or end apertures 607 that allow flow to be maximized axially instead of radially. The elongate body 604 extending between the impellers can be structurally reinforced such as by, for example, a wire-coil sandwiched between fused polymer layers, or by a generally braided structure. Coil-reinforced designs generally have better flexibility than braid-reinforced designs, and a high level of flexibility is generally desirable for navigation of the working portion into position. This embodiment or any other suitable embodiment herein can also include the remote motor with a catheter handle, or a coupled handle/hub combination.

Figure 10:
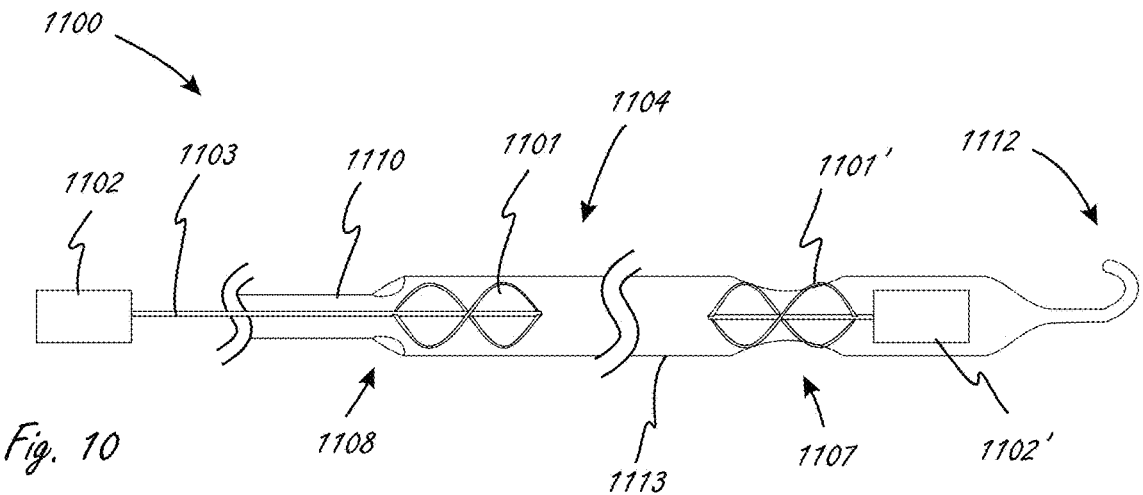
FIG. 10 illustrates at least a portion of an exemplary medical device that has a working portion.

FIG. 10 illustrates an exemplary embodiment of a medical device wherein the working portion (1100) includes a plurality of impellers. Working portion 1100 includes distal impeller 1101' coupled to motor 1102'. Working portion 1100 also includes proximal impeller 1101, which is coupled to remote motor 1102, which are in operable communication via drive-cable 1103. Distal motor 1102' is located near the distal end of the working portion and drives impeller 1101' that pushes blood through the lumen of the working portion, while remote proximal motor 1102 drives cable-driven proximal impeller 1101, which is disposed closer to the proximal end of the working portion. In use, like with other working portions herein, working portion 1100 can be positioned so that body 1113 crosses a valve (e.g., aortic valve) at a location generally between the two impellers.

Figure 11:
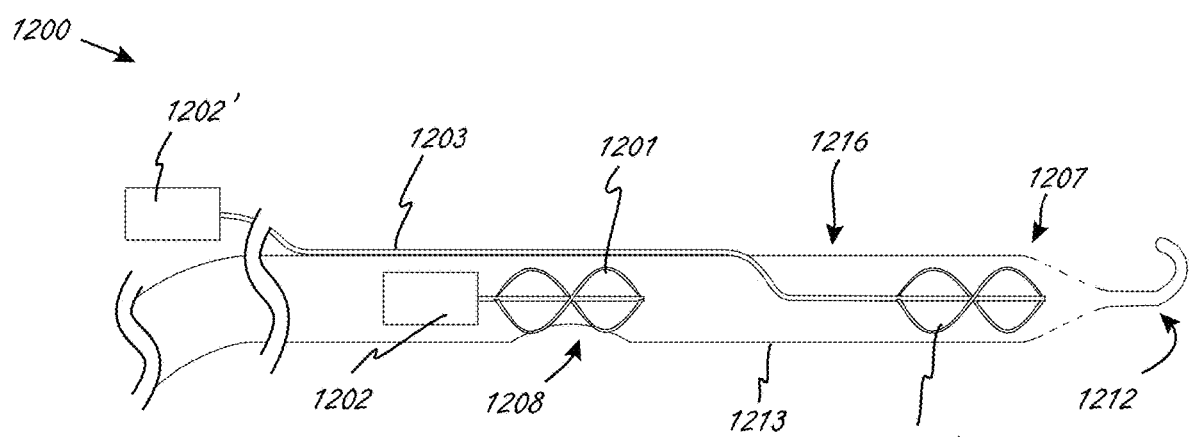
FIG. 11 illustrates at least a portion of an exemplary medical device that has a working portion.

FIG. 11 illustrates an exemplary embodiment of a medical device wherein the working portion (1200) includes a plurality of impellers. Working portion 1200 includes direct-drive proximal motor 1202 coupled to proximal impeller 1201. External motor 1202' is in operable communication with distal impeller 1201' via drive cable 1203. Drive cable 1203 can be configured within a lumen that extends along and adjacent to internal proximal motor 1202, and then extends into the working portion lumen, and is directed to be generally centered within the lumen so that the distal impeller 1201' is centered with the lumen of the working portion. Not shown are optional centering elements, such as, for example without limitation, two pair of a trio of struts that attach between the outer wall 1213 of working portion and rotational bearing elements that support the rotating drive cable 1203 so that the impeller 1201' is stably centered within the working portion lumen. Exemplary centering struts that can be used are struts 29 in FIGS. 2A and 2B.

Figure 12:
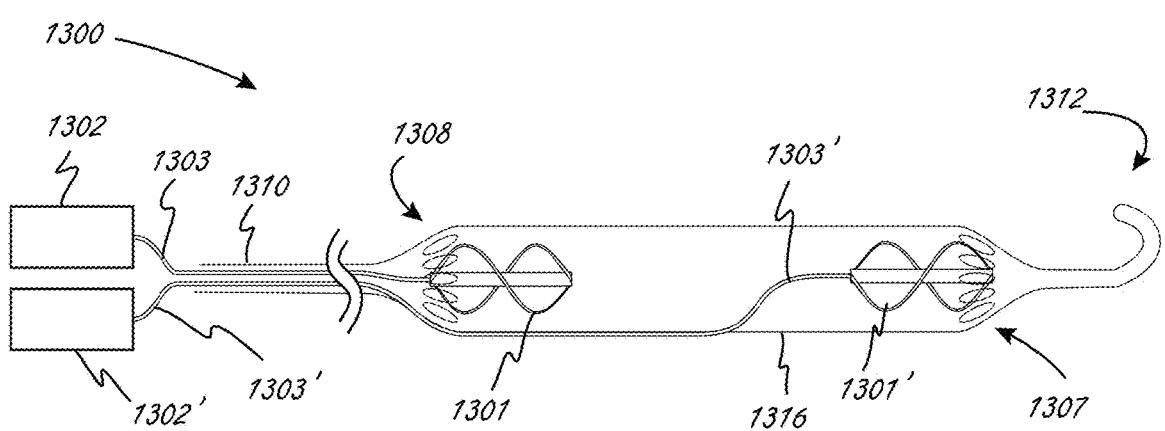
FIG. 12 illustrates at least a portion of an exemplary medical device that has a working portion.

FIG. 12 illustrates an exemplary embodiment of a medical device wherein the working portion (1300) includes a plurality of impellers. The medical device includes remote motors 1302 and 1302', which are in operable communication with drive cables 1303 and 1303', respectively. Drive cables 1303 and 1303' are in operable communication with proximal impeller 1301 and distal impeller 1301', respectively, both of which are disposed within working portion 1300. Drive cables 1303 and 1303' are disposed side by side with proximal region 1310, and drive cable 1303' extends along the periphery of the working portion for a distance, then extends towards the center of the lumen. Centering elements can be included as well, such as is described with reference to FIG. 11. The drive cables can be in separate lumens in proximal region 1310. Drive cable 1303' can be in an external lumen or within one or more bearing elements where it extends along the periphery 1316 of the working portion.

Figure 13A:
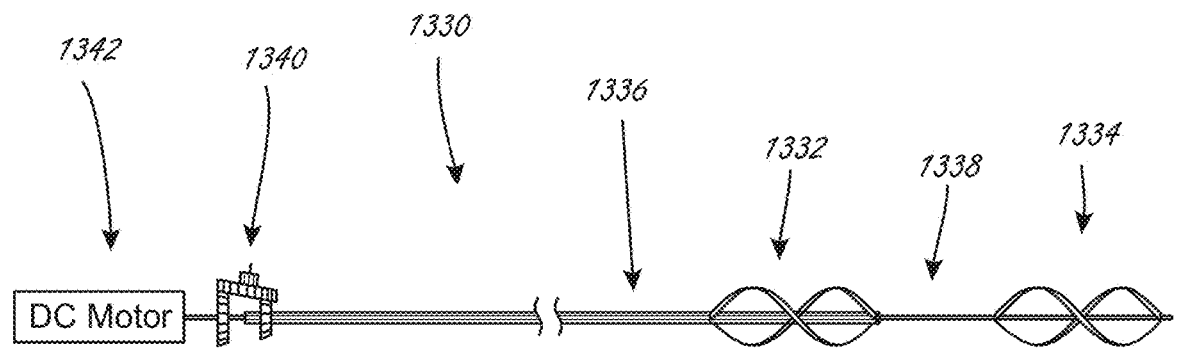
FIG. 13A illustrates at least a portion of an exemplary medical device that has a working portion, where at least two different impellers can be rotated at different speeds.

In any of the embodiments herein in which the medical device (1330) includes a plurality of impellers, the device can be adapted such that the impellers rotate at different speeds. FIG. 13A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

Figure 13B:
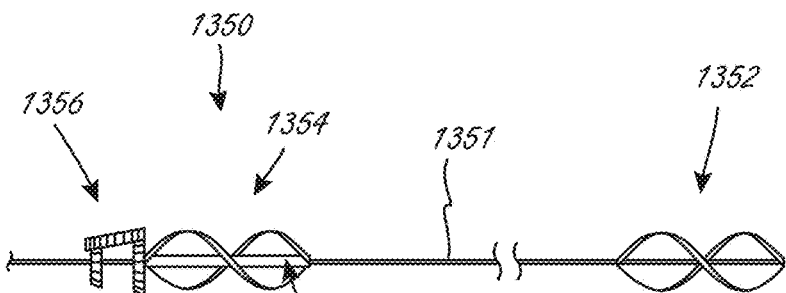
FIG. 13B illustrates at least a portion of an exemplary medical device that has a working portion, where at least two different impellers can be rotated at different speeds.

FIG. 13B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 13A. FIGS. 13A and 13B illustrate how a gearset can be adapted to drive the proximal impeller slower or faster than the distal impeller.

Figure 13C:
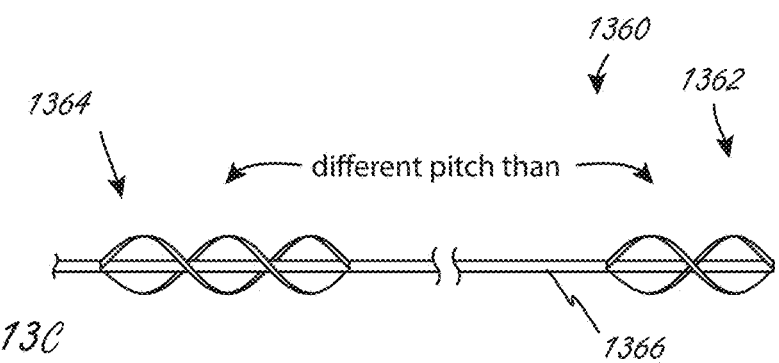
FIG. 13C illustrates at least a portion of an exemplary medical device that has a working portion with at least two impellers with different pitches.

In alternative embodiments, a common drive cable or shaft can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 13C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions herein with a plurality of impellers can be modified to include first and second impellers with different pitches.

Figure 14:
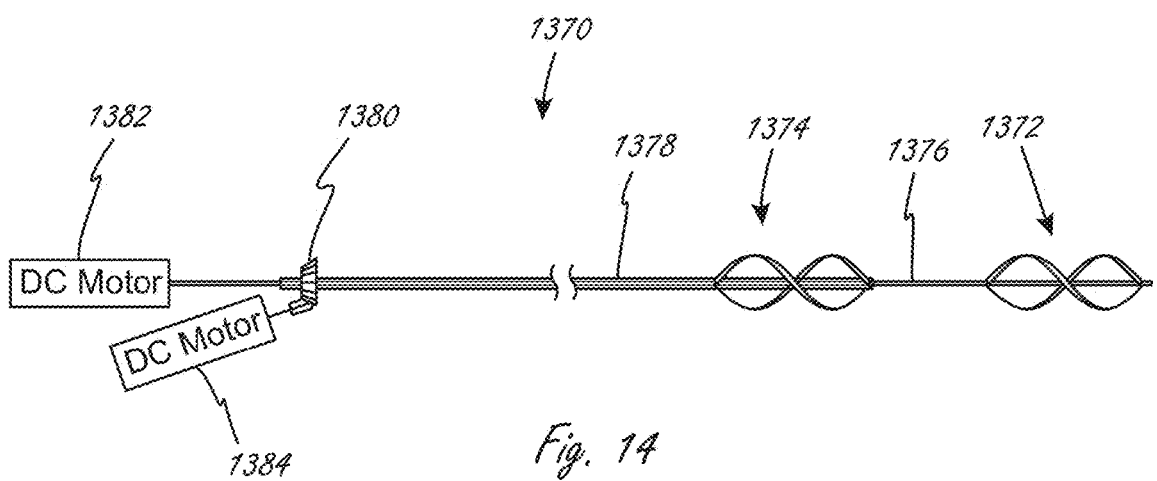
FIG. 14 illustrates at least a portion of an exemplary medical device that has a working portion.

FIG. 14 shows an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

In use, the working portions wherein may be placed across a delicate structure such as a valve (e.g., aortic valve). It may be helpful to avoid damage to the valve, and the working portion may be adapted and constructed to do so. Because the aortic valve (for example, or other similar valve) generally closes with three valves meeting near a central point, it may be advantageous for the exterior of any of the working portions herein to have a non-circular configuration at the location where the working portion crosses, or spans, the valve. It may be less desirable for a non-circular catheter body to be rotationally aligned to ideally match the aortic valve. FIGS. 15A, 15B and 15C illustrate exemplary outer profile configurations for working portions herein, which can be incorporated into any working portion herein. FIG. 15D shows a circular outer profile configuration by comparison.

In some embodiments, the working portion can have a compliant or semi-compliant exterior structure in the region where it crosses the valve so that the forces of the valve pressing against the working portion will at least partially deform the exterior structure to at least partially reduce the reactionary forces applied by the exterior structure to the valve. This can help prevent damage to the valve at the location where it spans the valve.

It may also be advantageous for the exterior of any of the working portion to be smooth so that any rubbing of fragile structures such as valve leaflets will cause minimal damage to those structures. For example, a stent-like or similar structure at that region of the valve may cause high-spots (like a dull cheese-grater) that might cause damage to the valve. Minimizing the height of such protrusions and/or minimizing the distance between them may be beneficial and prevent damage to delicate anatomical structures.

FIG. 16 is a side view illustrating a distal portion of an exemplary intravascular fluid pump, including working portion 1600, wherein working portion 1600 includes proximal impeller 1606 and distal impeller 1616, both of which are in operable communication with drive cable 1612. Working portion 1600 is in an expanded configuration in FIG. 16, but is adapted to be collapsed to a delivery configuration so that it can be delivered with a lower profile. The impellers can be attached to drive cable 1612. Drive cable 1612 is in operable communication with an external motor, not shown, and extends through elongate shaft 1610.

Working portion 1600 also includes expandable member 1602, which in this embodiment has a proximal end 1620 that extends further proximally than a proximal end of proximal impeller 1606, and a distal end 1608 that extends further distally than a distal end 1614 of distal impeller 1616. Expandable member 1602 is disposed radially outside of the impellers along the axial length of the impellers. Expandable member 1602 can be constructed in a manner and made from materials similar to many types of expandable structures that are known in the medical arts to be able to collapsed and expanded, examples of which are provided herein.

Working portion 1600 also includes conduit 1604, which is coupled to expandable member 1602, has a length L, and extends axially between the impellers. Conduit 1604 creates and provides a fluid lumen between the two impellers. When in use, fluid move through the lumen provided by conduit 1604. The conduits herein are non-permeable, or they can be semi-permeable, or even porous as long as they can still define a lumen. The conduits herein are also flexible, unless it is otherwise indicated. The conduits herein extend completely around (i.e., 360 degrees) at least a portion of the working portion. In working portion 1600, conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "O." Conduit 1604 improves impeller pumping dynamics, compared to those that working portion 1600 would have without the conduit.

Expandable member 1602 can have a variety of constructions, and made from a variety of materials, such as any variety of expandable stents or stent-like devices in the medical arts, or any other example provided herein. For example without limitation, expandable member 1602 could have an open-braided construction, such as a 24-end braid, although more or fewer braid wires could be used. An exemplary material for the expandable member is nitinol, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive cable 1612 is co-axial with the longitudinal axis in this embodiment. In use, the central region can be placed across a valve, such as an aortic valve. In some embodiments, expandable member 1602 is adapted and constructed to expand to an outermost dimension of 12-24F (4.0-8.0 mm) where the impellers are axially within the expandable member, and to an outermost dimension of 10-20F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive cable 1612 rotate within the expandable member and conduit assembly. Drive cable 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or 8,052,749, the disclosures of which are incorporated by reference herein.

Figure 17:
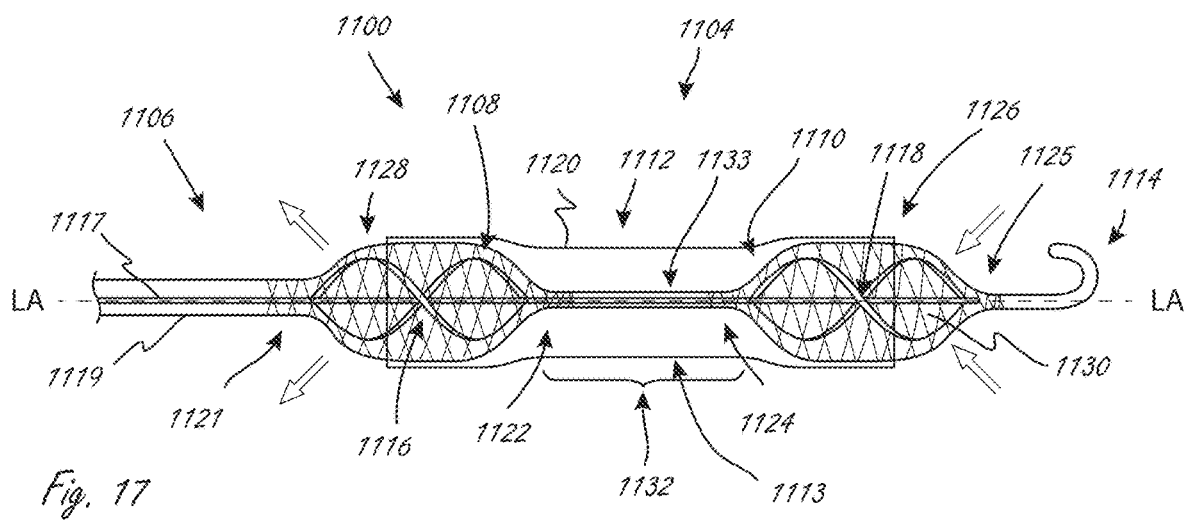
FIG. 17 is a side view of an exemplary working portion that includes a conduit, a plurality of impellers, and a plurality of expandable members.

FIG. 17 is a side view illustrating a deployed configuration (extracorporally) of a distal portion of an exemplary embodiment of a fluid movement system. Exemplary system 1100 includes working portion 1104 and an elongate portion 1106 extending from working portion 1104. Elongate portion 1106 can extend to a more proximal region of the system, not shown for clarity, and that can include, for example, a motor. Working portion 1104 includes first expandable member 1108 and second expandable member 1110, axially spaced apart along a longitudinal axis LA of working portion 1104. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a conduit being coupled to an expandable member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 17. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the conduits herein, or at least a portion of the conduit, can be impermeable to blood. In FIG. 17, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable members help maintain the conduit in an open configuration to create the lumen, while each also creates a working environment for an impeller, described below. Each of the expandable members, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 17, second expandable member 1110 extends from first end 1124 (proximal end) to second end 1125 (distal end).

In FIG. 17, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 17, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 17). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841, 976 or 8,052,749, the disclosures of which are incorporated by reference herein.

Figure 18A:
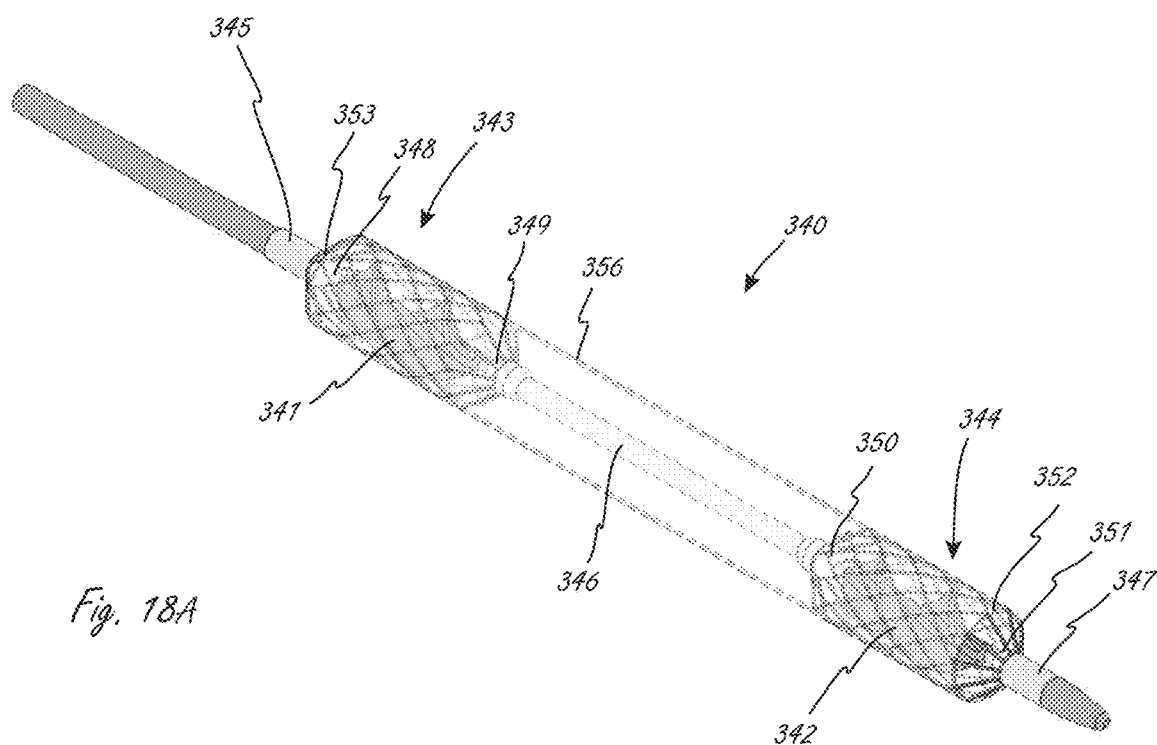
FIGS. 18A, 18B, 18C and 18D illustrate an exemplary working portion that includes a conduit, a plurality of impellers, and a plurality of expandable members.
Figure 18B:
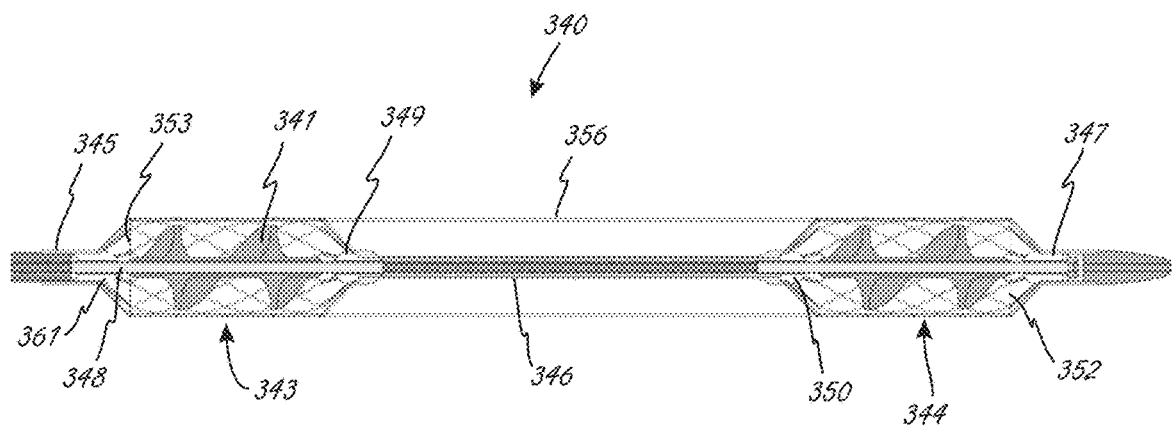
Figure 18C:
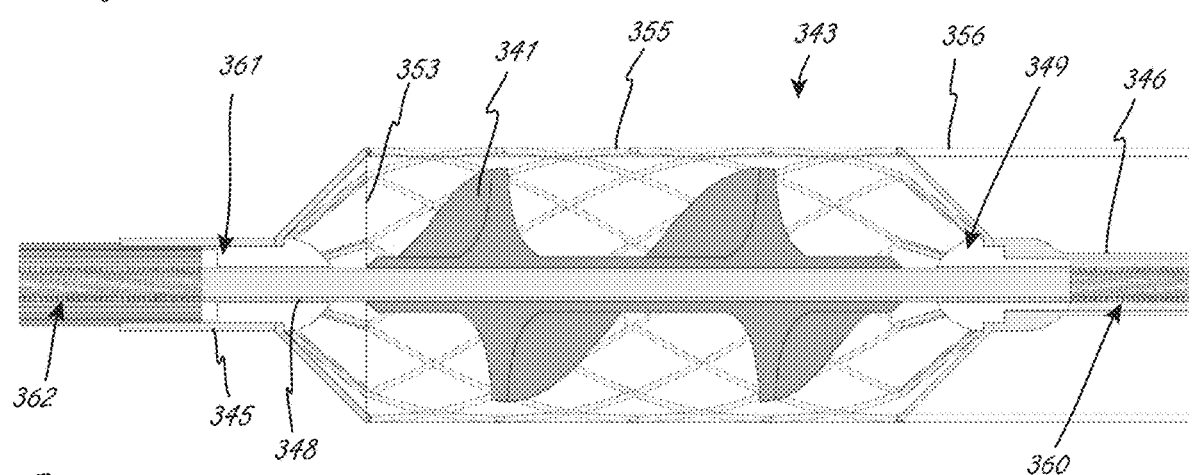
Figure 18D:
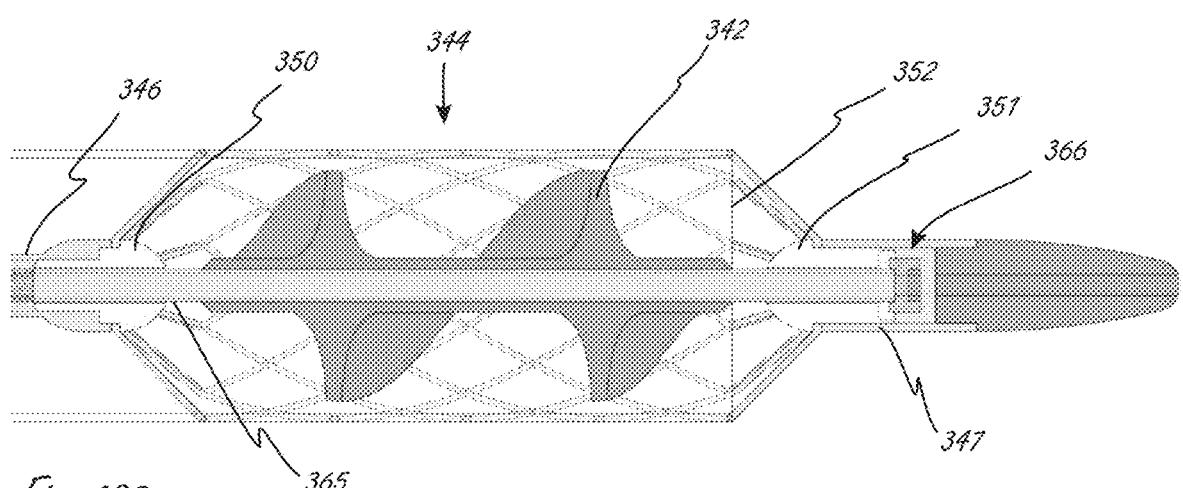

FIGS. 18A-18E show an exemplary working portion that is similar in some ways to the working portion shown in FIG. 17. Working portion 340 is similar to working portion 1104 in that in includes two expandable members axially spaced from one another when the working portion is expanded, and a conduit extending between the two expandable members. FIG. 18A is a perspective view, FIG. 18B is a side sectional view, and FIGS. 18C and 18D are close-up side sectional views of sections of the view in FIG. 18B.

Working portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Working portion 340 includes proximal expandable member 343 and distal expandable member 344, each of which extends radially outside of one of the impellers. The expandable members have distal and proximal ends that also extend axially beyond distal and proximal ends of the impellers, which can be seen in FIGS. 18B-18D. Coupled to the two expandable members is conduit 356, which has a proximal end 353 and a distal end 352. The two expandable members each include a plurality of proximal struts and a plurality of distal struts. The proximal struts in proximal expandable member 343 extend to and are secured to shaft section 345, which is coupled to bearing 361, through which the drive cable extends and is configured and sized to rotate. The distal struts of proximal expandable member 343 extend to and are secured to a proximal region (to a proximal end in this case) of central tubular member 346, which is disposed axially in between the expandable members. The proximal end of central tubular member 346 is coupled to bearing 349, as shown in FIG. 18C, through which the drive cable extends and rotates. The proximal struts of distal expandable member 344 extend to and secured to a distal region (to a distal end in this case) of central tubular member 346. Bearing 350 is also coupled to the distal region of central tubular member 346, as is shown in FIG. 18D. The drive cable extends through and rotates relative to bearing 350. Distal struts of distal expandable member extend to and are secured to shaft section 347 (see FIG. 18A), which can be considered part of the distal tip. Shaft section 347 is coupled to bearing 351 (see FIG. 18D), through which the drive cable extends and rotates relative to. The distal tip also includes bearing 366 (see FIG. 18D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 19:
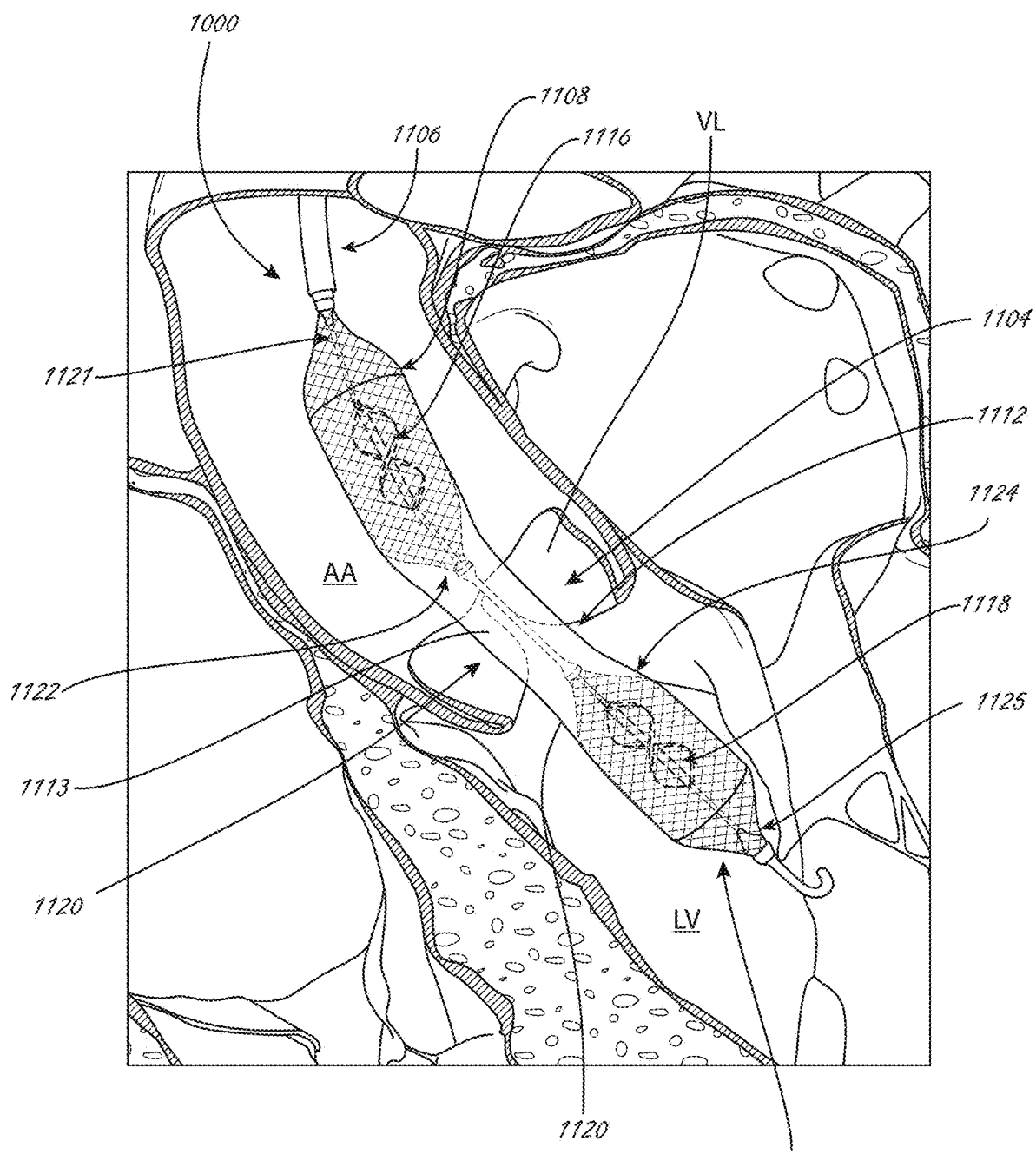
FIG. 19 illustrates an exemplary placement of a working portion, the working portion including a conduit, a plurality of expandable members, and a plurality of impellers.

FIG. 19 illustrates an exemplary placement of working portion 1104 from system 1000 from FIG. 17. One difference shown in FIG. 19 is that the conduit extends at least as far as the ends of the impellers, like in FIGS. 18A-18D. FIG. 19 shows working portion 1104 in a deployed configuration, positioned in place across an aortic valve. Working portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable member 1110, with continued proximal movement allowing first expandable member 1108 to expand.

In this embodiment, second expandable member 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable members 1108 and 1110 causes conduit 1112 to assume a more open configuration, as shown in FIG. 19. Thus, while in this embodiment conduit 1112 does not have the same self-expanding properties as the expandable members, the conduit will assume a deployed, more open configuration when the working end is deployed. At least a portion of central region 1113 of conduit 1112 is positioned at an aortic valve coaptation region. In FIG. 18, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable member 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of working portion 1104, the position of the working portion can be assessed in any way, such as under fluoroscopy. The position of the working portion can be adjusted at any time during or after deployment. For example, after second expandable member 1110 is released but before first expandable member 1108 is released, working portion 1104 can be moved axially (distally or proximally) to reposition the working portion. Additionally, for example, the working portion can be repositioned after the entire working portion has been released from a sheath to a desired final position.

It is understood that the positions of the components (relative to the anatomy) shown in FIG. 19 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein). Retraction of an outer restraint can thus, in some embodiments, allow both the expandable member and the impeller to revert naturally to a larger profile, deployed configuration without any further actuation.

As shown in the example in FIG. 19, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 16, 17, 18A-18D and 19 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 20A:
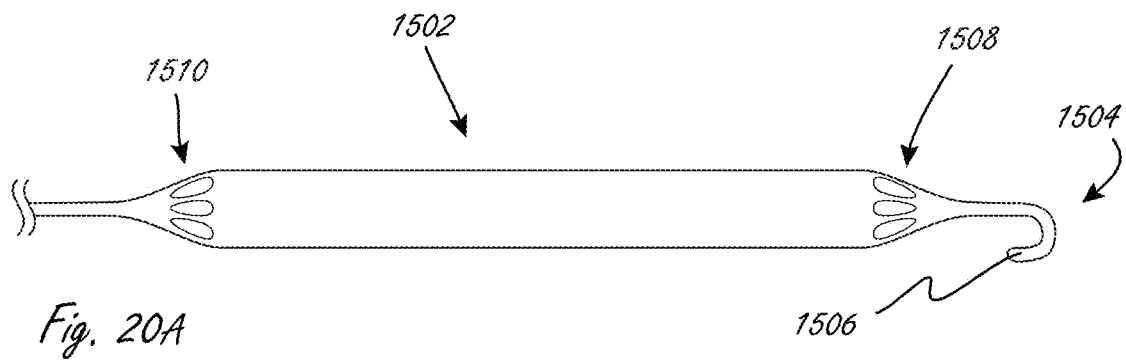
FIGS. 20A, 20B, and 20C illustrate exemplary distal end constructions and configurations for working portions.
Figure 20B:
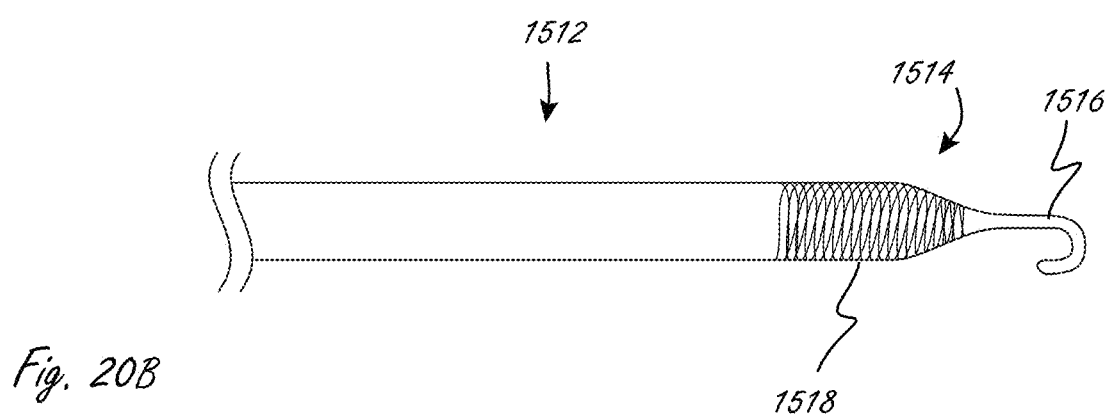
Figure 20C:
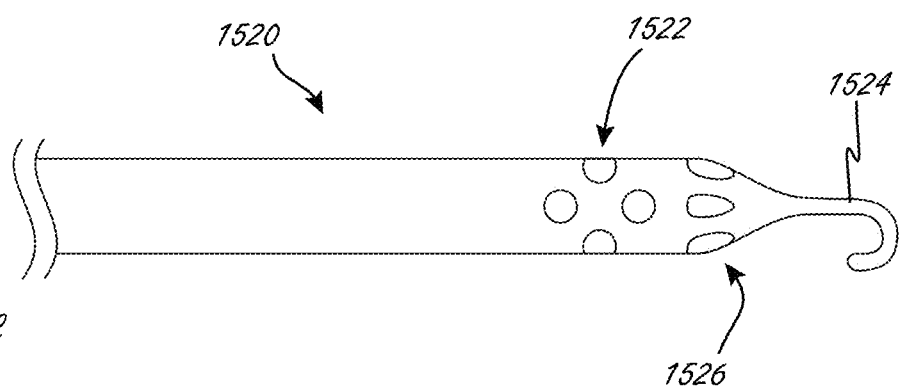

FIGS. 20A, 20B, and 20C illustrate exemplary distal end constructions and configurations for a working portion, and can be incorporated into any of the working portions herein or other working portions known in the art. FIGS. 20A-C illustrate exemplary distal tip features that may help facilitate blood flow and facilitate proper positioning across the aortic valve if the tip is positioned against a flow-blocking structure such as the apex of the left ventricle.

FIG. 20A illustrates an exemplary working portion 1502 with inflow apertures 1508 and outflow apertures 1510, and distal tip 1504 with distal end 1506. Tip 1504 can have a pigtail configuration with sufficient strength to prevent collapse when pushed against heart tissue such as left ventricular tissue. Tip 1504 could also include a stiffer internal wire (stiffer than the outer material of the distal tip).

FIG. 20B illustrates an exemplary working portion 1512 that includes tip 1516 and inflow portion 1514 adjacent and proximal to tip 1516. Inflow portion 1514 includes a plurality of elements 1518 that define a plurality of apertures that allow sufficient blood flow even pushed against heart tissue, such as left ventricular tissue. Inflow portion 1514 can be configured like a stent or stent-like device created by weaving or braiding wire or laser cutting a tubular member. Inflow portion 1514 can be comprised of, for example, self-expanding material such as nitinol.

FIG. 20C illustrates exemplary working portion 1520 that includes tip 1524 with first plurality of inflow openings 1526 with a first general configuration, and second plurality of inflow openings 1522 with a second general configuration different than the first general configuration. The plurality of openings are configured to allow sufficient blood flow even when the tip is pushed against heart tissue.

In any embodiment, a plurality of inflow openings or apertures may be molded into the design of a tip piece that is attached to the rest of the working portion by adhesive, solvent welding, ultrasonic welding, laser welding or using a similar process. Additional holes can be added near a bonded tip using, for example without limitation, core drilling or laser machining.

Figure 21A:
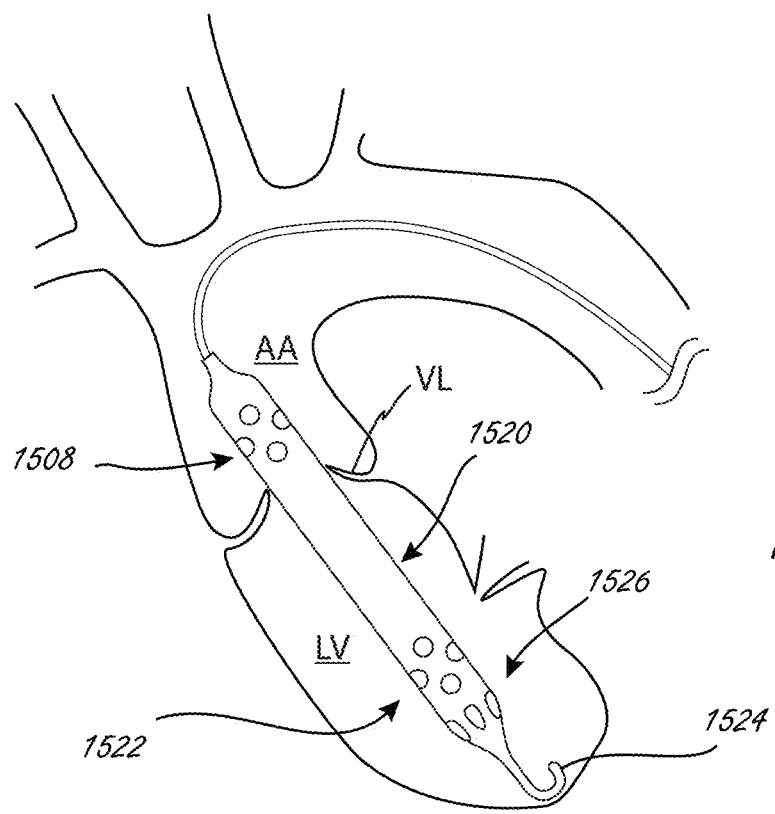
FIG. 21A illustrates an exemplary position of a deployed working portion.

FIG. 21A illustrates an exemplary position of deployed working portion 1520, wherein the length of working portion is such that a proper position across an aortic valve is achieved by urging the working portion forward until it engages left ventricular (LV) tissue, as shown. In this position, inflow inlets 1522 and 1526 are in the left ventricle, and outflow apertures 1528 are disposed in the ascending aorta, and a central region of working portions extends along the aortic valve leaflets VL.

Figure 21B:
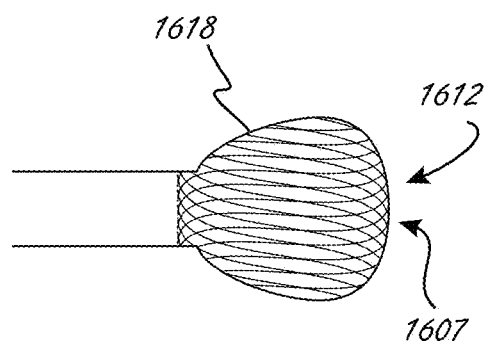
FIGS. 21B and 21C illustrate exemplary distal regions of a working portion.
Figure 21C:
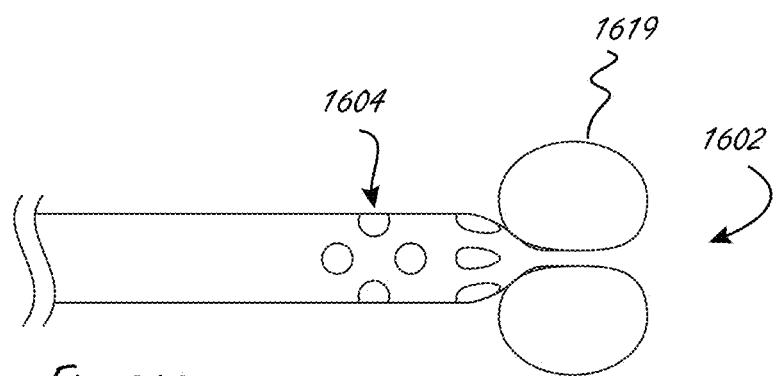

FIGS. 21B and 21C illustrate alternative distal regions of a working portion that do not include a pigtail configuration like in 20A-20C and 21A. These tip regions can be incorporated into any suitable working portion herein, or any other working portion known in the art. FIG. 21B illustrates an exemplary tip region that includes an expandable member 1612, such as a self-expanding stent-like structure, which can be formed like any expandable member herein. Expandable member 1612 has a plurality of elongate elements that define a plurality of inflow openings. The openings define sufficient open space to prevent restriction of blood flow and minimize hemolysis while also allowing adequate blood flow even if member 1612 is pushed against a structure such as a wall of the left ventricle or even the apex of the left ventricle. Member 1612 can have a variety of configurations, such as, for example, a teardrop-shape or round shape (e.g., length equal to diameter, or up to several times the diameter). Member 1612 is in this embodiment at the distal most end of the working portion.

FIG. 21C illustrates a portion of an exemplary working portion that includes distal tip 1602 that includes inlet openings 1604 and one or more inflatable members 1619 at the distal most end of the working portion. The inflatable member(s) 1619 are at the distal most end of the working portion. An inflatable tip, such as shown in FIG. 21C, could be roughly spherical, or optionally teardrop-shaped, so the more proximal end has minimal or no features that could catch on cordae tendinae or similar structures within the heart, or other features near blood vessel branches or other such hollow anatomical structure features.

Impellers herein are adapted to be collapsed from deployed, expanded configurations to collapsed, smaller outer dimension configurations, unless indicated to the contrary. This helps minimize the delivery profile for the overall working portion, and yet expand to a greater outer dimension size that can help generate the desired flow rate.

Figure 22A:
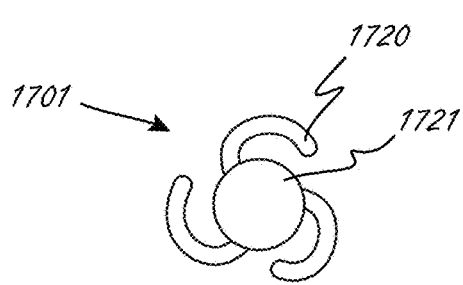
FIGS. 22A and 22B illustrate end views of an exemplary impeller, with blades in collapsed configurations (FIG. 22A) and expanded configurations (FIG. 22B).
Figure 22B:
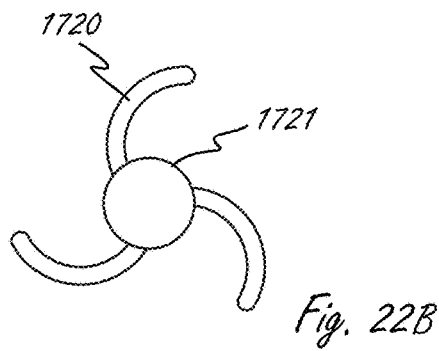

FIGS. 22A and 22B illustrate end views of an exemplary impeller 1701, with blades 1720 in collapsed configurations (FIG. 22A) and expanded configurations (FIG. 22B). The impeller includes central member 1721 from which blades 1720 extend radially. In the expanded configuration in FIG. 22B, the blades extend further radially outward relative to central member 1721. The blades can be made from materials that self-expand to larger outer dimensions, such as polymeric materials (e.g., polyethylene, polypropylene, polyester, ABS, nylon, acetal, polyphenylene sulfide), silicone, or a superelastic wireform with a polymer webbing, for example.

Figure 23A:
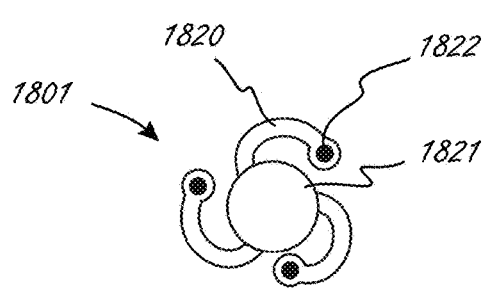
FIGS. 23A-C illustrate an exemplary impeller.
Figure 23C:
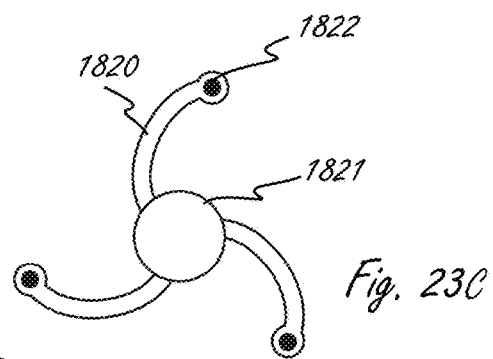
Figure 23B:
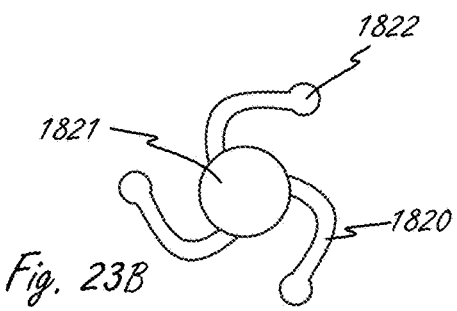

FIGS. 23A-C illustrate an exemplary impeller 1801, with blades 1820 each including weighted elements 1822 therein. Weighted elements 1822 can be weight elements of higher density (e.g., tungsten, stainless steel) or regions that have greater thickness that the rest of the blade. In the later embodiments, the elements 1822 can thus be part of the blade and not a separate component. A greater density or greater thickness would cause the impeller blades to be pulled outward by centrifugal reaction, as seen by comparing the deployed configuration in FIG. 23B and the operational configuration during rotation seen in FIG. 23C.

Figure 24A:
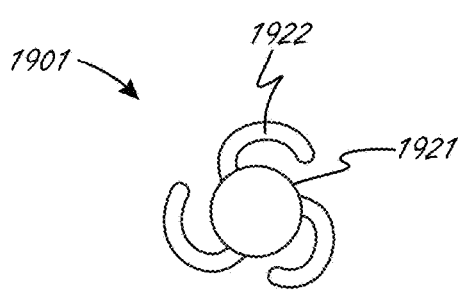
FIGS. 24A and 24B illustrate an exemplary impeller.
Figure 24B:
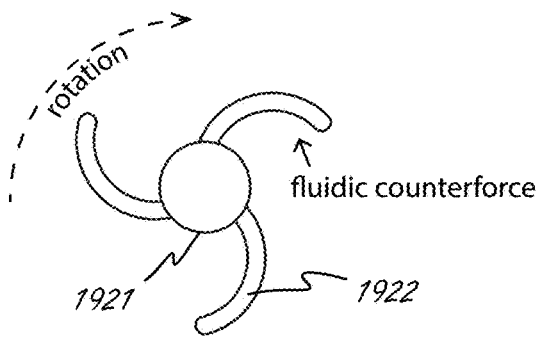

FIGS. 24A and 24B illustrate impeller 1901, with blades 1922 in collapsed and operational configurations, respectively. Impeller blades 1922 are configured to catch the fluid flow in a way that the reactionary force of the blood pushing against the face of the blades drives the impeller blade to expand from the less-expanded shape to the more-expanded shape.

Some working portions herein can include a plurality of lumens, each of which is a fluid lumen through which a fluid (e.g., blood) can flow. Dual lumen working portions can be used with, for example, dual-motor designs. More than two lumens can be incorporated as well, and thus more than two motors can also be incorporated. FIGS. 25A and 25B illustrate an exemplary multi-lumen (lumens 1922 and 1924) working portion 1920 in a collapsed, delivery configuration (FIG. 25A) and an expanded configuration (FIG. 25B). The smaller, collapsed profile enables a smaller delivery profile, and yet can be expanded to a larger dimension to allow for the desired higher flow rate, such as 4-6 L/min. Exemplary ways in which the lumens can be expanded include expansion of a braided basket structure, by inflation of the lumen by increased blood pressure, or a combination of both.

FIGS. 26A and 26B illustrates an exemplary multi-lumen design for a working portion, showing deployed and expanded configurations, respectively. Working portion 50 includes an outer body 51 in which a matrix structure 52 is embedded, such as a braided structure. Septum 53 extends across the interior of the working portion and extends radially inwards from outer body 51, dividing lumens 54 and 55. Septum 53 and outer body 51 are flexible, and stretch and become thinner (as shown) as the outer body 51 expands from the collapsed smaller outer dimension to the deployed larger outer dimension. The material(s) chosen will allow for these properties. The outer profile in this embodiment in circular.

In some relevant embodiments, additional lumens to accommodate, for example, motor wiring, fluid pressure measurement and/or a guidewire may be included. FIGS. 27A-C illustrate exemplary embodiments with such additional lumens. FIG. 27A illustrates exemplary working portion with outer wall 60, septum 61, channel 62, lumen 63 defined by channel 62, first fluid lumen 64 and second fluid lumen 65. Lumen 63 and channel 62 are within septum 61. In FIG. 26B, lumen 73 and channel 72 are disposed at an intersection between lumens 64 and 65. Working portion includes wall 70, septum 71, fluid lumen 74 and fluid lumen 75. FIG. 26C shows channel 82 and lumen 83 disposed at a periphery of wall 80 and adjacent septum 81.

Figure 28:
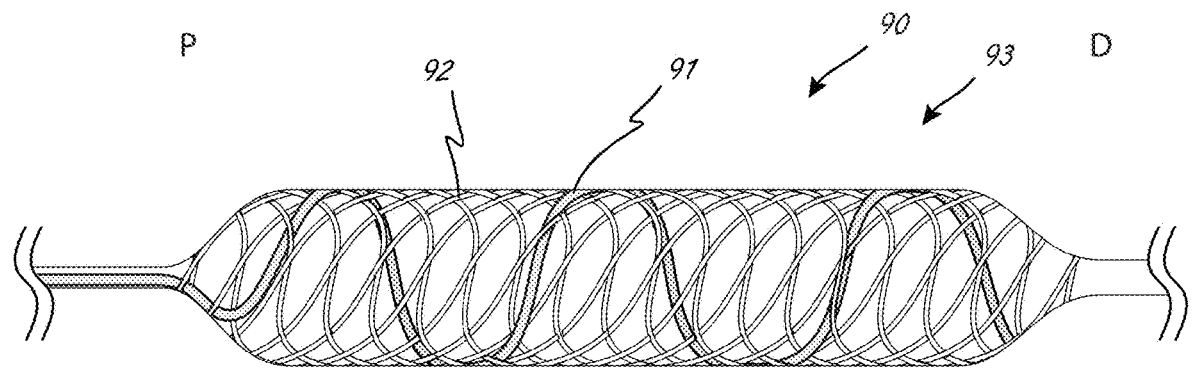
FIG. 28 illustrates an exemplary working portion.

FIG. 28 illustrates an exemplary concept in which working portion 90 includes expandable member 93, which includes a plurality of elongate segments 92 (only one is labeled). Working portion 90 also illustrates how wiring and/or lumen(s) 91 (only one is labeled but more than one can be included for different purposes) can be incorporated into the expandable member (e.g., a braided structure). Here, wire and/or lumen 91 follows the periphery of the expandable member, in a curvilinear fashion, from a proximal portion to a distal portion. Other working portion components (e.g., impeller(s), conduit) can of course be incorporated with expandable member 93. Expansion of the expandable member does not stretch the wiring and/or lumen(s) in this embodiment.

Figure 29:
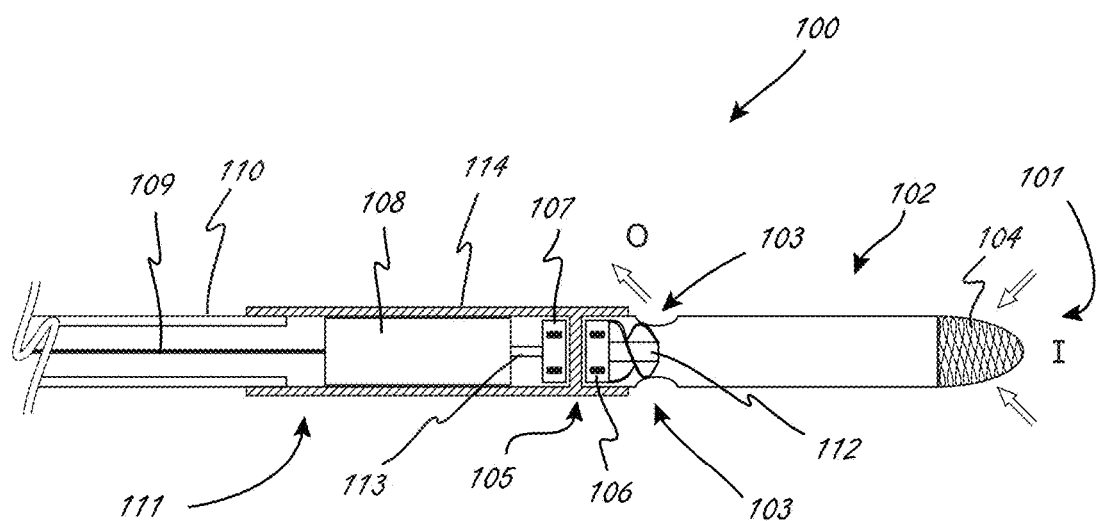
FIG. 29 illustrates an exemplary fluid movement medical device, including a working portion.

This disclosure now describes some exemplary magnetic coupling designs, which can be incorporated with any suitable working portion and medical device herein. The magnetic couplings are part of motors that can drive the rotation of one or more impellers herein. FIG. 29 illustrates an exemplary fluid movement medical device 100, which includes working portion 102, magnetic coupling 105, motor 108, shaft 113, and one or more wires 109. An exemplary advantage of the embodiment in FIG. 29 is that the motor can be re-used relatively easily for future procedures. Housing 114 houses motor 108, a distal portion of wires 109, shaft 113, and magnetic member 107. Working portion includes inflow end 101, tip 104, impeller 112, and outlet openings 103. After use, working portion 102 can be removed from housing 114, and housing 114 can be cut or severed at optional cut zone 111. This separates the motor, allowing it to be reused. This design also allows for a blood-free motor, which may be especially helpful for reuse of this component in device reprocessing. Cut zone 111 can be created to facilitate the removal of motor 108 and associated wiring without damage.

Figure 30:
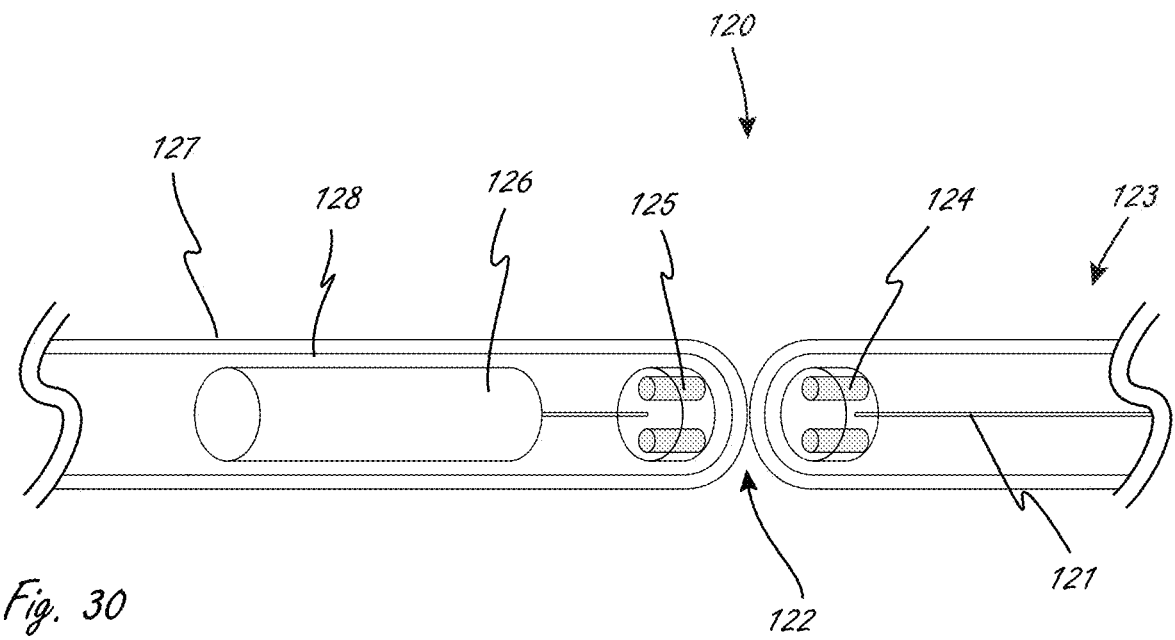
FIG. 30 illustrates an exemplary magnetic coupling for a motor and drive cable.

FIG. 30 illustrates an exemplary magnetic coupling for a motor and drive cable. This magnetic coupling arrangement may be used near the proximal end of the medical device to provide an indirect-contact gap between a drive motor and a drive cable. This arrangement allows a sterile barrier to enclose a non-sterile handle unit that includes the drive motor in a way that allows it to be magnetically coupled to a sterile catheter shaft connector. This provides an advantage that a non-sterile handle and cable assembly could be used and re-used in many medical procedures without need for cleaning, disinfection and sterilization as a multi-use assembly. A single-use catheter assembly that includes a working portion, and a single-use sterile barrier could be used for each procedure.

FIG. 30 illustrates proximal coupling 122 between motor housing 128 and catheter portion 123 of the medical device. Catheter portion 123 includes any suitable working portion herein, or other working portions known in the art. Motor housing 128 includes motor 126 coupled to magnetic member 125. Sterile sleeve 127 can be advanced over motor housing 128. Catheter portion 123 includes magnetic member 124 and drive cable 121. Activation of the motor causes rotation of the drive cable via magnetic coupling 122.

Figure 31:
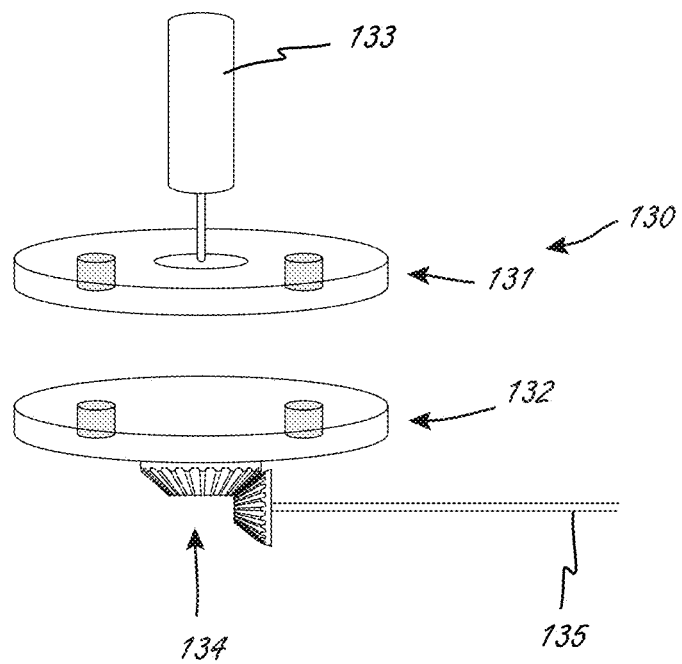
FIG. 31 illustrates an embodiment of a 90-degree gearset.

If a magnetic coupling is used with any of the medical devices herein, a larger torque lever arm may be needed. It may thus be advantageous for a larger magnetic coupler wheel to be mounted at a 90-degree angle to the catheter shaft to allow for low-height (and therefore low-volume) packaging. FIG. 31 illustrates an embodiment of this, using a 90-degree gearset to couple to the drive cable. Only a portion of the device is shown in FIG. 31 for clarity. Motor 133 is coupled to first magnetic member 131. Drive cable 135 and second magnetic member 132 are coupled to 90 degree gearset 134.

Figure 32A:
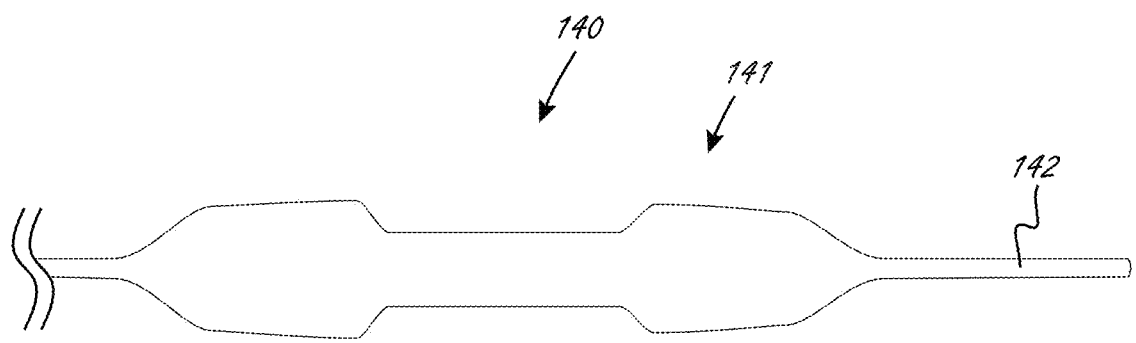
FIG. 32A illustrates an exemplary working portion including a lumen region and a distal tip in a generally straight configuration.
Figure 32B:
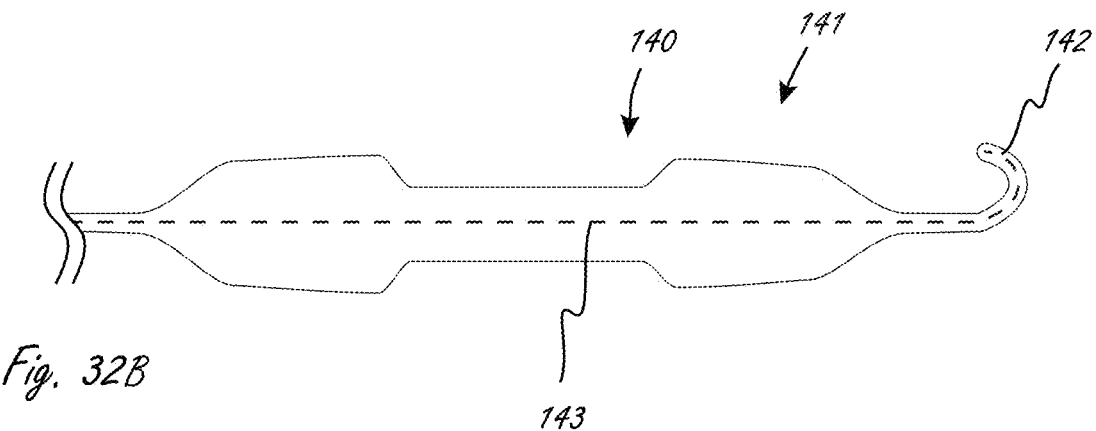
FIG. 32B shows an internal elongate member, such as a guidewire, advanced through the working portion and into a distal tip. The previously straight tip durably assumes a different configuration.

In some embodiments, a working portion can have a generally straight tip to allow for easy insertion into the body and then the tip is biased into a generally L-shape or J-shape to facilitate navigation and reduce potential trauma to intravascular or intracardiac structures. The secondary distal configuration can be accomplished by using of a stiff curved member inserted into a working portion lumen, such as a guidewire lumen. Alternatively, a secondary distal configuration can be accomplished by steerable catheter mechanisms, such as one or more pull wires within a wall of the working portion, near the distal tip. FIG. 32A illustrates exemplary working portion 140, including lumen region 141 and distal tip 142 in a generally straight configuration. FIG. 32B shows internal elongate member 143, such as a guidewire, advanced through working portion 140 and into distal tip 142. The previously straight tip 142 durably assumes a, in this embodiment, "J" configuration.

Figure 33A:
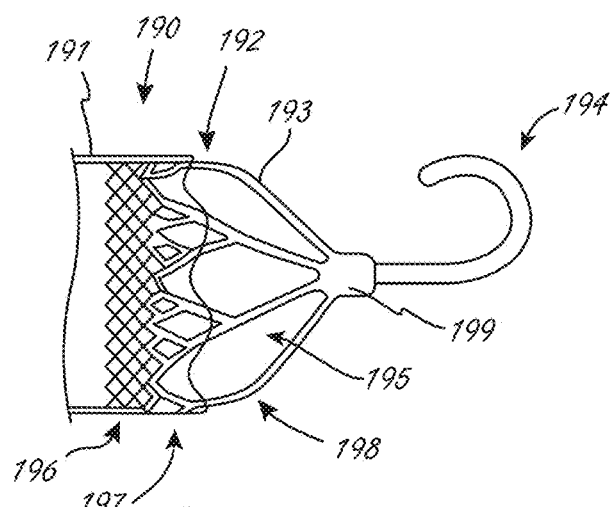
FIGS. 33A, 33B, 33C, 33D and 33E illustrate exemplary distal ends of exemplary working portions.

FIGS. 33A-33E illustrate exemplary distal ends of working portions, which can be incorporated into any suitable working portion herein or other working portion known in the art. In FIG. 33A, working portion 190 includes conduit 191 and expandable member 192. Expandable member 192 includes a plurality of elongate elements, including tapering struts 193, which extend from element 199 proximally. Struts 193 can be integral to element 199 or can be coupled thereto. Struts 193 define inlet apertures 195 (only one is labeled) for blood to flow into the working portion lumen. The distal end of expandable member 192 includes first region 198 in which at which at least one aperture has a first area, second region 197, in which at least one aperture has an intermediate aperture, and third region 196, in which at least one aperture has a third area, wherein the first area is greater than the intermediate area, and the intermediate area is greater than the third area.

Figure 33B:
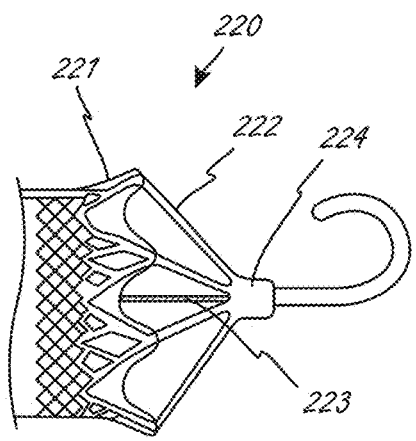

FIG. 33B is similar to FIG. 33A, the description of which is incorporated by reference into the description of FIG. 33B. Working portion 220 includes struts 222, however, that extend radially outward, then radially inward. Working portion 220 also includes elongate member 223, which can be coupled to an impeller, and interfaces element 224.

Figure 33C:
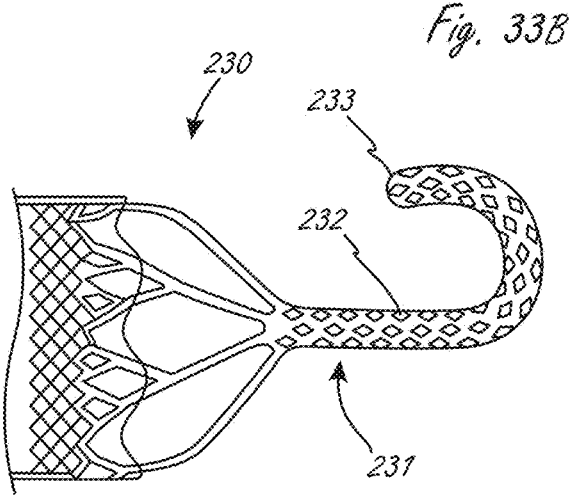

Working portion 230 in FIG. 36C is similar to FIGS. 33A and 33B, the descriptions of which are incorporated by reference into the description of FIG. 33C. Working portion 230, however, includes distal tip 231 with a curvilinear configuration and that includes a plurality of apertures 232 therein. Tip 231 has distal end 233.

Figure 33D:
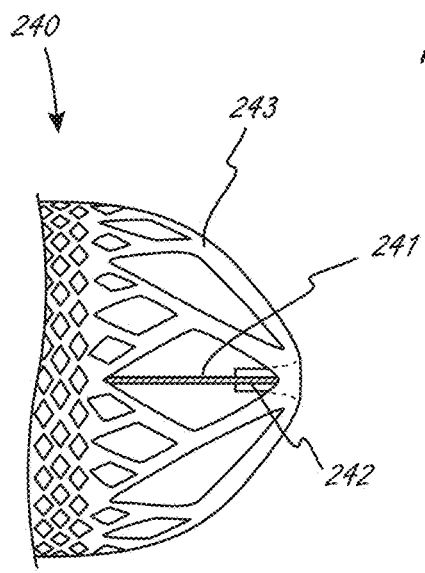

Working portion 240 in FIG. 33D is similar to FIGS. 33A-33C, the descriptions of which are incorporated by reference into the description of FIG. 33D. Working portion 240, however, includes struts 243 that taper down and meet one another at the distal end of the working portion. Working portion 240 does not have separate tip portion that extends distally struts, as is the case in FIGS. 33A-C. Working portion 240 also includes shaft 241 that is secured relative to member 242.

Figure 33E:
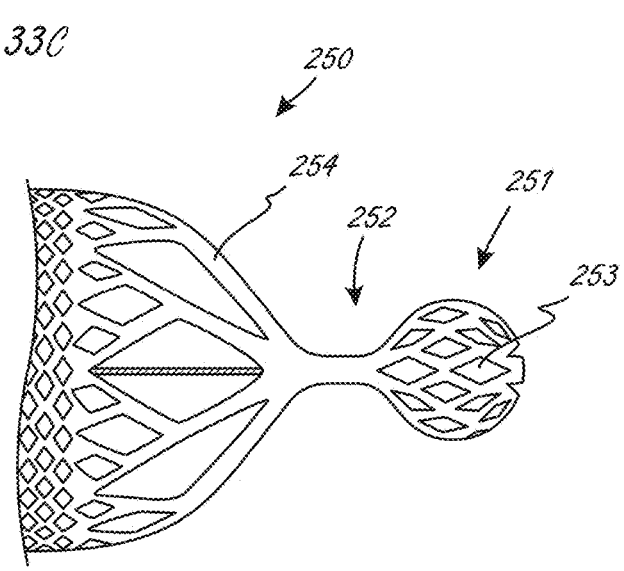

Working portion 250 in FIG. 33E is similar to FIGS. 33A-D, the descriptions of which are incorporated by reference into the description of FIG. 33E. Working portion 250, however, includes distal extension 251 that has a round configuration, which can be spherical, toroidal, egg-shaped, etc. Distal extension 251 has a plurality of holes 253 therein, and can be integrally formed with struts 254 via connector portion 252.

Figure 34:
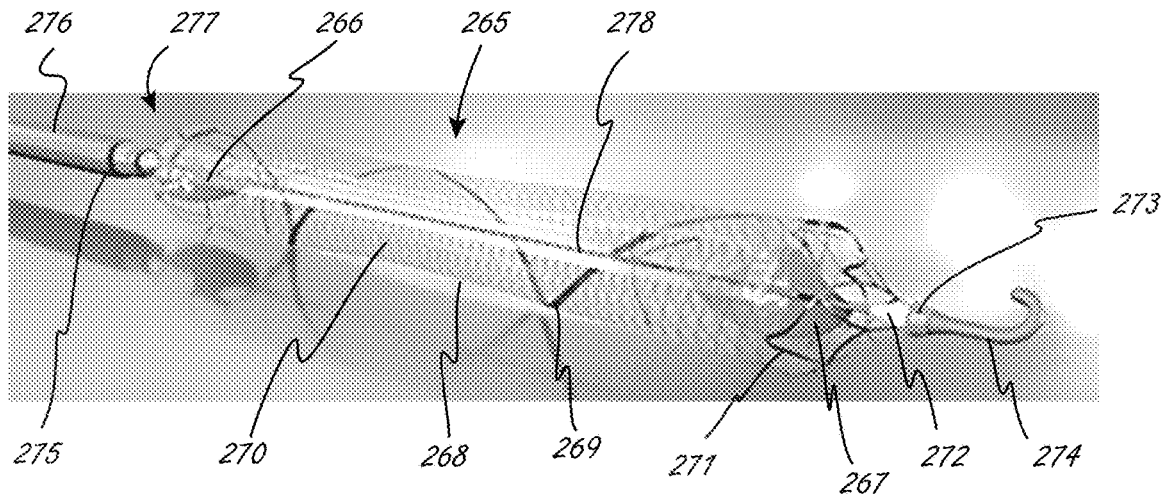
FIG. 34 illustrates an exemplary working portion.

FIG. 34 illustrates a working portion that is similar to the working portion shown in FIG. 16. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable member, referred to 270 generally, and conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 16 are incorporated by reference into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapsed by elongate (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandred the wires are braided onto as it is pulled along, especially along the length of the largest-diameter portion of the braided structure. The construction could also be accomplished during a second operation of the construction process, such as mechanically twisting a braided structure prior to heat-setting the wound profile over a shaped mandrel.

Figure 35:
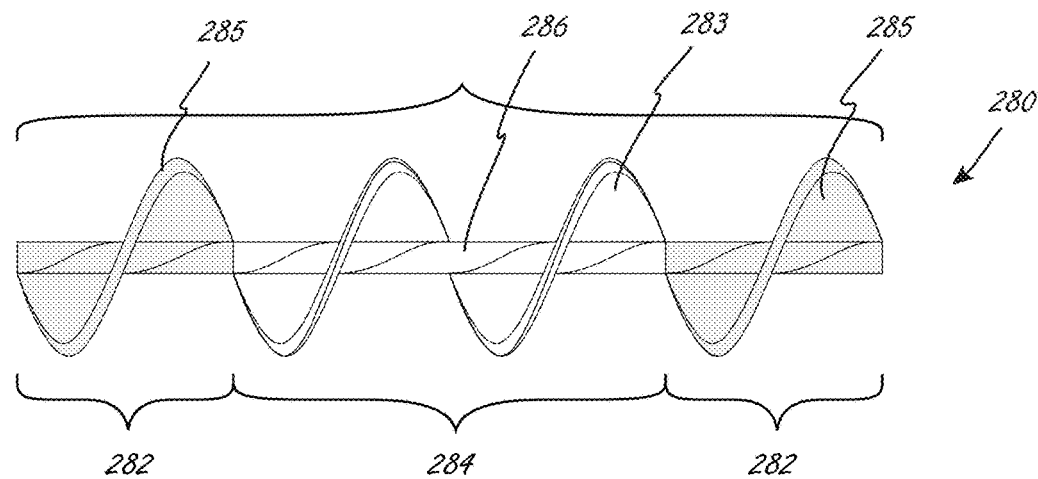
FIG. 35 illustrates an exemplary embodiment of an impeller.

FIG. 35 illustrates an alternative embodiment to any of the multi-impeller pump designs herein, in which there are two end semi-rigid impellers 282 and a helical flexible wall 283 between the impeller blades 285 that is configured with the same helical pitch as the pitch of the blades that convey blood, which is similar to an Archimedes screw. In a further embodiment, there are a plurality of radial supports along the length of the flexible wall that prevent it from collapsing onto the impeller drive shaft 286 as is the normal tendency for a flexible tube when twisted.

With any of the pigtail tips herein, the pigtail tips can have varying wall thicknesses to facilitate different being properties. In an exemplary embodiment, for example, there is a thinner wall thickness in a distal-most region of the pigtail and a relatively thicker wall thickness in a region disposed proximal to the distal-most region.

Figure 36:
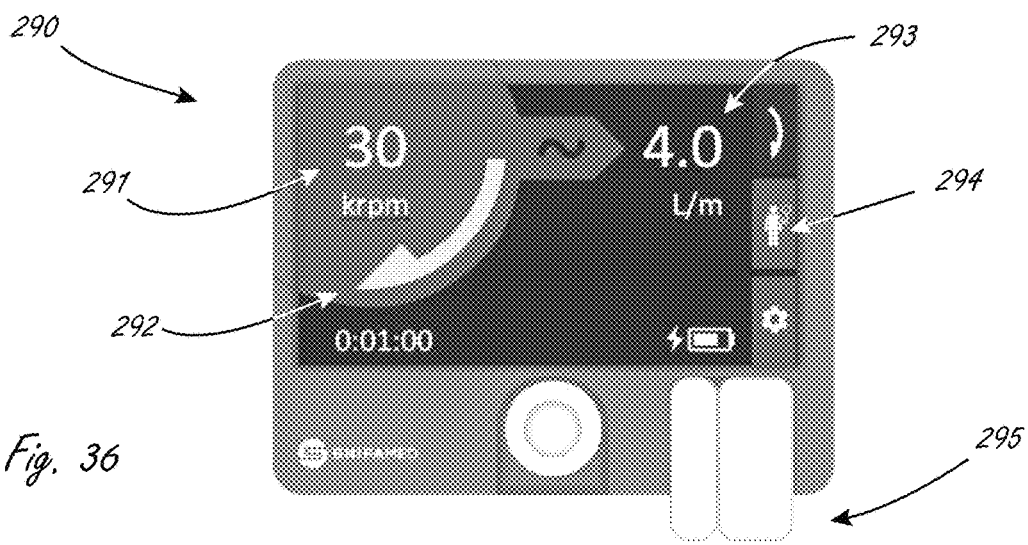
FIG. 36 shows an exemplary pump console with display.

FIG. 36 shows an exemplary pump console with display 290 that can be used with any of the fluid pumps herein. Console includes speed display element, impeller rotation indication element, estimated blood flow rate display 293, sensor display 294 (e.g., blood pressure reading), and battery icon, and fluid pump electronics and/or purge connection 295.

In some embodiments, the catheter electrical connections and fluid connections are integrated into a single connector that is configured to interface with the console, such as by, for example, magnetic attraction. In alternative embodiments, the electrical connections interface separately from fluid connections. In such an embodiment, the connections may be adjacent each other to interface as a unified pair of connectors. In some embodiments, the console is adapted to sense whether either or both connectors are properly and completely mated.

In some embodiments, fluid entrainment is used to direct blood flow, such as by injection of saline. Other exemplary fluids are dextrose solution or blood. Entrainment is the transport of fluid across an interface between two bodies of fluid by a shear induced turbulent flux, but it is important to minimize blood hemolysis that may be caused by turbulent flux.

The disclosure includes devices and methods for confirming proper positioning of the working portions herein. In some embodiments, for example, one or more ultrasound crystals (e.g., a piezoelectric crystal) re included in any of the working portions herein. The ultrasound crystal(s) can be used to indicate fluid motion such as blood flow, and may also be used to detect the motion of the aortic valve and/or the mitral valve. Exemplary locations for such sensors are near the blood outflow port(s) of a working portion and near the blood inflow port(s) of the working portion. In a method of use, the direction and degree of turbulence of blood flow can be measured by the sensor(s) and compared against reference data to determine if the working portion is located with the valve (e.g., aortic) between the blood inflow and outflow port(s). If the sensed information does not indicate proper placement, the working portions can be moved until the sensors sense indicators of proper placement. Within the ascending aorta, blood will flow primarily from the aortic valve toward the descending aorta. Conversely, within the ventricle there is much more varied or cyclical flow direction as the ventricle cavity fills and is partly emptied with each compression of the ventricle muscle. The motion of the aortic valve leaflets can also present a recognizable pattern that can be recognized as an ultrasound crystal is passed therethrough. These methods can be used with any of the methods herein.

In some embodiments, the medical device includes a miniature video camera (e.g., coupled to the working portion or just proximal to the working portion) to directly view the anatomy during working portion placement and confirmation, and moved if desired. In exemplary embodiments, one or more cameras is placed proximal to the outflow port(s) of the working portion so that the user can directly view the distal end of the working portion as directed through the aortic valve. Visible markings that are disposed on the catheter shaft may further indicate that the catheter is placed preferably in relation to a valve, such as an aortic valve (e.g., the working portion can be located so that the valve is between the blood inflow and outflow ports). In some embodiments, the video camera system is adapted to visualize through a blood-filled vessel such as the aorta, such as by radiation of a wavelength with minimum of total optical losses through blood. An exemplary wavelength is within the infrared spectrum. In some embodiments, the radiation of the wavelength is reflected and backscattered at least partly by a cardiovascular or catheter surface, detecting all intensity signals of the reflected and backscattered radiation, and processing the detected signals by selecting intensity signals of radiation being backscattered by blood only, and subtracting the selected intensity signals of radiation backscattered only by blood from all detected intensity signals of reflected and backscattered radiation, so as to reconstruct an image of the cardiovascular or catheter surface using the intensity signals of difference obtained by subtracting.

In any relevant embodiment herein, ferrofluid may be used as a bearing or seal to prevent blood from entering the working portion bearings and/or the motor assembly. In some embodiments, Ferrofluid is contained in a separate reservoir or channel during gas sterilization of the device, and then released or injected into the magnetic field to fill the intended space to act as a bearing and/or seal. In some embodiments, a reservoir(s) containing ferrofluid comprises a membrane that dissolves with fluid contact such as by flushing the device with saline or by blood contact, so that when the membrane dissolves the ferrofluid is released into position.

In some embodiments, a drive motor in the handle can be cooled by thermoelectric cooler (TEC) with heat from the hot end of TEC dissipated by cooling fins or fluid circulation. Alternatively, a drive motor in a handle can be cooled by plurality of cooling fins exposed to air. The cooling fins may have air driven across them by an air-driving fan.

In some embodiments, torque feedback can be used to determine if the blood inlet and outlet ports are positioned on opposite side of a valve, such as an aortic valve. An exemplary method of measuring torque feedback is under direct observation of position and flow rate with the working portion positioned across valve, and also with inlets/outlets fully within the ventricle/ascending aorta, to determine the torque boundaries as a function of impeller rotation speed. These boundaries can be used to confirm that the inlets and outlets are on opposite sides of the aortic valve.

In any of the relevant embodiments herein, the working portion may have one or more fluid exit holes between a distal impeller and a proximal impeller, such that the fluid exit holes may support cardiac arteries in a system where the distal impeller section is within the left ventricle and the proximal impeller system is within the ascending aorta.

The blood outflow end of working portions herein may include a filter adapted to catch thrombus and/or debris.

In some embodiments, a first impeller (e.g., a distal or proximal impeller) can be fixedly secured to a drive cable and a second impeller (e.g., a distal or proximal impeller) can be configured to slide (e.g., proximally or distally) along the drive cable when the system is collapsed. The slidable impeller is, however, configured to be mechanically engaged with the fixed impeller when the system is expanded. The mechanical engagement can be created by intermediate tubing with geared or slotted ends so that the intermediate tubing transfers torque from the first impeller to the second impeller. In alternate embodiments, three or more impellers can be similarly configured where one impeller is attached to a drive cable and the remaining impellers are mechanically engaged with the attached impeller.

When any of the methods of delivery, positioning, and use are performed, any of the following additional steps can also be performed, in any combination thereof. The following optional steps describe some clinical steps or processes that can be performed as part of a pVAD procedure.

An exemplary process that can be performed is to measure activated clotting time ("ACT") or partial thromboplastin time ("PTT") to assess anticoagulation. In any of the embodiments herein, an ACT or PTT sensor can be incorporated into or attached to a fluid-pumping device, such as on a working portion thereon. ACT and/or PTT can be measured during any or all of the following time periods: before the fluid device is inserted, during fluid device use (e.g., every 4-8 hours), after fluid pump pemoval, and before sheath removal. When hemolysis occurs, hemoglobin and hematocrit decrease, haptoglobin decreases and plasma free hemoglobin increases.

Another exemplary step that can be performed is to verify that no access site limb ischemia has occurred due to obstruction. In any of the embodiments herein, one or more sensors for blood flow rate can be located on the fluid-pumping catheter or on an arterial or venous access sheath.

Another exemplary step that can be performed is to assess an arterial access site regularly for bleeding or hematoma. In any of the embodiments herein, an arterial or venous access sheath can include one or more sensors adapted to detect bleeding or hematoma at the vessel access site.

Another exemplary step that can be performed, depending on the device used and the method of positioning it, is to verify that the working portion has been advanced properly and is positioned across valve (e.g., see FIG. 18 showing positioning across an aortic valve). For example, fluoroscopy can be used to confirm proper position of a working portion in a left ventricle and across an aortic valve. Sensed pressure can also be used to verify proper positioning. For example, an assessment can be performed on the ventricular and the aortic waveform. Additionally, at higher flow rates, or if ventricular function is poor, patient blood flow may be non-pulsatile. The motor current signal can also be used to determine proper positioning. For example, a motor current signal flattens if the working portion flow inlet and the flow outlet are in the left ventricle or aorta, or if ventricular function is poor. For example, a process engine can monitor motor current for an atypical pattern that has been correlated with recirculation of fluid from the pump flow outlet to the flow inlet. Additionally, the pump can be adapted to verify that there no suction in the ventricle.

Another exemplary step that can be performed is to assess for an indication of aortic valve damage. For example, one or more strain gauge sensors can be positioned on the working portion in a region where the working spans a valve, such as an aortic valve.

Another exemplary step that can be performed is to sense a blood flow rate conveyed by the fluid pump. For example, one or more flow rate sensors can be part of a working portion of disposed on the device immediately adjacent to a working portion. For example, an ultrasound crystal sensor can be placed on or within the device, such as on or within a working portion, and aligned to measure the flow of blood that is propelled by the working portion. In addition to or alternatively, a doppler crystal can be used to measure the velocity of blood flowing within the working portion or exiting the working portion.

Another exemplary step that can be performed is to sense the speed of rotation of one or more impellers, and correlate that with a blood flow rate.

Another exemplary step that can be performed is to verify, optionally frequently, that the patient has no hemodynamic instability. For example, a blood-pumping system can include a plurality of electrocardiogram leads to measure the conduction of electrical signals that indicate cardiac function such as the beating of the heart.

Another exemplary step that can be performed is to perform continuous cardiac output monitoring, which may be useful for patients with cardiogenic shock. For example, a fluid-pumping device, such as a working portion, can include one or more sensors such as thermodilution sensors to indicate cardiac ejection fraction and/or cardiac index.

In some uses, inotropic agents, such as dobutamine and milrinone, and vasopressors, such as dopamine and norepinephrine, may still be needed after the fluid pump is placed to maintain a cardiac index of at least 2 and systolic blood pressure at 90 mm Hg or higher.

If the patient requires interrogation of a permanent pacemaker or implantable cardioverter defibrillator, the fluid pump console can be turned off for a few seconds while the signal is established. For example, all potential electrical contacts within a fluid-pump and the patient are electrically isolated so that there is no potential for electrical interference between the fluid-pump system and an active implanted electronic device such as a pacemaker or implantable cardiverter defibrillator.

Part of any of the methods herein is verification that there are no complications, such as no reflow, no hypotension, and no lethal arrhythmia.

In some embodiments, transthoracic echocardiography (TTE) can be performed to assess, for example, left ventricular size and function.

In some embodiments, the patient positioning is taken into consideration of ventilation and thrombosis/ulcer prophylaxis.

In some uses, the temperature of a motor and/or cable can be monitored to indicate blood ingress/charring.

In some embodiments, one or more strain sensors can be incorporated into any of the expandable members, and can be used to gauge deployment of the expandable member.

What is claimed is:

1. A method of deploying an intravascular blood pump across an aortic valve, comprising:
    advancing an intravascular blood pump to a region of a heart valve, the intravascular blood pump comprising a distal expandable member, a distal impeller, a proximal expandable member, a proximal impeller, and a conduit;
    deploying the distal expandable member and the distal impeller each from collapsed delivery configurations to deployed configurations, the distal impeller disposed axially and radially within the distal expandable member in their deployed configurations;
    deploying the proximal expandable member and the proximal impeller each from collapsed delivery configurations to deployed configurations, the proximal impeller disposed axially and radially within the proximal expandable member in their deployed configurations,
    wherein when the distal and proximal expandable members are in their deployed configurations, they are axially spaced apart such that a proximal end of the distal expandable member is distal to a distal end of the proximal expandable member;
    positioning at least a portion of the distal expandable member in a left ventricle so that a distal end of the distal expandable member is distal to aortic valve leaflets;
    positioning at least a portion of the proximal expandable member in an ascending aorta so that a proximal end of the proximal expandable member is proximal to the aortic valve leaflets;
    positioning a central region of the intravascular blood pump to interface with the aortic valve leaflets, the central region of the intravascular blood pump including a central region of the conduit, the central region of the intravascular blood pump more flexible than a blood pump distal region that is distal to the central region of the intravascular blood pump and more flexible than a blood pump proximal region that is proximal to the central region of the intravascular blood pump;
    positioning the central region of the conduit that is axially in between the deployed distal expandable member and the deployed proximal expandable member such that the central region is positioned to interface with the aortic valve leaflets;
    maintaining the distal expandable member, the proximal expandable member, and the central region of the conduit in their respective positions at the same time; and
    activating the distal and proximal impellers with a common rotatable drive mechanism that extends through a catheter, through the proximal impeller, between the proximal impeller and the distal impeller, through the distal impeller, and is coupled to the proximal and distal impellers, to cause the proximal and distal impellers to rotate and move fluid from the left ventricle towards the ascending aorta,
    wherein positioning the central region of the intravascular blood pump to interface with the aortic valve leaflets further comprises positioning a region of the common rotatable drive mechanism that is between the proximal impeller and the distal impeller across the aortic valve leaflets, wherein the region of the common rotatable drive mechanism that is between the proximal impeller and the distal impeller is more flexible than the common rotatable drive mechanism where it extends through the proximal impeller and more flexible than the common rotatable drive mechanism where it extends through the distal impeller.

2. The method of claim 1, wherein positioning at least a portion of the distal expandable member in a left ventricle comprises positioning the entire distal expandable member distal to aortic valve leaflets.

3. The method of claim 1, wherein positioning at least a portion of the proximal expandable member in an ascending aorta comprises positioning the entire proximal expandable member proximal to aortic valve leaflets.

4. The method of claim 1, wherein the deploying steps comprise allowing the distal expandable member and the proximal expandable member to self-expand.

5. The method of claim 1, wherein the central region of the intravascular blood pump further includes a central expandable member between the distal proximal member and the proximal expandable member.

* * * * *